US010867146B2

(12) United States Patent
Tsai et al.

(10) Patent No.: US 10,867,146 B2
(45) Date of Patent: Dec. 15, 2020

(54) ATOMIZATION SYSTEM HAVING DOUBLE AUTHENTICATION MECHANISM

(71) Applicant: HCMed Innovations Co., LTD, Taipei (TW)

(72) Inventors: Chien-Shen Tsai, New Taipei (TW); Wen-Yu Tsai, Taipei (TW); Chieh-Sheng Cheng, Taipei (TW)

(73) Assignee: HCMed Innovations Co., LTD, Taipei (TW)

( * ) Notice: Subject to any disclaimer, the term of this patent is extended or adjusted under 35 U.S.C. 154(b) by 237 days.

(21) Appl. No.: 16/136,267

(22) Filed: Sep. 20, 2018

(65) Prior Publication Data

US 2019/0278964 A1 Sep. 12, 2019

(30) Foreign Application Priority Data

Mar. 9, 2018 (TW) ............................ 107108104 A

(51) Int. Cl.
*H04L 29/06* (2006.01)
*G06K 7/14* (2006.01)
(Continued)

(52) U.S. Cl.
CPC ....... *G06K 7/1417* (2013.01); *G06Q 30/0185* (2013.01); *G16H 20/10* (2018.01);
(Continued)

(58) Field of Classification Search
CPC .. G06K 7/1417; G16H 20/10; G06Q 30/0185; H04L 63/083; H04L 63/102; H04W 12/06
(Continued)

(56) References Cited

U.S. PATENT DOCUMENTS

2007/0074722 A1 4/2007 Giroux et al.
2008/0004540 A1 1/2008 Nakao et al.
(Continued)

FOREIGN PATENT DOCUMENTS

CN 104303524 A 1/2015
CN 104321779 A 1/2015
(Continued)

*Primary Examiner* — Michael S McNally
(74) *Attorney, Agent, or Firm* — Li & Cai Intellectual Property Office

(57) ABSTRACT

An atomizing system and device having a double authentication mechanism are provided. The system includes at least one atomizing drug container, an atomizing device and a user device. The at least one atomized medicine container associates with an authentication code carrier and contains the atomized medicine. The atomizing device includes an atomizing module, a power module, a control unit, a first communication module. The second communication module of the user device is configured to be paired with the first communication module and connected with a cloud server through the network, and the authentication module of the user device is configured to perform an authentication operation associated with the authentication code carrier to determine the authenticity of the at least one atomized medicine container or the atomized medicine through the cloud server and generate an authentication result signal correspondingly.

14 Claims, 37 Drawing Sheets

(51) Int. Cl.

| | |
|---|---|
| ***G06Q 30/00*** | (2012.01) |
| ***H04W 12/06*** | (2009.01) |
| ***G16H 20/10*** | (2018.01) |

(52) U.S. Cl.
CPC .......... *H04L 63/083* (2013.01); *H04L 63/102* (2013.01); *H04W 12/06* (2013.01)

(58) Field of Classification Search
USPC ................................................................ 726/4
See application file for complete search history.

(56) References Cited

U.S. PATENT DOCUMENTS

| | | | | |
|---|---|---|---|---|
| 2013/0238360 | A1* | 9/2013 | Bhathal | G16H 10/60 705/3 |
| 2013/0284192 | A1 | 10/2013 | Peleg Eyal | |
| 2016/0050196 | A1 | 2/2016 | Wu | |
| 2016/0174076 | A1* | 6/2016 | Wu | H04W 12/12 455/410 |
| 2016/0269375 | A1* | 9/2016 | Wu | G06F 21/35 |
| 2017/0249442 | A1 | 8/2017 | Hagen et al. | |
| 2018/0011988 | A1 | 1/2018 | Ziegler | |
| 2018/0060873 | A1* | 3/2018 | Chu | G06K 7/10297 |
| 2018/0263288 | A1* | 9/2018 | Goldstein | A61M 11/042 |
| 2018/0279918 | A1* | 10/2018 | Hagen | A61M 11/005 |

FOREIGN PATENT DOCUMENTS

| | | | |
|---|---|---|---|
| CN | 104335608 | A | 2/2015 |
| CN | 107111687 | A | 8/2017 |
| CN | 107818468 | A | 3/2018 |
| CN | 208314820 | U | 1/2019 |
| TW | M519556 | U | 4/2016 |
| TW | I613971 | B | 2/2018 |
| WO | WO2015/106390 | A1 | 7/2015 |
| WO | WO2017/124419 | A1 | 7/2017 |

* cited by examiner

```
                    ┌─────────────────────────────┐
                    │ placing atomized medicine contained in │
                    │ atomized medicine container into containing │──S250
                    │   portion of atomizing device         │
                    └─────────────────────────────┘
                                    ↓
                    ┌─────────────────────────────┐
                    │ configuring communication module to │──S251        ┌──S253
                    │ connect with cloud server through network │              ╱
                    └─────────────────────────────┘           ┌─ ─ ─ ─ ─ ─ ─ ─ ─ ─ ┐
                                    ↓           S252          │  configuring second │
                    ┌─────────────────────────────┐            │  wireless identifier of │
                    │ configuring second authentication module of │      │  second authentication │
                    │ user device to perform authentication operation │──→│  module to obtain │
                    │   related to authentication code carrier │          │    authentication    │
                    └─────────────────────────────┘            │ information of wireless │
                                    ↑←──────────────────────────│ identification chip │
                                    ↓                          └─ ─ ─ ─ ─ ─ ─ ─ ─ ─ ┘
                              ╱S254╲                              S255
                         ╱ configuring cloud server to ╲       ┌──────────────┐
                        ╱    determine authenticity of  ╲ Fake │ authentication│
                       ╱   atomized medicine container or ╲───→│     fail     │
                        ╲       atomized medicine       ╱      └──────────────┘
                         ╲                            ╱              ↓
                              ╲                    ╱             ┌─────┐
                                   ↓ True                        │ End │──S256
                    ┌─────────────────────────────┐              └─────┘
                    │ configuring second authentication module to │──S257
                    │   generate wireless identification signal │
                    └─────────────────────────────┘
                                    ↓
                    ┌─────────────────────────────────────────┐
                    │ controlling second authentication module to transmit wireless │──S258
                    │ identification signal to antenna module of atomization device │
                    └─────────────────────────────────────────┘
                                    ↓
                    ┌─────────────────────────────────────────┐
                    │ configuring first authentication module of │
                    │ atomization device to perform second authentication │──S259
                    │ operation related to wireless identification signal │
                    └─────────────────────────────────────────┘
                                    ↓
                                 S259-1
                              ╱       ╲       No   ┌──────────────────┐
                             ╱ wireless ╲──────────→│ authentication fail │──S259-2
                              ╲ signal correct? ╱   └──────────────────┘
                               ╲          ╱                ↓
                                    ↓ Yes                ┌─────┐
                    ┌─────────────────────────────┐       │ End │──S259-3
                    │ enabling control unit to control power module to output │  └─────┘
                    │ driving voltage to drive atomization element of │──S259-4
                    │  atomization device to atomize atomized medicine │
                    └─────────────────────────────┘
```

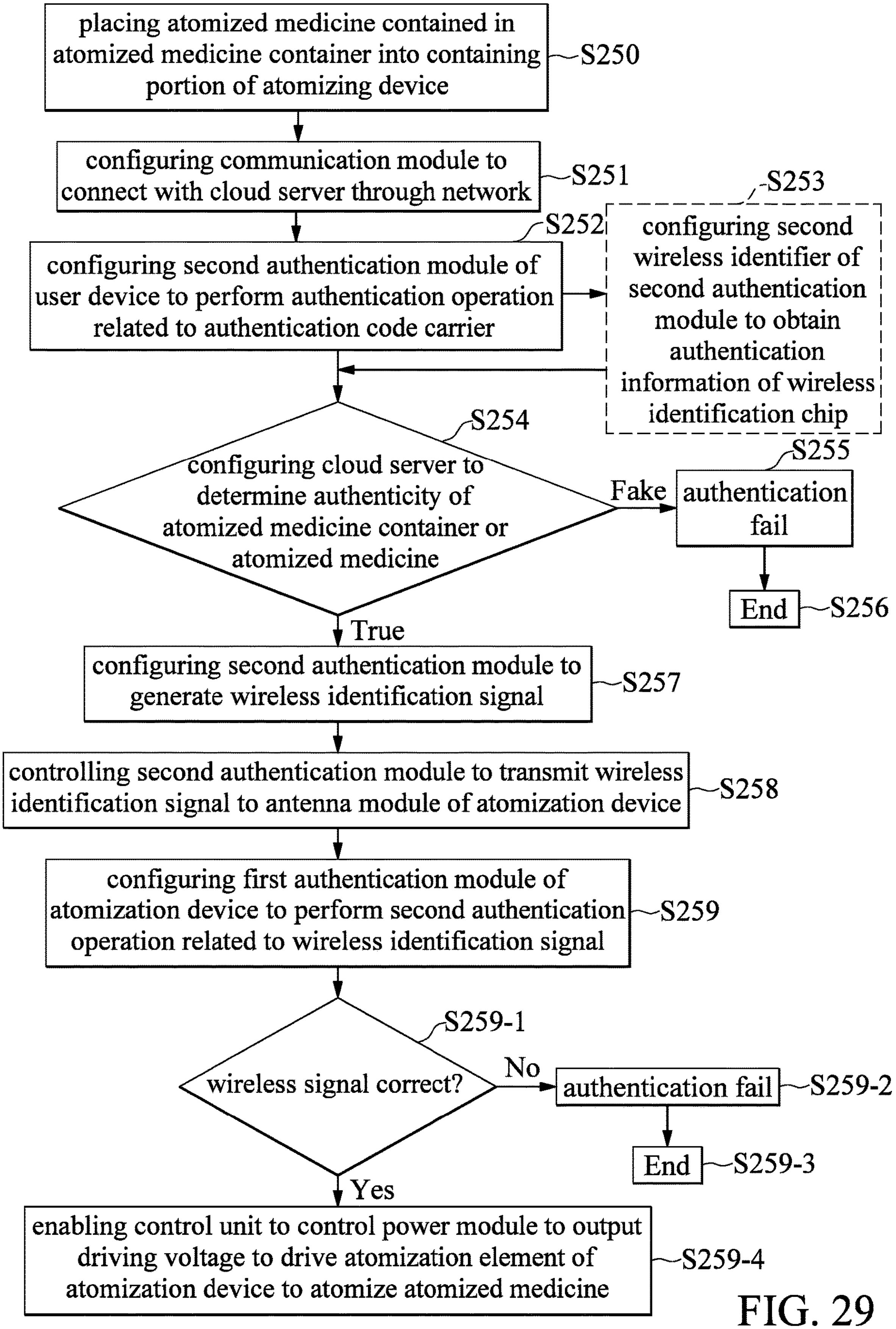

FIG. 29

S260 — configuring second authentication module to generate wireless identification signal S263 — transmitting radio frequency identification signal S261 — controlling second authentication module to transmit wireless identification signal to antenna module of atomization device S262 — transmitting Bluetooth identification signal S264 — configuring first authentication module of atomization device to perform second authentication operation related to wireless identification signal S265 — configuring first wireless identifier of first authentication module to receive wireless identification signal through antenna module S266 — wireless signal correct?

No → S267 — authentication fail → S268 — End

Yes ↓

S269 — enabling control unit to control power module to output driving voltage to drive atomization element of atomization device to atomize atomized medicine

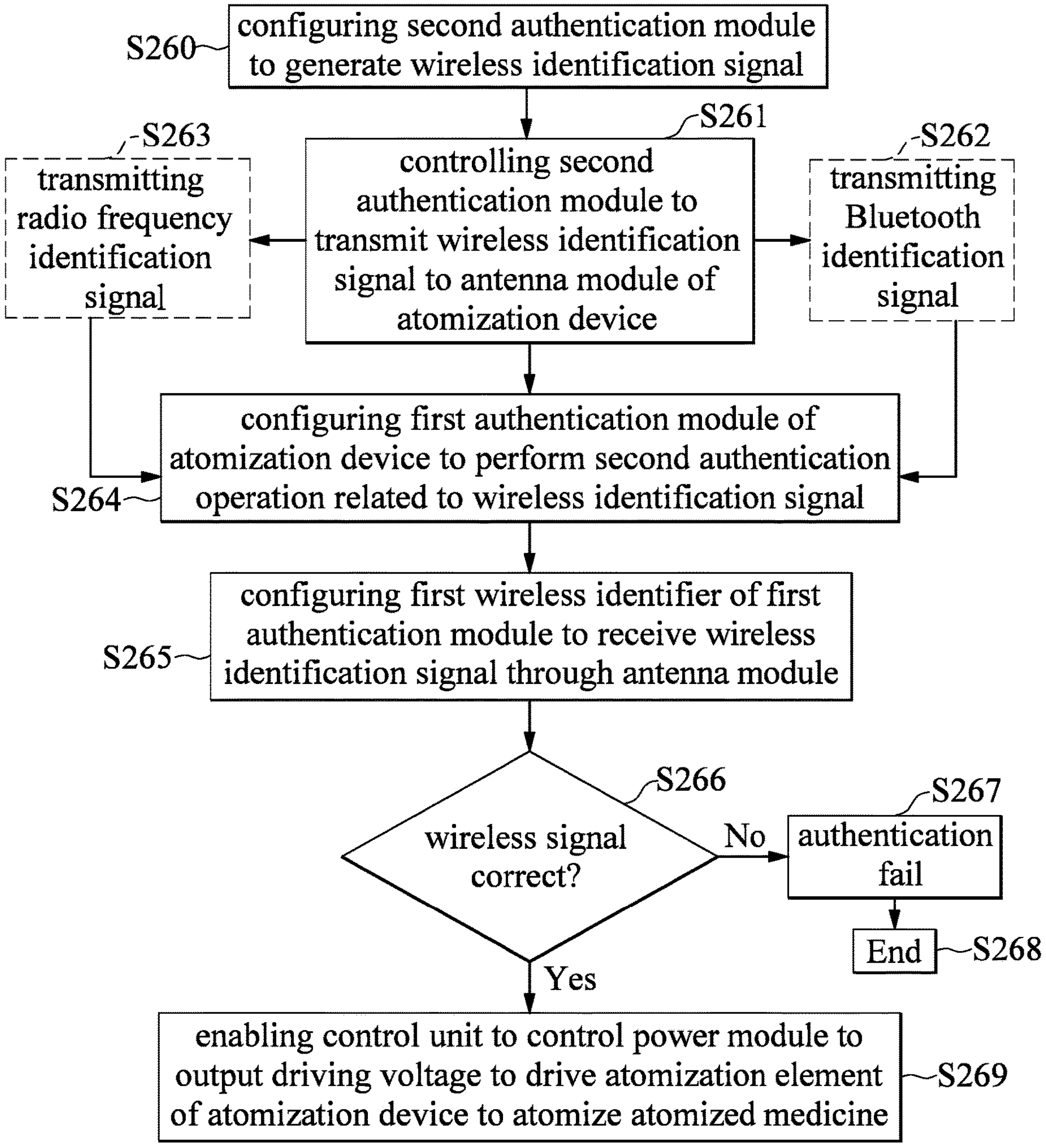

FIG. 30

ATOMIZATION SYSTEM HAVING DOUBLE AUTHENTICATION MECHANISM

CROSS-REFERENCE TO RELATED PATENT APPLICATION

This application claims the benefit of priority to Taiwan Patent Application No. 107108104, filed on Mar. 9, 2018. The entire content of the above identified application is incorporated herein by reference.

FIELD OF THE DISCLOSURE

The present invention relates to an atomization system and device, and in particular to an atomization system having a single authentication mechanism.

BACKGROUND OF THE DISCLOSURE

Medical nebulizers are mainly used for administration via the respiratory system. The nebulizer atomizes the liquid into fine particles with a certain particle size, and the medicament can be delivered from the patient's mouth and nose to enter the respiratory system of the patient through breathing and achieve the therapeutic purpose through the circulatory system.

However, due to the expensive prices of commercially available medicines, some unscrupulous businessmen are often attracted to counterfeit medicines. Due to the fact that product fraud is easy and illegal income is high, the forgery of these medicines has never stopped in the domestic and foreign markets.

For example, the main anti-counterfeiting methods for domestic and foreign pharmaceutical companies are to apply anti-counterfeit measures upon the label or the outside of packaging of pharmaceuticals in order to increase the difficulty of counterfeiting, and to try and prevent counterfeit medicine by increasing counterfeit costs, the measures including one-dimensional/two-dimensional barcode labels, laser tags, anti-counterfeit bottle caps, and anti-counterfeit ink printings. However, due to the easiness in forgery of these anti-counterfeiting measures, counterfeiters can quickly develop or procure workarounds therefor, so that counterfeit of such medicines cannot be completely eradicated.

Moreover, counterfeit medicines may also cause physical harm to consumers, resulting in loss of lives and properties. Therefore, there is a need for an atomization system and devices that can improve the existing anti-counterfeiting mechanisms and ensure that consumers do not use counterfeit medicines.

SUMMARY OF THE DISCLOSURE

The present disclosure is to provide an atomization system and device having a single authentication mechanism that can improve on the issues associated with the related art.

In order to solve the above technical problems, one technical solution adopted by the present disclosure is to provide an atomization system having a double authentication mechanism, which includes at least one atomized medicine container, a atomization device and a user device. The at least one atomized medicine container is associated with an authentication code carrier, and contains an atomized medicine. The atomization device includes an atomization module, a power module, a control unit, and a first communication module. The atomizing module has an accommodating portion and an atomization element. The accommodating portion is used for accommodating atomized medicine, and the atomization element is used for atomizing the atomized medicine when the atomized medicine is placed in the accommodating portion. The power module outputs the driving voltage to directly drive the atomization module. The control unit is connected to the power module, and the control unit is used to control the power module to output the driving voltage. The first communication module is connected to the control unit for transmitting and receiving signals. The user device includes a processor, a second communication module, and an authentication module. The second communication module is connected to the processor, configured to pair with the first communication module, and connected to the cloud server through the network. The authentication module is connected to the processor and configured to perform an authentication operation related to the authentication code carrier to determine the authenticity of at least one atomized medicine container or atomized medicine through the cloud server, and to generate an authentication result signal correspondingly. The authentication module is configured to determine whether to control the second communication module through the processor to transmit an authentication success signal to the first communication module according to the authentication result signal. When the first communication module receives the authentication success signal, the control unit is configured to control the power module to output the driving voltage according to the authentication success signal.

In order to solve the above technical problems, another one technical solution adopted by the present disclosure is to provide an atomization system having a double authentication mechanism, which includes at least one atomized medicine container, an atomization device and a user device. The at least one atomized medicine container is associated with an authentication code carrier, and contains an atomized medicine. The atomization device includes an atomization module, a power module, a control unit, and an antenna module. The atomizing module has an accommodating portion and an atomization element. The accommodating portion is used for accommodating atomized medicine, and the atomization element is used for atomizing the atomized medicine when the atomized medicine is placed in the accommodating portion. The power module outputs the driving voltage to directly drive the atomization module. The control unit is connected to the power module, and the control unit is used to control the power module to output the driving voltage. The antenna module is used for transmitting and receiving signals. The first authentication module respectively is connected to the control unit and the antenna module. The user device includes a processor, a communication module, and a second authentication module. The communication module is connected to the processor, and is connected to a cloud server through a network. The second authentication module is connected to the processor and configured to perform a first authentication operation related to the authentication code carrier to determine the authenticity of the at least one atomized medicine container or the atomized medicine through the cloud server, and to generate the authentication result signal correspondingly. The second authentication module is configured to determine whether to generate a wireless identification signal according to the authentication result signal. When the antenna module receives the wireless identification signal, the first authentication module is configured to perform a second authentication operation related to the wireless identification signal, and to further determine whether to enable the control unit to control the power module to output the driving voltage.

One of the advantages of the present disclosure is that the atomization system and device having a double authentication mechanism provided by the present disclosure may improve the anti-fake effect using the anti-counterfeit identification code and product history data through the technical solutions of "wireless identifier" and "wireless identification chip".

Yet another one of the advantages of the present disclosure is that the atomization system having the double authentication mechanism provided by the present disclosure may improve the convenience of authentication by obtaining the "authentication information" through the "authentication code input interface" and the "image capturing module".

Yet another one of the advantages of the present disclosure is that the atomization system having a double authentication mechanism provided by the present disclosure may improve the anti-fake effect using the anti-counterfeit identification code and product history data through the technical features of paring the "atomization device" and the "user device", configuring the user device to perform an authentication operation associated with the authentication code carrier, and determining the authenticity of the atomized medicine or the atomized medicine container through the cloud server.

Yet another one of the advantages of the present disclosure is that the atomization system having a double authentication mechanism provided by the present disclosure may ensure that the atomized medicine containers purchased by users have not been used and faked through the technical features of "cloud server performs the comparison operation in the password database" and instantly updating the password database by the supplier.

Yet another one of the advantages of the present disclosure is that the atomization system having a double authentication mechanism provided by the present disclosure may greatly increase the difficulty of counterfeiting the authentication code carrier through the technical features of the "double authentication mechanism provided by the user device" and the "independent authentication mechanism provided by the atomization device", so as to ensure the security of data transmission, such that the counterfeit goods are not able to be used by the atomization device even if they are sold in the market, and thus protecting the lives and property of consumers.

For a better understanding of the features and technical content of the present invention, reference should be made to the following detailed description and drawings of the present invention, however, the drawings are provided for the purpose of providing references and illustrations only, and are not intended to limit the present invention.

BRIEF DESCRIPTION OF THE DRAWINGS

FIG. 29 is a flowchart of an atomization method having an authentication mechanism according to a twenty-first embodiment of the present invention.

FIG. 30 is a flowchart of an authentication operation according to the twenty-second embodiment of the present invention.

DETAILED DESCRIPTION OF THE EXEMPLARY EMBODIMENTS

Figure 1:
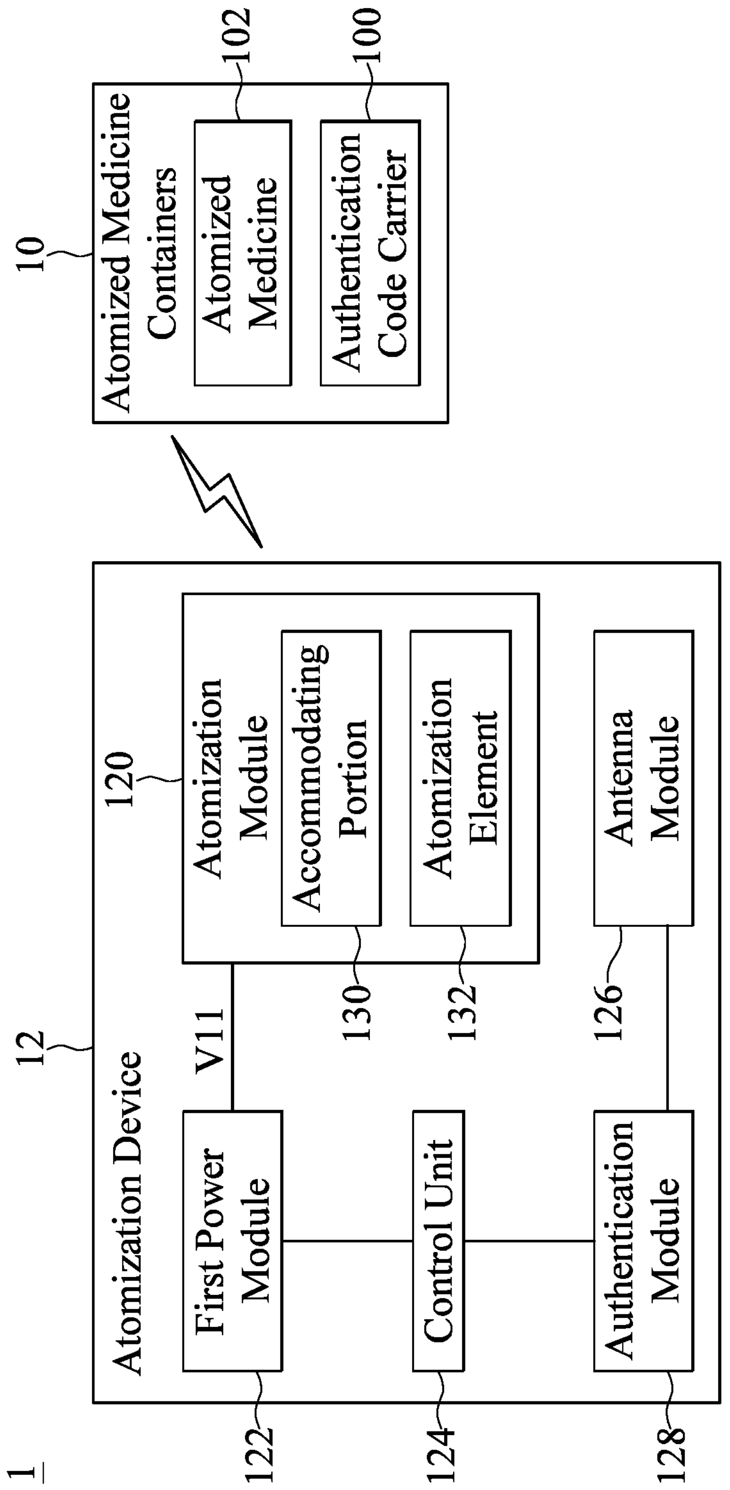
FIG. 1 is a block diagram of an atomization system with a single authentication mechanism according to a first embodiment of the present invention.

The following is embodiments of the present invention disclosed in relation to the "atomization system and method" through specific embodiments. Those skilled in the art can understand the advantages and effects of the present invention according to the contents disclosed in the present specification. The present invention may be implemented or applied through other different specific embodiments. The details in this specification may also be based on different viewpoints and applications, and various modifications and changes may be made without departing from the concept of the present invention. In addition, the drawings of the present invention are merely schematic illustrations and are not depicted by actual dimensions. The following embodiments will further describe related technical contents of the present invention in detail, but the disclosed contents are not intended to limit the scope of the present invention.

It will be understood that although the terms first, second, third, etc. may be used herein to describe various elements or signals, however, these elements or signals should not be limited by these terms. These terms are mainly used to distinguish one element from another element, or one signal from another signal. In addition, the term "or" as used herein, as appropriate, may include combinations of any one or more of the associated listed items.

To clarify, in some cases, the techniques of the present invention may be presented as including separate functional blocks that include functional blocks, including devices, device elements, steps or routes in a method implemented in software, or a combination of hardware and software.

In some embodiments, computer-readable storage devices, media, and memory may include cables or wireless signals containing bitstreams, etc. However, when mentioned, non-transitory computer-readable storage media explicitly excludes media such as energy, carrier signals, electromagnetic waves, and signals themselves.

The method according to the above-described embodiments may be implemented by using computer-executed instructions stored in or otherwise accessible from a computer-readable medium. Such instructions may include, for example, instructions and data that cause or otherwise configure a general purpose computer, a special purpose computer, or a special purpose processing device to perform a certain function or set of functions. Parts of the computer resources used can be accessed via the Internet. The computer executable instructions may be, for example, binary, intermediate format instructions such as assembly language, firmware, or source code. Examples of computer-readable media that may be used to store instructions, information used, and/or information created during a method in accordance with the described embodiments include a magnetic or optical disk, flash memory, non-volatile memory USB memory devices, networked storage devices, and more.

Devices for implementing the methods provided by the present disclosure may include hardware, firmware, and/or software, and may take any of a variety of configurations. Typical examples of such configurations include laptops, smart phones, small personal computers, personal digital assistants, and the like. The functions described herein may also be implemented in peripheral devices or built-in cards. By way of further example, such functions may also be implemented on circuit boards executing different processes on different chips or on a single device.

The instructions, media for communicating such instructions, computing resources for performing the same or other structures for supporting such computing resources are used for providing means of the functionality described in this disclosure.

First Embodiment

Reference is now made to FIG. 1, which is a block diagram of an atomization system with a single authentication mechanism according to a first embodiment of the present invention. As shown, the atomization system 1 includes an atomized medicine container 10 and an atomizing device 12. The atomization medicine container 10 has an authentication code carrier 100, and the atomization medicine container 10 accommodates the atomized medicine 102. In general, the atomized medicine container 10 may be a bottle container with a bottle rim, and the authentication code carrier 100 may be an electronic tag provided on the bottle cap to be used separately from the bottle container, but the present invention is not limited thereto, and the authentication code carrier 100 may also be an electronic tag detachably disposed outside the bottle container.

Referring to FIG. 1, the atomization device 12 includes an atomization module 120, a first power module 122, a control unit 124, an antenna module 126, and an authentication module 128. The atomization module 120 has an accommodating portion 130 and an atomization element 132. The accommodating portion 130 can be used for being loaded with the aforesaid atomized medicine 102, and the atomization element 132 is used for atomizing the atomizing drug 102 when it is placed in the accommodating portion 130. In addition, the control unit 124 is electrically connected to the first power module 122, and the first power module 122 is electrically connected to the atomization module 120.

In practice, the control unit 124 controls the first power module 122 to output the first driving voltage V11. The first driving voltage V11 output by the first power module 122 is mainly used to directly drive the atomization module 120. In detail, the control unit 124 may be, for example, a control chip, a micro control chip, or a PWM control chip. The present embodiment does not limit the aspect of the control unit 124. The control unit 124 has a plurality of built-in ports that can output pulse modulation signals, and can provide control signals with different frequencies and duty cycles. The frequency adjustment range may be, for example, 10 Hz~1 MHz, and the duty cycle adjustment range may be, for example 10% to 90%. In practice, the control unit 124 may output one or more control signals. The control signal is used to control the operation of the first power module 122.

The first power module 122 may be, for example, a driving circuit including one or more switches, one or more inductors, one or more capacitors and diodes. The present embodiment does not limit the aspect of the first power module 122. The first power module 122 is configured to receive the control signal output by the control unit 124. In practice, the first power module 122 provides the atomization module 120 with the first driving voltage V11 that oscillates at the output frequency according to the control signal. The first driving voltage V11 may be, for example, a pulsing DC voltage. The waveform of the first driving voltage V11 may be, for example, a sine wave, a triangular wave, or a square wave.

In the present invention, in order to achieve wireless authentication, the atomization device 12 is further equipped with an antenna module 126 for transmitting and receiving signals. At the same time, the atomization device 12 also has an authentication module 128 connected to the control unit 124 and the antenna module 126, respectively, the authentication module 128 is configured to perform an authentication operation related to the authentication code carrier 100 to determine an authenticity of the atomized medicine container 10 or the atomized medicine 102, and the authentication result signal S11 is generated correspondingly. In this case, the control unit 124 is configured to control the first power module 122 to output the first driving voltage V11 according to the authentication result signal S11.

Specifically, the authentication operation between the authentication module 128 and the authentication code carrier 100 may utilize the radio frequency identification (RFID), which is a non-contact, automatic identification technology of the radio frequency identification system, and is mainly composed of radio frequency tag (RFID tag), reader or barcode reader and related application system.

The tag structure of the RFID is formed by adding the coil on the housing with a chip, and the RFID tag receives or transmits the information of the chip by receiving the energy of the reader through the metal wire of the coil, or through the power of the coil, so as to achieve the communication between the wireless RFID tag and the reader.

Radio frequency identification tags may also be substantially classified as an active type and a passive type. The active type of the RFID tags may be powered by an external power supply device (e.g., battery), and the passive type of the wireless RFID tags may be directly powered by the radio wave transmitted by an external reading/writing device.

Figure 2A:
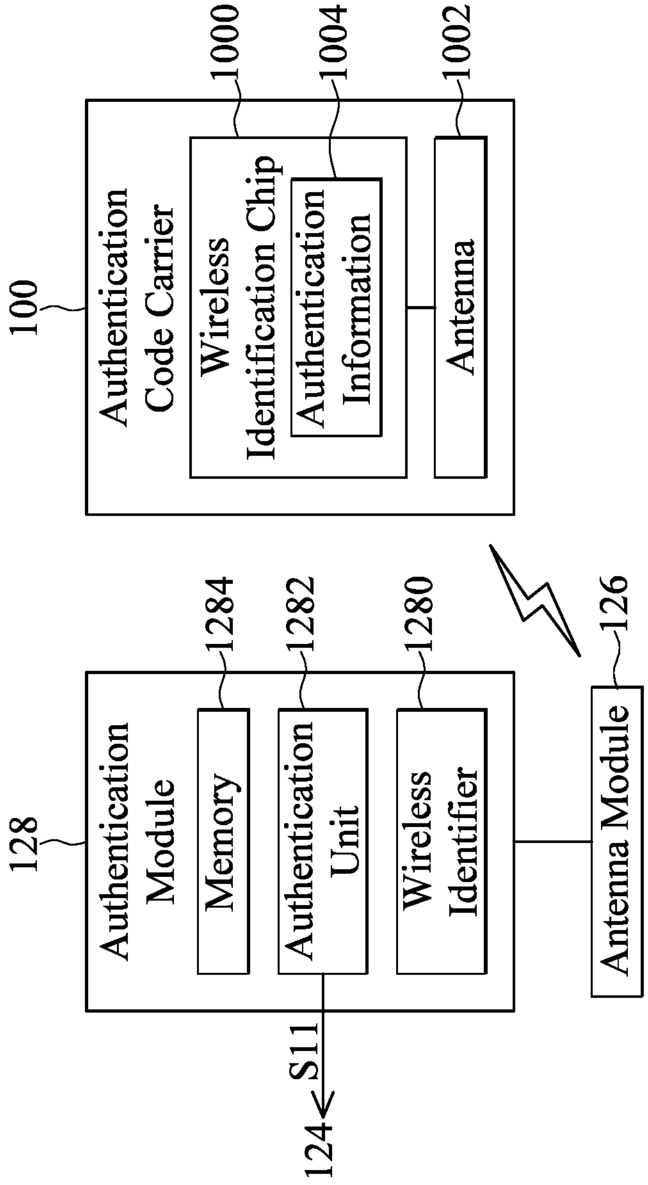
FIG. 2A is a block diagram of the authentication module, the antenna module, and the authentication code carrier according to the first embodiment of the present invention.
Figure 2B:
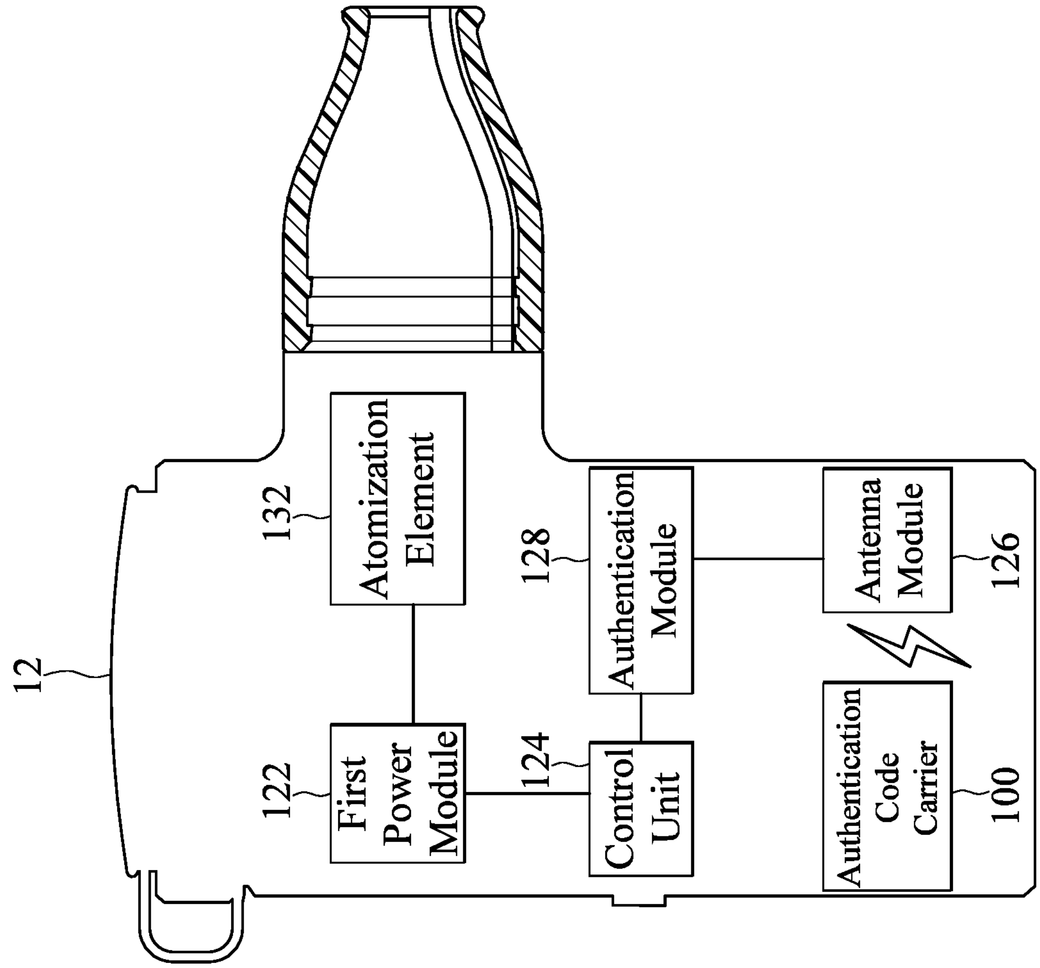
FIG. 2B is a functional diagram of the atomization system with the single authentication mechanism according to the first embodiment of the present invention.
Figure 2C:
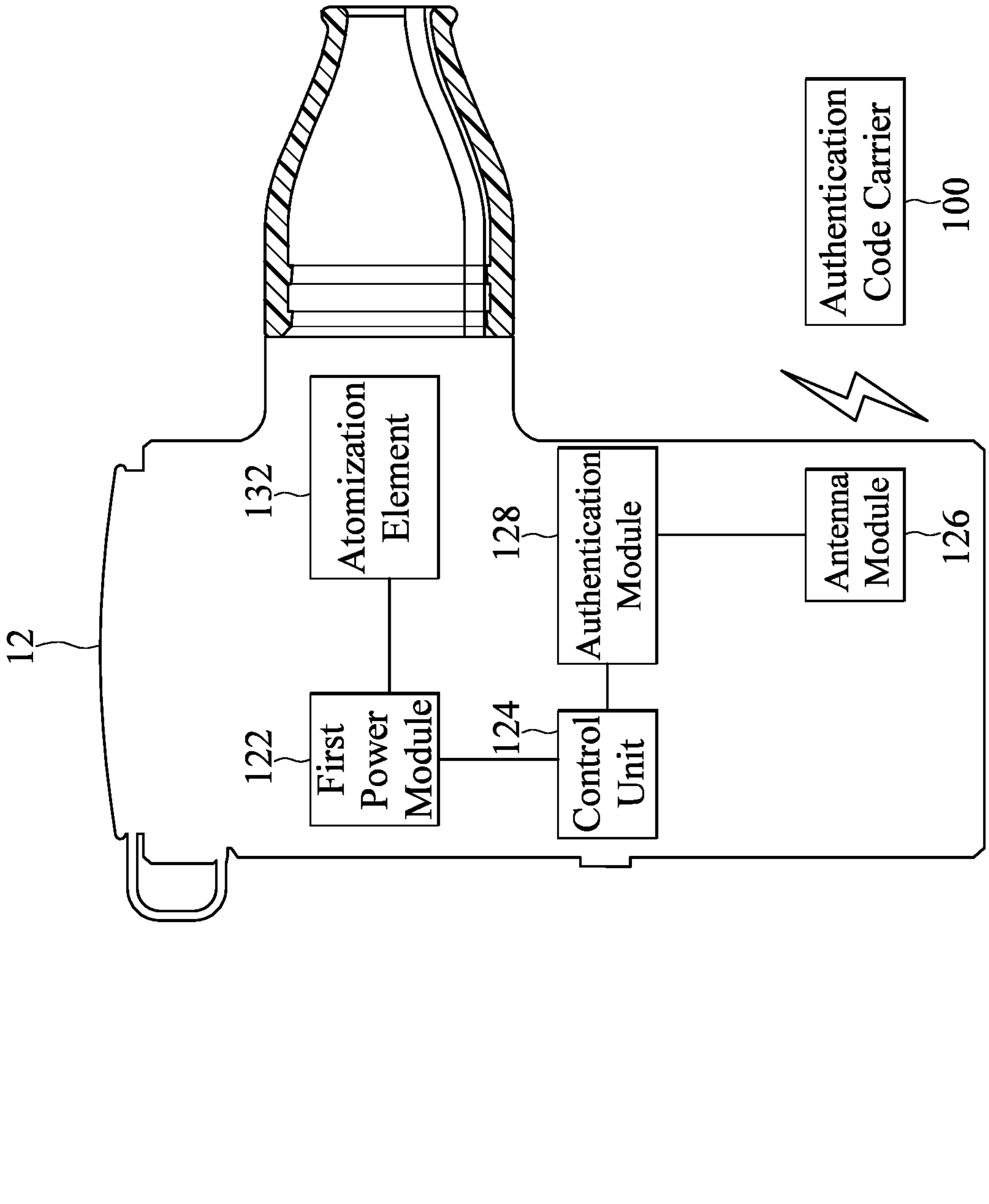
FIG. 2C is another functional diagram of the atomization system with the single authentication mechanism according to the first embodiment of the present invention.

Please further refer to FIG. 2A to FIG. 2D. FIG. 2A is a block diagram of the authentication module, the antenna module, and the authentication code carrier according to the first embodiment of the present invention, FIG. 2B is a functional diagram of the atomization system with the single authentication mechanism according to the first embodiment of the present invention, and FIG. 2C is another functional diagram of the atomization system with the single authentication mechanism according to the first embodiment of the present invention. As shown in the figures, the authentication module 128 includes a wireless identifier 1280, an authentication unit 1282, and a memory 1284, the authentication code carrier 100 includes a wireless identification chip 1000 and an antenna 1002 connected thereto. In this example, the authentication operation between the authentication module 128 and the authentication code carrier 100 is mainly based on the passive RFID technology, which is directly powered by the wireless identifier 1280 through the radio waves transmitted by the antenna module 126 to the radio frequency identification tag, that is, the wireless identification chip 1000 itself, and the wireless identification chip 1000 further has authentication information 1004 written in advance. Here, the authentication information 1004 may be an anti-counterfeiting identification code having a specific coding sequence and product history data. In practice, the wireless identifier 1280 may be utilized to read the authentication information 1004 previously written in the wireless identification chip 1000 so as to effect anti-fake improvements using the anti-counterfeit identification code and product history data.

In addition, the authentication unit 1282 may further process the read anti-counterfeit identification code with a specific coding sequence, and perform a specific authentication algorithm stored in the memory 1284 to perform decryption to confirm the authenticity of the authentication code carrier 100 having the authentication information 1004. Another example of the processing operation performed by the authentication unit 1282 may compare a part or all of the authentication information 1004 with the data stored in the memory 1284 to confirm authenticity of the authentication code carrier 100. If the authenticating unit 1282 determines that the authenticating code carrier 100 is true, it can be known that the corresponding atomized medicine container 10 is not forged, such that the user can use it with confidence.

After the above authentication operation, the authentication module 128 may be configured to generate the authentication result signal S11 correspondingly, and the control unit 124 may be further configured to determine whether to control the first power module 122 to output the first driving voltage V11 according to the authentication result signal S11. Specifically, if the authentication unit 1282 determines that the authentication code carrier 100 is true, the corresponding authentication result signal S11 can enable the control unit 124 to control the first power module 122 to output the first driving voltage V11 to drive the atomization element 132 of the atomization module 120, and to further atomize the atomized medicine 102. On the other hand, if the authentication unit 1282 determines that the authentication code carrier 100 is fake, or the authentication unit 1282 cannot recognize the authentication information 1004, then the corresponding output authentication result signal S11 may disable the control unit 124.

For practical applications, referring to FIG. 2B, the authentication code carrier 100 can be placed inside the atomization device 12 to perform authentication through the antenna module 126. On the other hand, referring to FIG. 2C, the authentication code carrier 100 may also be authenticated by the antenna module 126 outside the atomization device 12, and is not limited to these two configurations. Those skilled in the arts may make various possible modifications to the housing of the atomization device 12 without departing from the scope of the present invention, and the wireless sensing mechanism also increases the flexibility of the application.

Furthermore, the number of the atomized medicine container 10 may be plural in the present embodiment, and the plurality of atomized medicine containers 10 are associated with the authentication code carrier 100 in a many-to-one manner. Specifically, the authentication code carrier 100 may be attached in the form of a card to a box containing a plurality of atomized medicine containers 10, and the authentication code carrier 100 further includes usage limit information 1005.

Therefore, in the foregoing authentication operation, the authentication unit 1282 of the authentication module 128 may be further configured to determine whether the usage limit information 1005 reaches a predetermined limit amount. For example, if the authentication unit 1282 determines that the authentication code carrier 100 is true, the authentication unit 1282 may further obtain the usage limit information 1005, which defines the usage limit of the authentication code carrier 100, and the usage number corresponds to the number of atomized medicine containers 10 and decreases as the number of usage increases. In this embodiment, the predetermined limit amount may be defined as 0, that is, the authentication unit 1282 of the authentication module 128 determines whether the usage limit information 1005 has reached 0, and if yes, it represents that the user has exceeded the limit for times of usage, and thus the corresponding authentication result signal S11 is generated to disable the control unit 124.

In other words, if the authentication unit 1282 of the authentication module 128 determines that the usage limit information 1005 has not reached 0, the authentication module 128 is then configured to update the usage limit information 1005, for example, to reduce the number of uses of the authentication code carrier 100 by one, and the authentication result signal S11 is generated to enable the control unit 124 correspondingly.

Figure 2D:
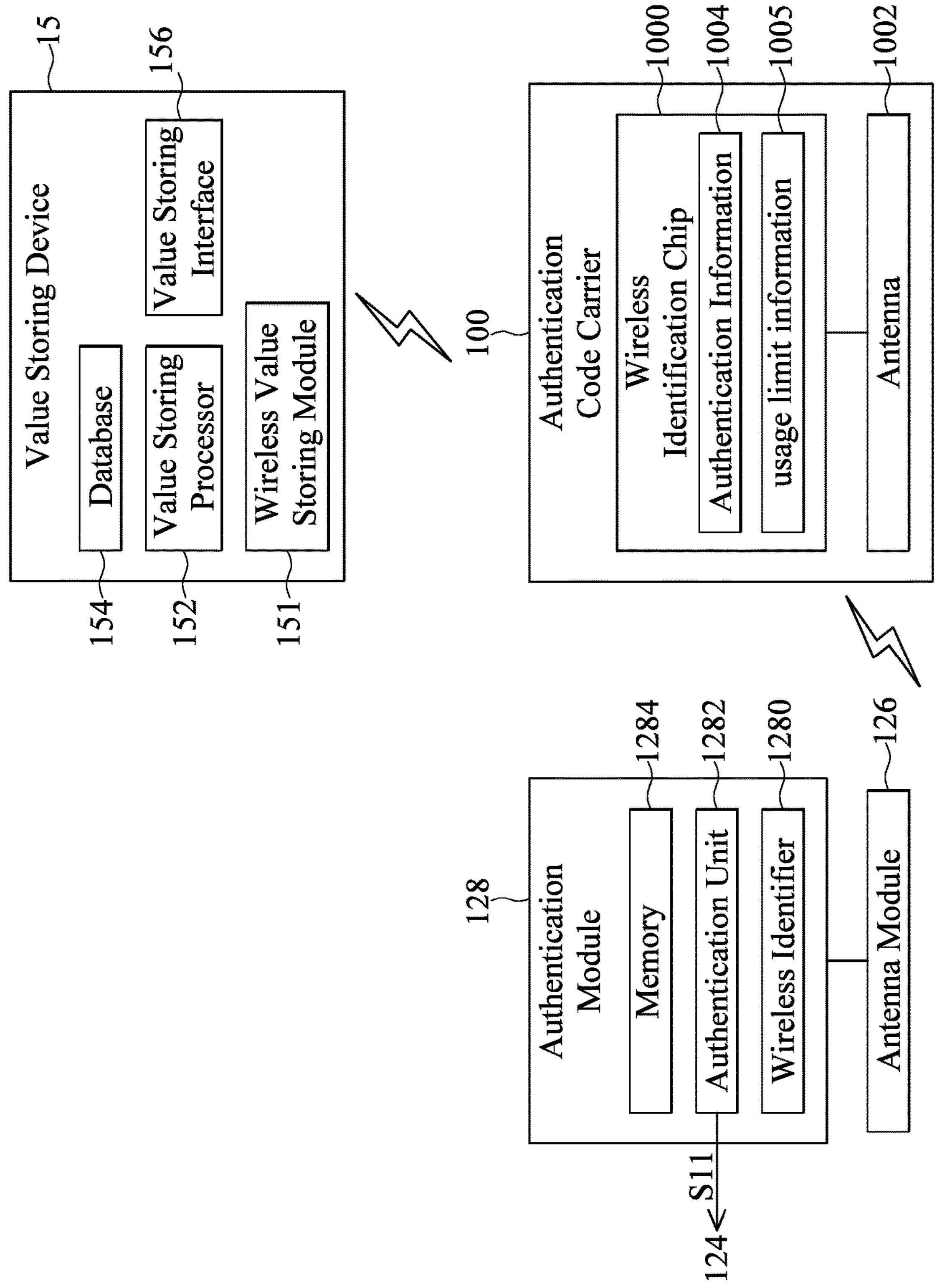
FIG. 2D is a block diagram of the value storing device and the authentication code carrier according to a first embodiment of the present invention.

Referring to FIG. 2D, FIG. 2D is a block diagram of the value storing device and the authentication code carrier according to a first embodiment of the present invention. As shown, the atomization system 1 having the single authentication mechanism further includes a value storing device 15. The value storing device 15 includes a wireless value storing module 151, a value storing processor 152, a database 154, and a value storing interface 156.

In detail, the user may obtain the authentication code carrier 100 corresponding to one or more atomized medicine containers 10 when the atomized medicine is purchased. The usage limit information 1005 of the authentication code carrier 100 may be preset to 0, and when the user completes the purchase at the pharmacy counter, staffs of the pharmacy may operate the value storing interface 156 to update the usage limit information 1005 by the wireless module 151, for example, configuring the value storing processor 152 to query or update the database 154 according to the purchased barcode, and to update the usage limit information 1005 preset to 0 to the purchased quantity of the atomization medicine containers 10.

It is worth mentioning that the authentication code carrier 100 can be disposable or reused, and after the usage limit information 1005 reaches 0, the user may directly use the same authentication code carrier 100 while purchasing a new medicine container 10 and updating the usage limit information 1005.

With the above configuration, when the user purchases a specific number of atomized medicine containers, it can ensure that the usage limit information corresponds to the number of atomized medicine containers, and the reliability of the authentication may be further increased.

Second Embodiment

Figure 3:
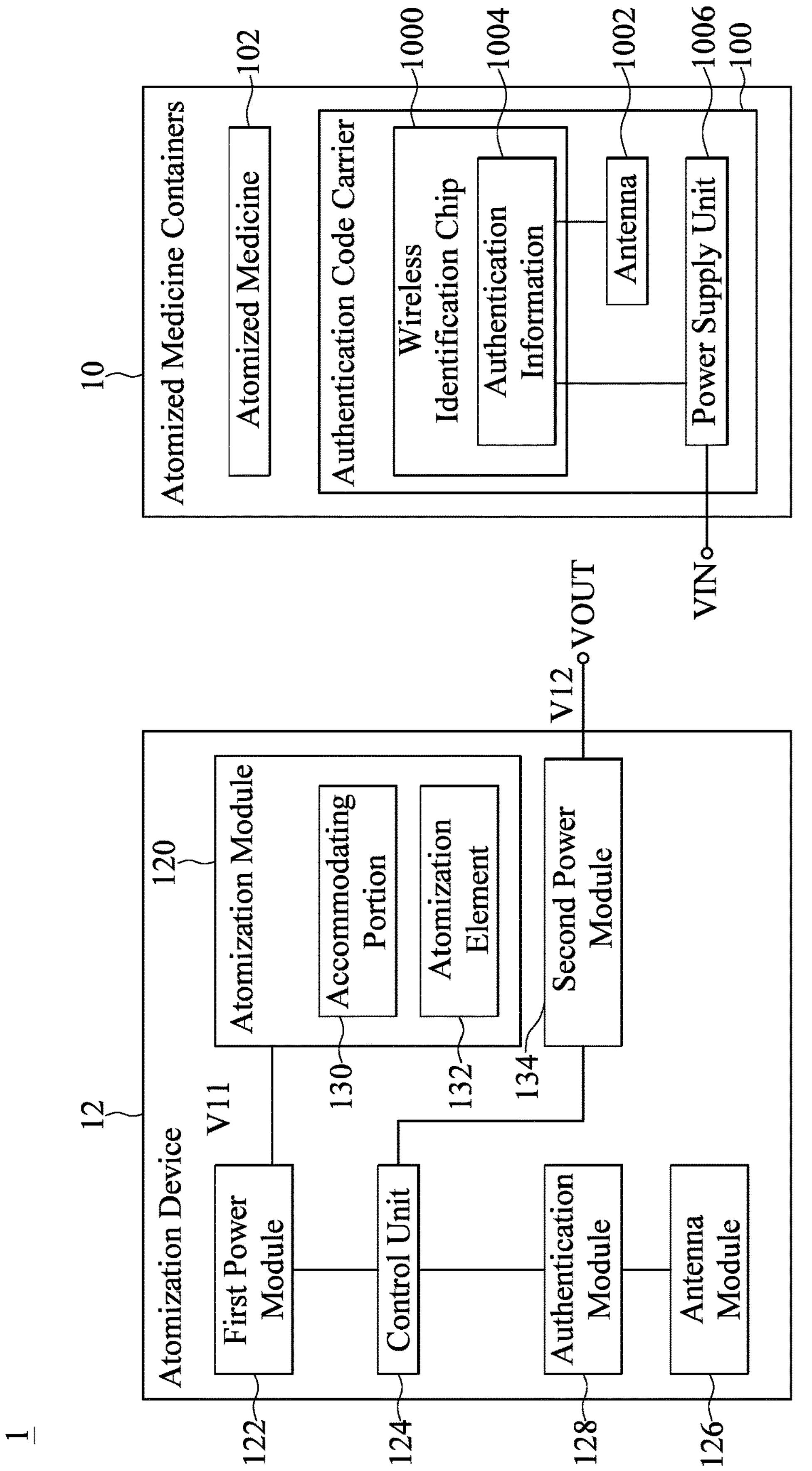
FIG. 3 is a block diagram of an atomization system with a single authentication mechanism according to a second embodiment of the present invention.

Reference is now made to FIG. 3, which is a block diagram of an atomization system with a single authentication mechanism according to a second embodiment of the present invention. In this embodiment, the reference numerals similar to the first embodiment designate similar elements and will not be further described. As shown in the figure, the second embodiment is different from the first embodiment in that the atomization system 1 further includes a second power module 134 electrically connected to the control unit 124 for outputting a second driving voltage V12. The control unit 124 may output one or more control signals for controlling the operation of the second power module 134.

In addition, the atomization device 12 further includes a power supply portion VOUT connected to the second power module 134, and the authentication code carrier 100 further includes a power receiving portion VIN connected to the wireless identification chip 1000. The second power module 134 is configured to output the second driving voltage V12 to enable the wireless identification chip 1000 when the power supply portion VOUT is electrically connected to the power receiving portion VIN.

Specifically, the present embodiment mainly utilizes an active type of wireless identification technology. In addition to the active type of radio frequency identification technology mentioned above, the ISM (Industrial Scientific Medical) band radio frequency identification technology such as Bluetooth wireless identification technology may be employed, and the radio frequency identification may be performed in the 2.4 GHz Industrial Scientific Medical band (ISM Band). What the two configurations have in common is that both of them need to power the wireless identification chip to transmit the corresponding wireless signal through the antenna, and therefore are applicable to the present invention.

Figure 4:
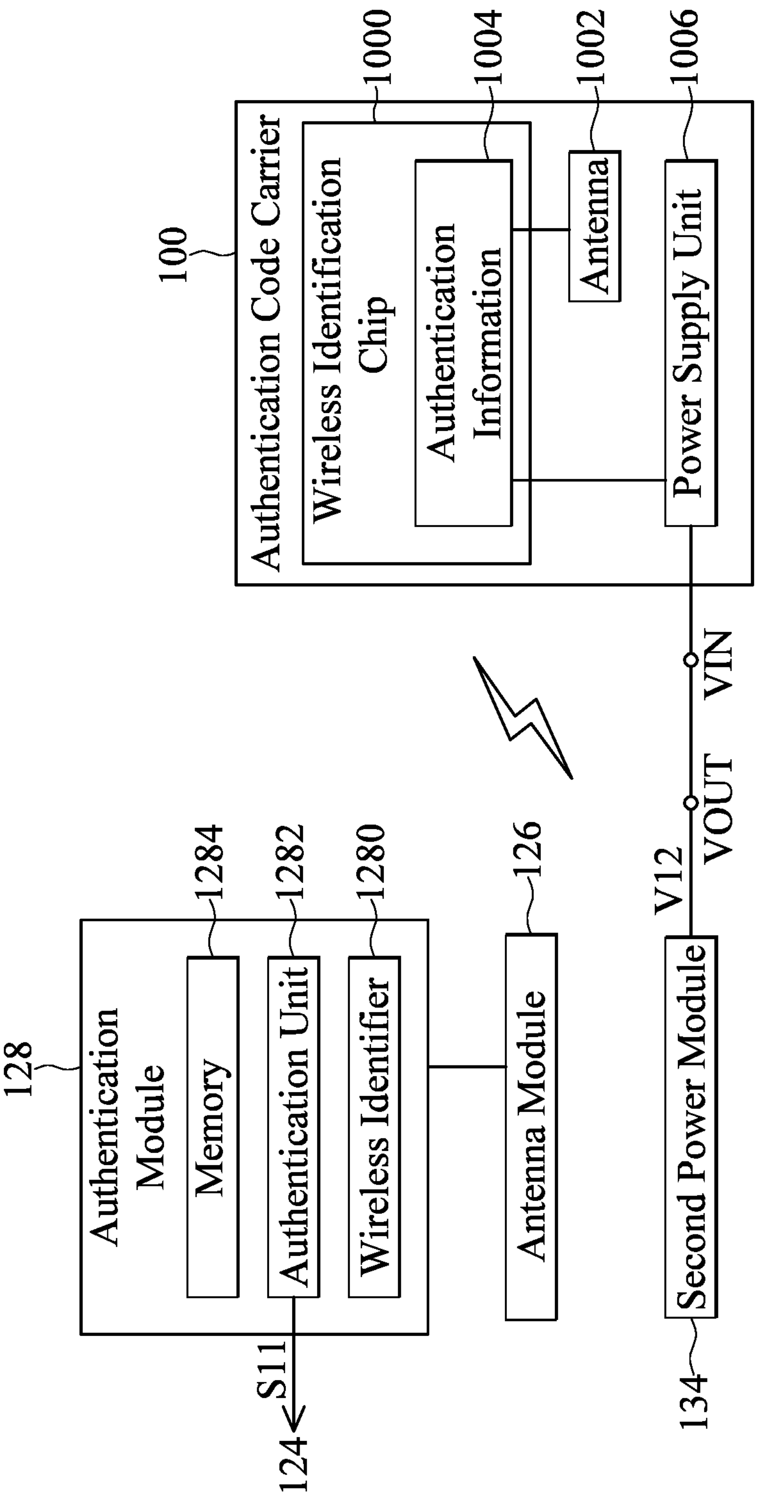
FIG. 4 is a block diagram of a second power module, an authentication module, an antenna module, and an authentication code carrier according to a second embodiment of the present invention.

Reference is now made to FIG. 4, which is a block diagram of a second power module, an authentication module, an antenna module, and an authentication code carrier according to a second embodiment of the present invention.

As shown in the figures, the authentication module 128 includes a wireless identifier 1280, an authentication unit 1282, and a memory 1284, the authentication code carrier 100 includes a wireless identification chip 1000, an antenna 1002 connected to the wireless identification chip 1000 and a power supply unit 1006. In this example, the authentication operation between the authentication module 128 and the authentication code carrier 100 is mainly based on the active type of the wireless identification technology, and it may use the active type of the wireless RFID technology or the ISM (Industrial Scientific Medical) band radio frequency identification technology such as Bluetooth wireless identification technology, and the radio frequency identification may be performed in the 2.4 GHz Industrial Scientific Medical band (ISM Band). The power supply unit 1006 has a power receiving terminal VIN, which receives a second driving voltage V12 supplied from the power supply terminal VOUT of the second power module 134. The power supply unit 1006 has a plurality of wires, resistors, or capacitors to assign the power to the antenna 1002 and the wireless identification chip 1000 in an appropriate manner.

The wireless identification chip 1000 has authentication information 1004 written in advance. Here, the authentication information 1004 may be an anti-counterfeiting identification code having a specific coding sequence and product history data. In practice, the authentication information 1004 previously written in the wireless identification chip 1000 may be transmitted to the wireless identifier 1280 by the wireless identification chip 1000 with the wireless radio frequency signals or Bluetooth identification signals, so as to effect anti-fake improvements using the anti-counterfeit identification code and product history data.

Functions of the authentication module 128 and authentication unit 1282 may be implemented by using one or more processors. The processor may be a programmable unit, such as a microprocessor, microcontroller, digital signal processor (DSP) chip, a field programmable gate array (field-programmable gate array; FPGA) and the like. Functions of the processor may also be implemented by one or several electronic devices or ICs. In other words, the functions performed by the processor may be implemented in a hardware domain or a software domain or a combination of the hardware domain and the software domain.

In addition, the authentication unit 1282 may further process the received anti-counterfeit identification code with a specific coding sequence, and perform a specific authentication algorithm stored in the memory 1284 for decryption, so as to confirm the authenticity of the authentication code carrier 100 having the authentication information 1004. Another example of the processing operation performed by the authentication unit 1282 may compare a part or all of the authentication information 1004 with the data stored in the memory 1284 to confirm authenticity of the authentication code carrier 100. If the authenticating unit 1282 determines that the authenticating code carrier 100 is true, it can be known that the corresponding atomized medicine container 10 is not forged, such that the user can use it with confidence.

After the above authentication operation, the authentication module 128 may be configured to generate the authentication result signal S11 correspondingly, and the control unit 124 may be further configured to determine whether to control the first power module 122 to output the first driving voltage V11 according to the authentication result signal S11. Specifically, if the authentication unit 1282 determines that the authentication code carrier 100 is true, the corresponding authentication result signal S11 can enable the control unit 124 to control the first power module 122 to output the first driving voltage V11 to drive the atomization element 132 of the atomization module 120, and to further atomize the atomized medicine 102. On the other hand, if the authentication unit 1282 determines that the authentication code carrier 100 is fake, or the authentication unit 1282 cannot recognize the authentication information 1004, then the correspondingly output authentication result signal S11 may disable the control unit 124.

Combining the second power module 134 provided in the present embodiment with the authentication code carrier 100 having the specific authentication information 1004, the atomized medicine container 10 may be prevented from being forged, and the security and anti-counterfeiting capabilities thereof can be further improved.

Figure 5:
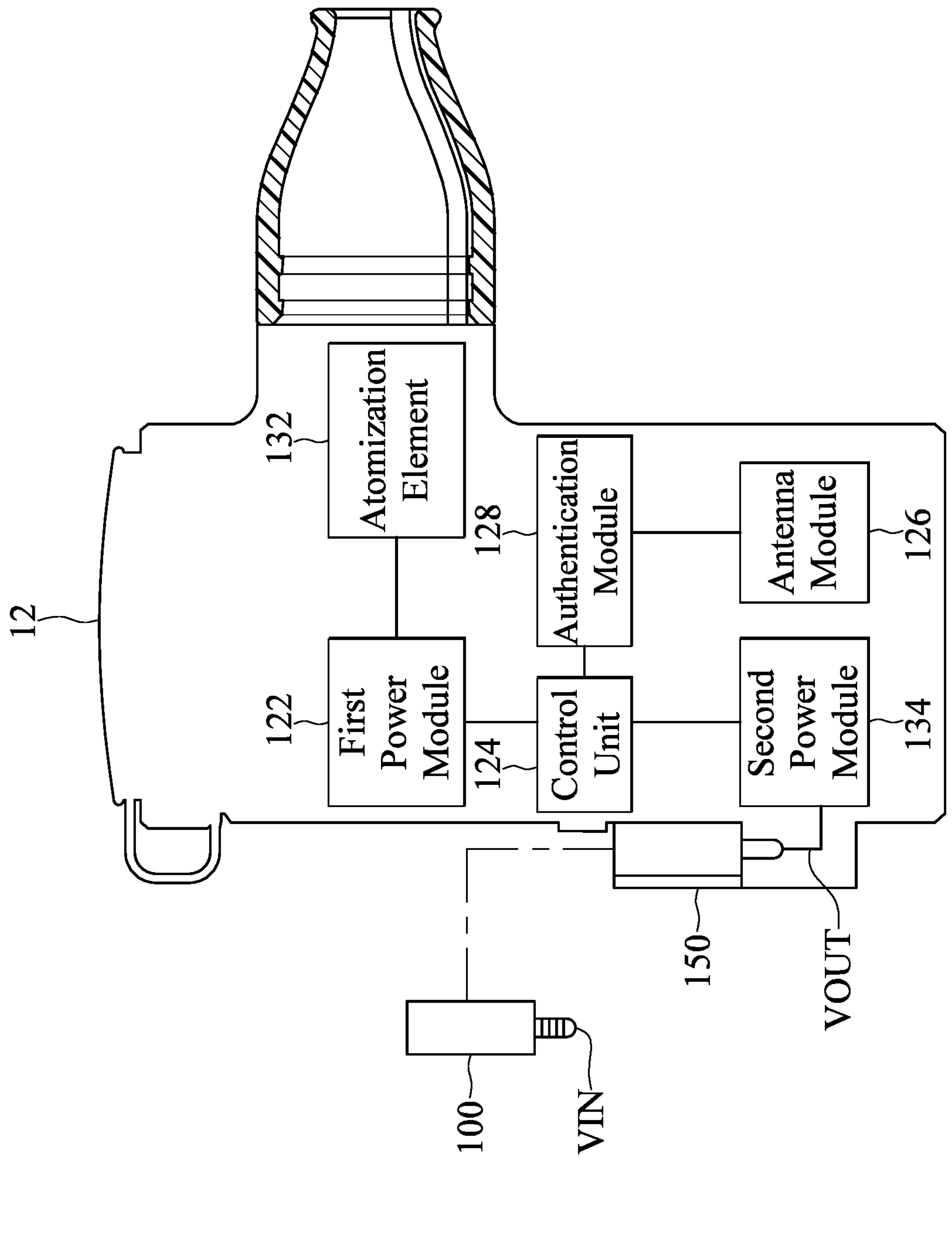
FIG. 5 is a functional diagram of an atomization system with a single authentication mechanism according to a second embodiment of the present invention.

Reference is now made to FIG. 5, which is a functional diagram of an atomization system with a single authentication mechanism according to a second embodiment of the present invention. As shown, the receiving portion VIN of the authentication code carrier 100 may be a connector with a specific standard, and the atomization device 12 may be further provided with an authentication code carrier accommodating portion 150 at the position where the power supply portion VOUT is disposed. After the power receiving terminal VIN is connected to the power supply terminal VOUT, appropriate supporting forces may be provided to stabilize the authentication code carrier 100, and the authentication code carrier accommodating portion 150 may also be disposed at the outside of the atomization device 12 corresponding to the antenna module 126, which not only provides convenience for the user, but also ensures that the wireless identifier 1280 may be successfully sensed with the wireless identification chip 1000.

Third Embodiment

Figure 6:
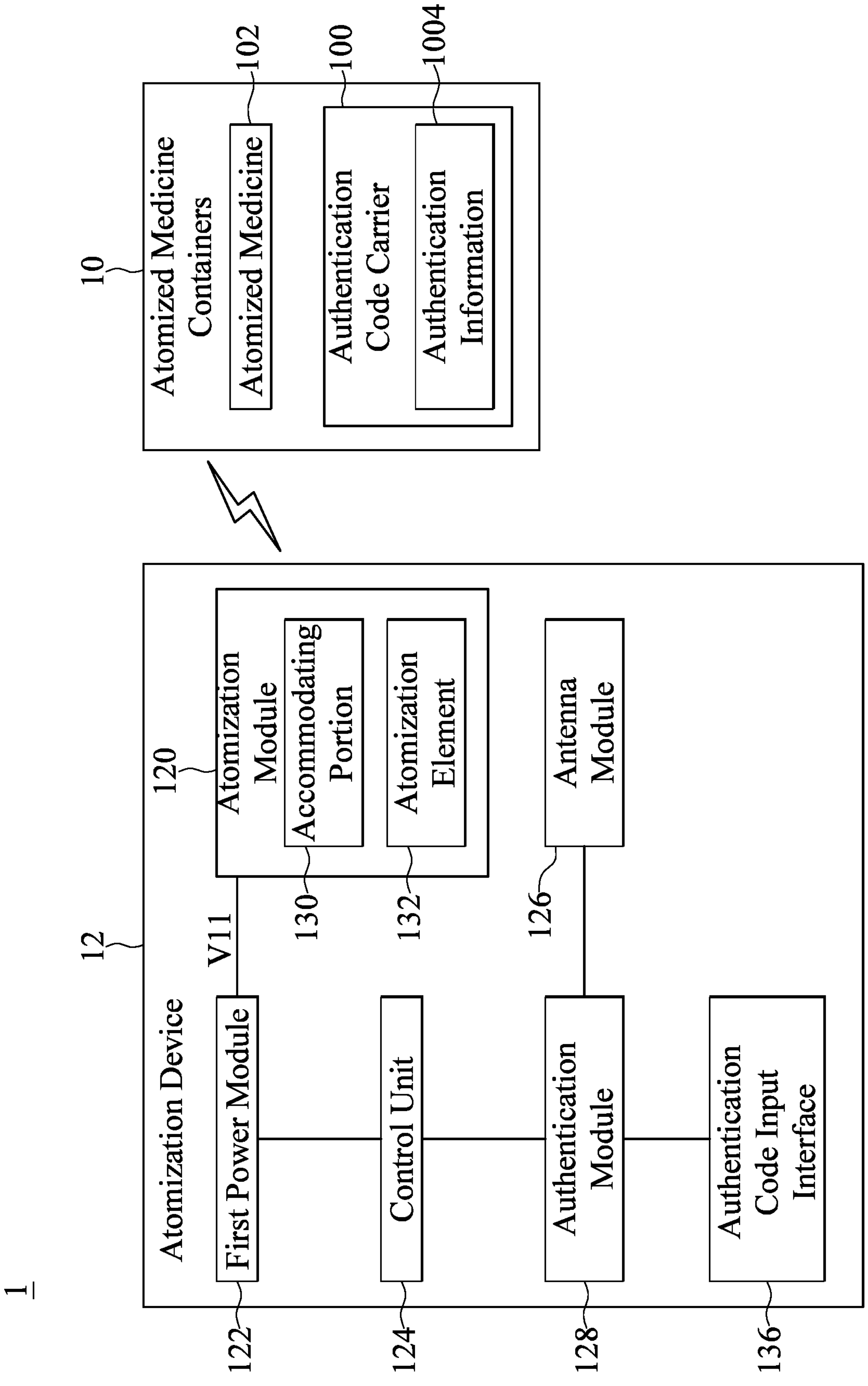
FIG. 6 is a block diagram of an atomization system with a single authentication mechanism according to a third embodiment of the present invention.
Figure 7:
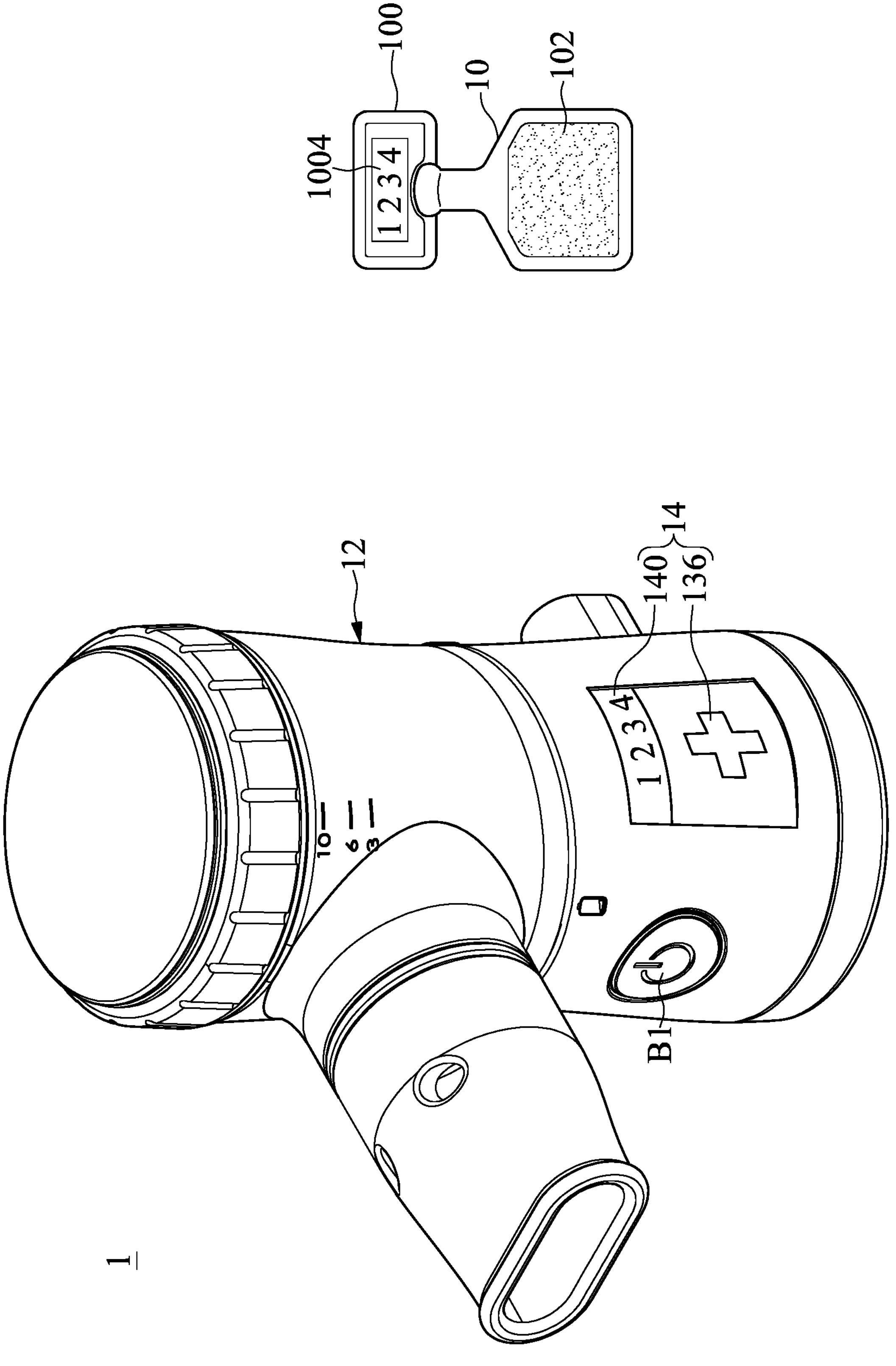
FIG. 7 is a perspective view of an atomization system with a single authentication mechanism according to a third embodiment of the present invention.

Reference is now made to FIGS. 6 and 7, which are a block diagram and a perspective view of an atomization system with a single authentication mechanism according to a third embodiment of the present invention, respectively. As shown in the figures, in the atomization system 1 with a single authentication mechanism in the present embodiment, the atomization device 12 further includes an authentication code input interface 136 connected with the authentication module 128, which is configured for the user to input the authentication information 1004 of the authentication code carrier 100.

Specifically, the atomization device 12 is generally configured with a user interface 14, and the user interface 14 may include the authentication code input interface 136 mentioned above and the display screen 140. The authentication code input interface 136 may utilize physical keys or virtual keys displayed on the display screen 140, and the present embodiment does not limit the implementation manners of the interfaces. For example, the atomization device 12 may be configured with a power key B1 to control the atomization device 12 to be turned on or off. The authentication code input interface 136 may include numeric keys labeled with numbers 1-9, cancel, back, confirm or cross key. The user can select the authentication code to be input through the cross key and confirm the input via the confirmation key.

More specifically, the authentication code carrier 100 may be directly printed with the authentication information 1004, for example, an authentication code having a specific sequence code, and may be printed at a position where the authentication code carrier 100 is disposed, for example, inside or outside of the bottle cap or the bottle body of the atomized medicine container 10. The user can directly input the authentication code through the authentication code input interface 136, which can be correspondingly displayed on the display screen 140 for the user to confirm.

After the user inputs the authentication information 1004, the authentication module 128 may be further configured to determine the authenticity of the atomized medicine container 10 or the atomization medicine 102 according to the authentication information 1004, and to generate an authentication result signal S11 correspondingly. In addition, the authentication unit 1282 may further process the anti-counterfeit identification code with a specific coding sequence input by the user, and perform a specific authentication algorithm stored in the memory 1284 to perform decryption to confirm the authenticity of the authentication code carrier 100 having the authentication information 1004. Another example of the processing operation performed by the authentication unit 1282 may compare a part or all of the authentication information 1004 with the data stored in the memory 1284 to confirm authenticity of the authentication code carrier 100. If the authenticating unit 1282 determines that the authenticating code carrier 100 is true, it can be known that the corresponding atomized medicine container 10 is not forged, such that the user can use it with confidence.

After the above authentication operation, the authentication module 128 may be configured to generate the authentication result signal S11 correspondingly, and the control unit 124 may be further configured to determine whether to control the first power module 122 to output the first driving voltage V11 according to the authentication result signal S11. Specifically, if the authentication unit 1282 determines that the authentication code carrier 100 is true, the corresponding authentication result signal S11 can enable the control unit 124 to control the first power module 122 to output the first driving voltage V11 to drive the atomization element 132 of the atomization module 120, and to further atomize the atomized medicine 102. On the other hand, if the authentication unit 1282 determines that the authentication code carrier 100 is fake, or the authentication unit 1282 cannot recognize the authentication information 1004, then the correspondingly output authentication result signal S11 may disable the control unit 124.

Fourth Embodiment

Figure 8:
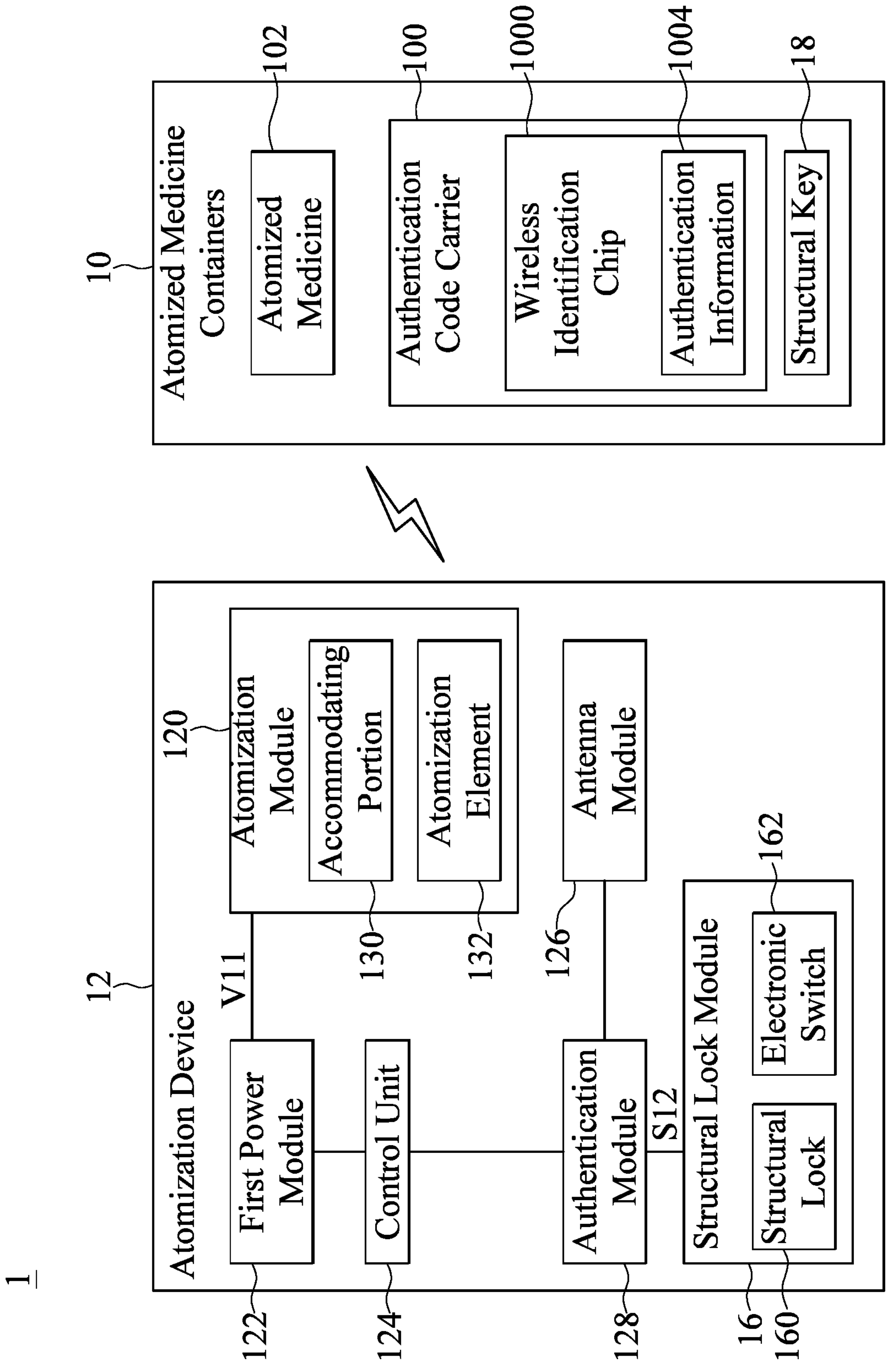
FIG. 8 is a block diagram of an atomization system with a single authentication mechanism according to a fourth embodiment of the present invention.
Figure 9:
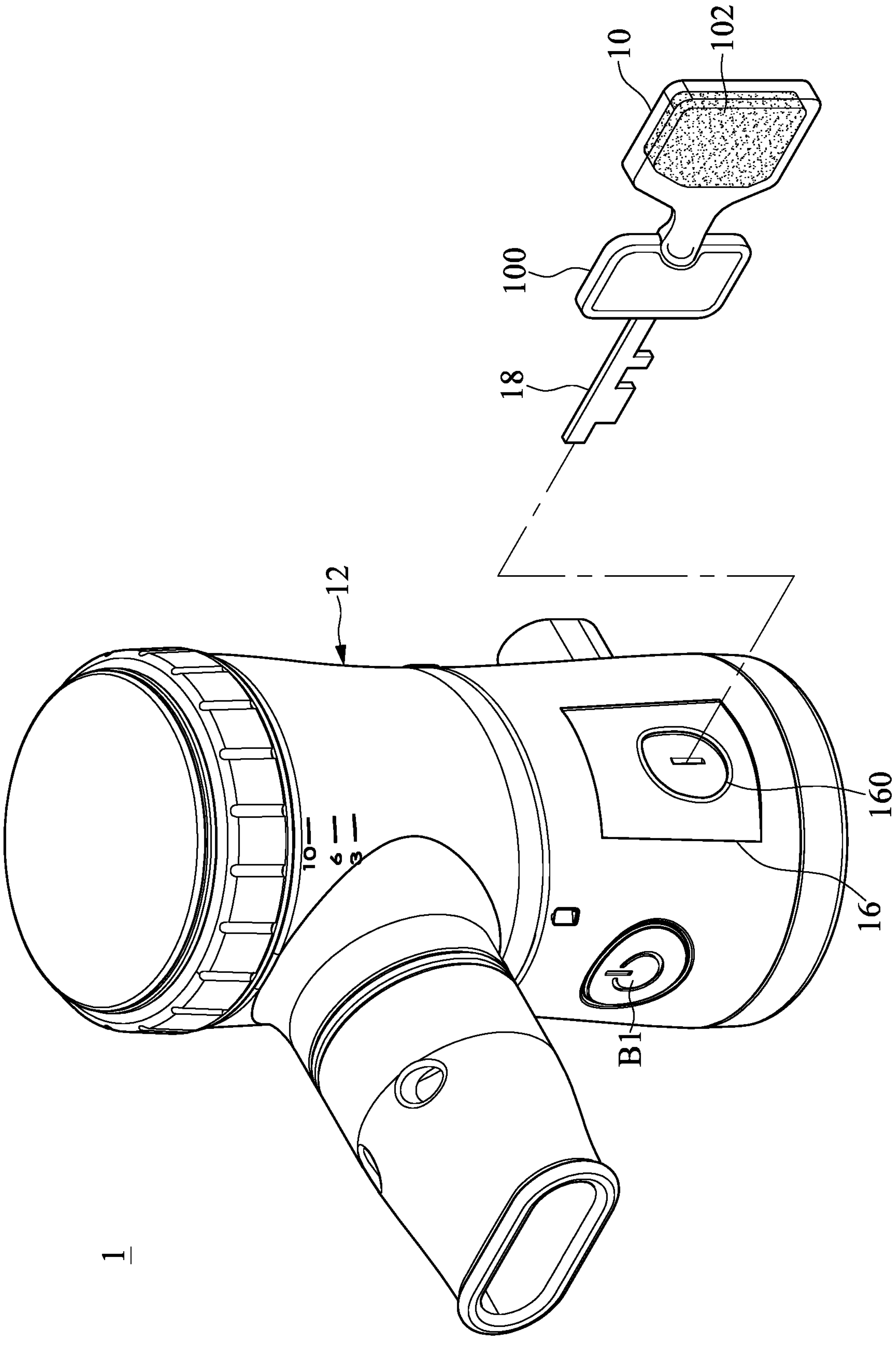
FIG. 9 is a perspective view of an atomization system with a single authentication mechanism according to a fourth embodiment of the present invention.

Reference is now made to FIGS. 8 and 9, which are a block diagram and a perspective view of an atomization system with a single authentication mechanism according to a fourth embodiment of the present invention, respectively. As shown in the figures, the atomization device 12 further includes a structural lock module 16 connected with the authentication module 128, and the authentication code carrier 100 further includes a structural key 18. The structural lock module 16 includes a structural lock 160 and an electronic switch 162. When the structural lock 160 of the structural lock module 16 is successfully unlocked by the structural key 18, the electronic switch 162 of the structural lock module 16 is configured to transmit the enabling signal S12 to enable the authentication module 128 to perform the authentication operation.

On the other hand, the structural lock module 16 may also be a digital or optical authentication lock that includes a digital or analog mechanism. The structural key 18 has an unlocking sensing element, and the structural lock module 16 includes a key sensing mechanism, a judging mechanism, and a lock body actuation mechanism, the key sensing mechanism contacts and senses the unlocking sensing element by inserting the unlocking sensing element of the structural key 18 into the key sensing mechanism, and when the judging mechanism judges that unlocking the sensing element meets the preset unlocking condition, the lock body is actuated by the lock body actuation mechanism to be switched to the unlocked state.

As shown in FIG. 9, the present embodiment has a double safety mechanism in practice. First, when the user obtains the atomized medicine container 10, a structural key 18 having a specific structure can be obtained, which can be disposed inside the bottle cap serving as the authentication code carrier 100, the structural key 18 and the structural lock 160 on the atomization device 12 provided by the manufacturer may be consistent in terms of commercial nature to provide the first level of security.

Secondly, after the user successfully unlocks the structural lock 160 with the structural key 18, the electronic switch 162 will transmit a start up signal S12 to enable the authentication module 128. Preferably, the authentication code carrier 100 may have an authentication chip 1000 provided for the wireless identification module 128 to perform the identification, the authentication module 128 may further obtain the authentication information 1004 through the antenna module 126, and perform the authentication operation according to the third embodiment. For example, comparing the authentication information 1004 with the data stored in the memory 1284, or the obtained authentication information 1004 is an anti-counterfeiting identification code having a specific coding sequence, and a specific algorithm stored in the memory 1284 may be further executed for decryption to determine the authenticity of the atomized medicine container 10 or the atomized medicine 102. In this way, a second level of security can be provided.

Therefore, this embodiment can provide double guarantees of the structural key and the wireless identification, which not only ensures safety, but also increases the difficulty of forging atomized medicine containers.

Fifth Embodiment

Figure 10:
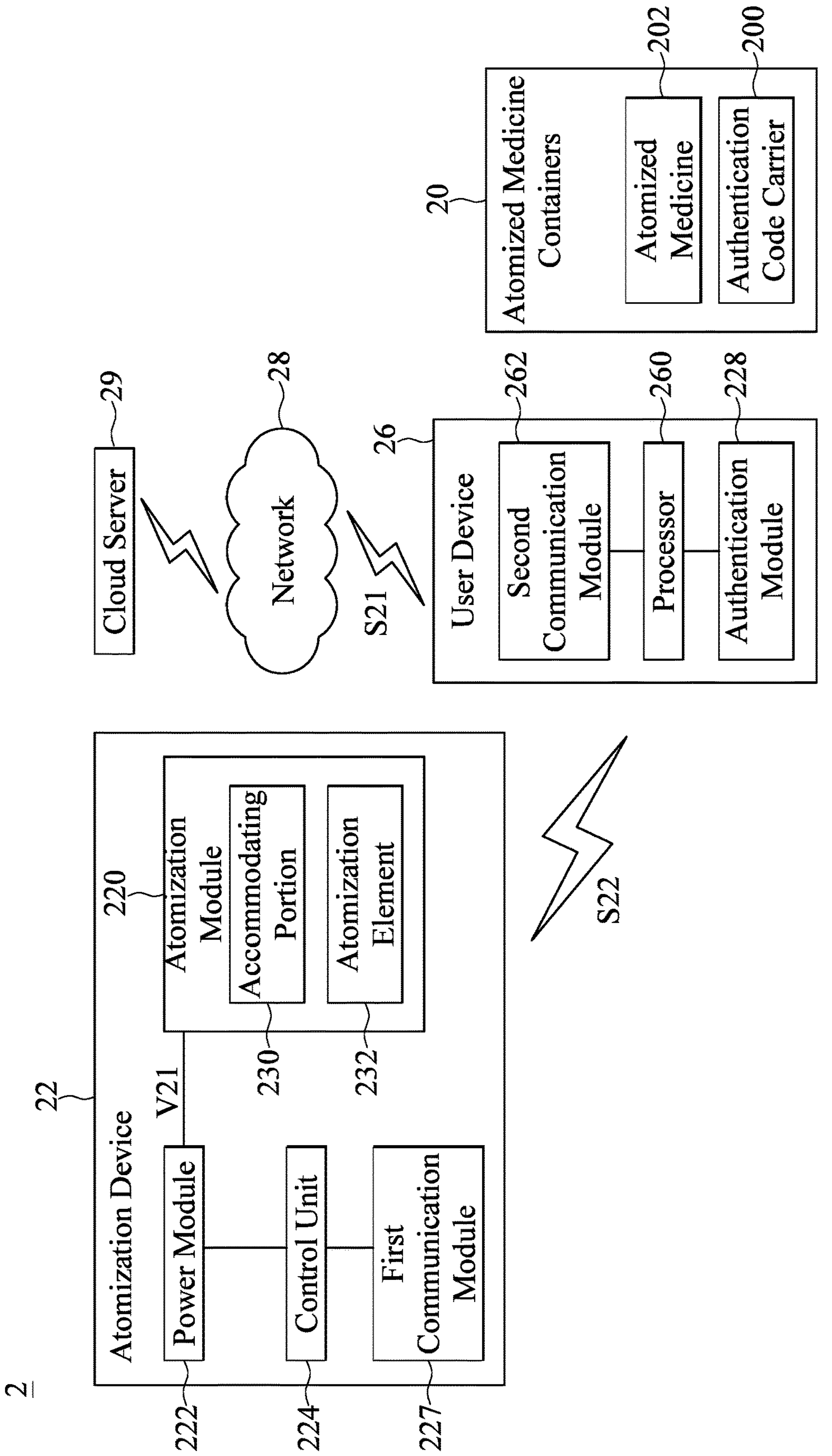
FIG. 10 is a block diagram of an atomization system having a double authentication mechanism according to a fifth embodiment of the present invention.

Reference is now made to FIG. 10, which is a block diagram of an atomization system having a double authentication mechanism according to a fifth embodiment of the present invention. As shown, the atomization system 2 includes an atomized medicine container 20, an atomization device 22, a user device 26, and a cloud server 29. The atomized medicine container 20 has an authentication code carrier 200, and the atomized medicine container 20 accommodates the atomized medicine 202. Similarly, the atomized medicine container 20 may be a bottle container with a bottle rim, and the authentication code carrier 200 may be an electronic tag provided on the bottle cap to be used separately from the bottle container, but the present invention is not limited thereto, and the authentication code carrier 200 may also be an electronic tag detachably disposed outside the bottle container.

Referring to FIG. 10, the atomization device 22 includes an atomization module 220, a power module 222, a control unit 224, and a first communication module 227. The atomization module 220 has an accommodating portion 230 and an atomization element 232. The accommodating portion 230 can be used for loading the aforesaid atomized medicine 202, and the atomization element 232 is used for atomizing the atomized medicine 202 when it is placed in the accommodating portion 130. In addition, the control unit 224 is electrically connected to the power module 222, and the power module 222 is electrically connected to the atomization module 220.

In practice, the control unit 224 controls the power module 222 to output the first driving voltage V21. The first driving voltage V21 output by the power module 222 is mainly used to directly drive the atomization module 220. In detail, the control unit 224 may be, for example, a control chip, a micro control chip, or a PWM control chip. The present embodiment does not limit the aspect of the control unit 224. The control unit 224 has a plurality of built-in ports that can output pulse modulation signals, and can provide control signals with different frequencies and duty cycles. The frequency adjustment range may be, for example, 10 Hz~1 MHz, and the duty cycle adjustment range may be, for example 10% to 90%. In practice, the control unit 224 may output one or more control signals. The control signal is used to control the operation of the power module 222.

The power module 222 may be, for example, a driving circuit including one or more switches, one or more inductors, one or more capacitors and diodes. The present embodiment does not limit the aspect of the power module 222. The power module 222 is configured to receive the control signal output by the control unit 224. In practice, the power module 222 provides the atomization module 120 with the first driving voltage V21 that oscillates at the output frequency according to the control signal. The first driving voltage V21 may be, for example, a pulsing DC voltage. The waveform of the first driving voltage V21 may be, for example, a sine wave, a triangular wave, or a square wave.

In this embodiment, the authentication operation is mainly performed on the user device 26 and the cloud server 29, and the atomization device 22 may not need to be provided with an authentication module and its related device or system, which can save the manufacturing costs. The user device 26 includes a processor 260, a second communication module 262, and an authentication module 228. In the present invention, examples are not limited by the prerequisites of an embodiment, and further examples of various embodiments in a wide variety of operating environments can include any number of applications that can be used to operate one or more server computers, user computers or computing devices. The user device 26 may include any number of general-purpose personal computers running standard operating systems, such as laptop or notebook, and mobile phones, wireless phones and hand-held devices that execute mobile software and are capable of supporting a large number of Internet and messaging communication protocols. Such a system may also include a number of workstations, running any of a variety of commercially available operating systems for development and database management purposes, and other known applications. These devices may also include other electronic devices capable of communicating through the network, such as virtual terminals, host-clients, gaming systems, and other devices.

Functions of the processor 260 included in the user device 26 may be implemented by using one or more processors. The processor may be a programmable unit, such as a microprocessor, microcontroller, digital signal processor (DSP) chip, a field programmable gate array (field-programmable gate array; FPGA) and the like. Functions of the processor may also be implemented by one or several electronic devices or ICs. In other words, the functions performed by the processor 260 may be implemented in a hardware domain or a software domain or a combination of the hardware domain and the software domain.

The user device 26 further has a second communication module 262, which is connected to the processor 260, configured to pair with the first communication module 227, and connected to the cloud server 29 through the network 28. The pairing of the first communication module 227 and the second communication module 262 can be transmitted through the near-end network, such as WIFI, Bluetooth, etc. More specifically, the user device 26 can obtain administrator rights of the atomization device 22 through the pairing operation, such that wireless controls and authentication mechanisms may be achieved.

In addition, in the example using the cloud server 29, the cloud server 29 can operate any of various servers or mid-tier applications including HTTP servers, FTP servers, CGI servers, data servers, Java servers and business application servers. The cloud server 29 may also execute programs or scripts to respond to requests from the user devices. For example, by executing one or more web applications, it can be implemented as one or more scripts written in any programming language, such as Java, C, C#, or C++ or any scripting language such as Perl, Python, or TCL and combinations thereof. The cloud server 29 may also include database servers, including but not limited to those commercially available from the open market.

As mentioned above, the cloud server 29 may include various data storing memories, other memories and storage media. These can reside in a variety of locations, such as on a storage medium local to (and/or resident in) one or more of the computers or remote from any or all of the computers across the network. In a particular set of examples, the information can reside in a storage-area network (SAN) familiar to those skilled in the art. Similarly, any necessary files for performing the functions attributed to the computers, servers or other network devices can be stored locally and/or remotely, as appropriate. Where a system includes computerized devices, each such device can include hardware elements that can be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system can also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared computing device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate examples can have numerous variations from that described above. For example, customized hardware might also be used and/or particular elements might be implemented in hardware, software (including portable software, such as applets) or both. Further, connection to other computing devices such as network input/output devices can be employed.

Storage media and computer readable media for containing code, or portions of code, can include any appropriate media known or used in the art, including storage media and computing media, such as but not limited to volatile and non-volatile, removable and non-removable media implemented in any method or technology for storage and/or transmission of information such as computer readable instructions, data structures, program modules or other data, including RAM, ROM, EPROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the technology and teachings provided herein, a person of ordinary skill in the art will appreciate other ways and/or methods to implement the various aspects of the present technology.

The user device 26 further has an authentication module 228 connected to the processor 260, which is configured to perform an authentication operation related to the authentication code carrier 200, and to further determine the authenticity of atomized medicine container 20 or the atomized medicine 202 through the cloud server 29, and to generate an authentication result signal S21 correspondingly.

The authentication module 228 is configured to determine whether to control the second communication module 262 through the processor 260 to transmit an authentication success signal S22 to the first communication module 227 according to the authentication result signal S21. When the first communication module 227 receives the authentication success signal S22, the control unit 224 controls the power module 222 to output the first driving voltage V21.

Specifically, the authentication operation between the authentication module 228 and the authentication code carrier 200 may utilize the radio frequency identification (RFID), which is mainly composed of radio frequency tag (RFID tag), reader or barcode reader and related application system.

Figure 11A:
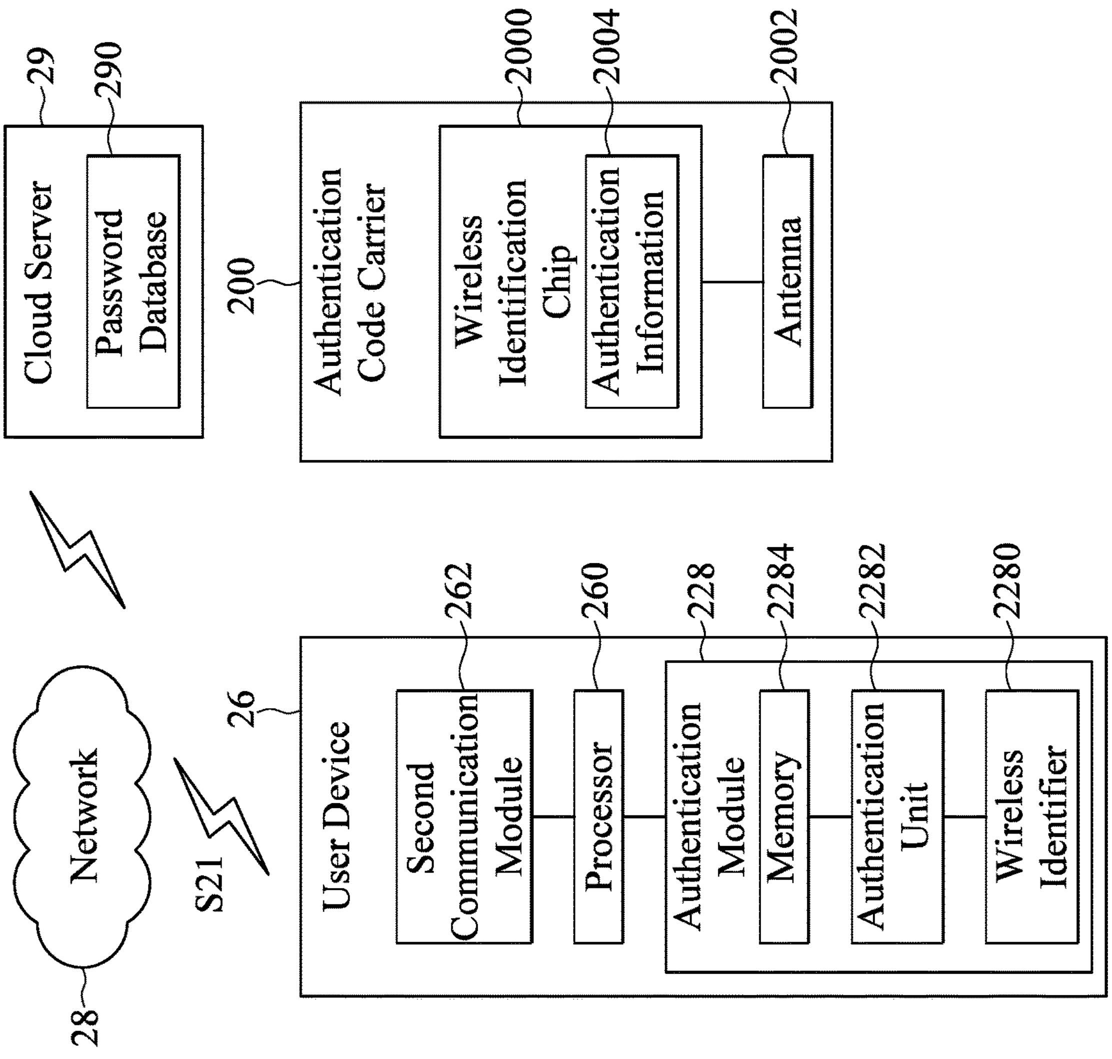
FIG. 11A is a block diagram of a user device, a cloud server, and an authentication code carrier according to a fifth embodiment of the present invention.
Figure 11B:
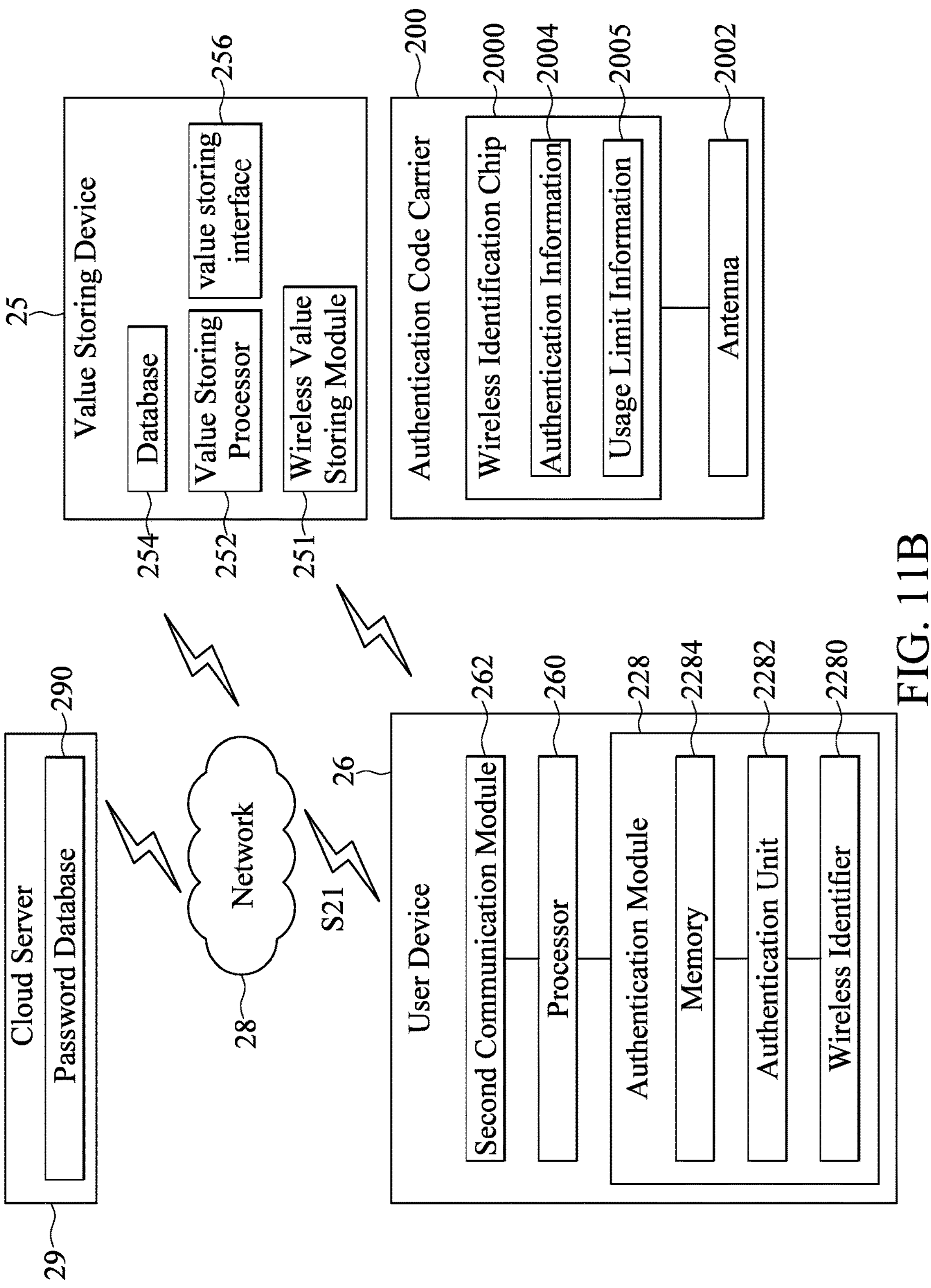
FIG. 11B is a block diagram of a user device, a cloud server, an authentication code carrier, and a value storing device according to a fifth embodiment of the present invention.

Reference is now made to FIGS. 11A and 11B, which are block diagrams of a user device, a cloud server, and an authentication code carrier according to a fifth embodiment of the present invention. As shown in the figures, the authentication module 228 includes a wireless identifier 2280, an authentication unit 2282, and a memory 2284, the authentication code carrier 200 includes a wireless identification chip 2000 and an antenna 2002 connected thereto. In this example, the authentication operation between the authentication module 228 and the authentication code carrier 200 is mainly based on the passive RFID technology, which is directly powered by the wireless identifier 2280 through the radio waves transmitted by the antenna module 226 to the radio frequency identification tag, that is, the wireless identification chip 2000 itself, and the wireless identification chip 2000 further has authentication information 2004 written in advance. Here, the authentication information 2004 may be an anti-counterfeiting identification code having a specific coding sequence and product history data. In practice, the wireless identifier 2280 may be utilized to read the authentication information 2004 previously written in the wireless identification chip 2000 so as to effect anti-fake improvements using the anti-counterfeit identification code and product history data.

However, unlike the foregoing embodiment, the authentication operation for determining the authenticity of the authentication information 2004 is mainly performed by the cloud server 29. After the authentication unit 2282 reads the wireless identification chip 2000, the authentication information 2004 may be obtained, which may be an anti-counterfeit identification code having a specific coding sequence, and is transmitted to the cloud server 29 through the second communication module 262. The built-in processor of the cloud server 29 can execute a specific decryption algorithm to confirm the authenticity of the authentication code carrier 200 having the authentication information 2004. In addition, another example of the authentication operation performed by the cloud server 29 may compare a part or all of the authentication information 2004 with the data stored in the password database 290 to confirm the authenticity of the authentication code carrier 200. If the cloud server 29 determines that the authenticating code carrier 200 is true, it can be known that the corresponding atomized medicine container 20 is not forged, such that the user can use it with confidence.

Specifically, the password database 290 may be pre-established according to a list of products sold by a pharmaceutical supplier, and the password database 290 may have a plurality of unique authentication information 2004, and multiple and unique passwords corresponding to the authentication information 2004. After the cloud server 29 receives the read authentication information 2004, the cloud server 29 then performs a comparison operation in the password database 290 according to the authentication information 2004 to obtain password information corresponding to the authentication information 2004. Since the password database 290 may be instantly updated by the supplier, it may be ensured that the atomized medicine containers 20 purchased by users have not been used or faked.

After the above authentication operation, if the comparison operation of the cloud server 29 succeeds in obtaining the password information, the authentication result signal S21 including the password information may be transmitted back to the authentication module 228. The authentication unit 2282 of the authentication module 228 may process the authentication result signal S21 to control the second communication module 262 to transmit the authentication success signal S22 to the first communication module 227 through the processor 260. In detail, the password information included in the authentication result signal S21 can be used by the authentication unit 2282 for decryption, so as to confirm that the authentication result signal S21 is indeed from the cloud server 29, or to identify the encrypted authentication result signal S21. These security mechanisms may also prevent persons of interest from intercepting, analyzing and cracking the signals. After being processed by the authentication unit 2282, the processor 260 controls the second communication module 262 to transmit the authentication success signal S22 to the first communication module 227.

When the first communication module 227 receives the authentication success signal S22, the control unit 224 is configured to control the power module 222 to output the driving voltage V21 according to the authentication success signal S22. Specifically, if the authentication code carrier 200 is determined to be true through the cloud server, the correspondingly obtained authentication success signal S22 may enable the control unit 224, thereby controlling the power module 222 to output the driving voltage V21 to drive the atomization element 232 of the atomization module 220 for atomizing the atomized medicine 202. On the other hand, if the authentication unit 29 determines that the authentication code carrier 200 is fake, or the authentication unit 2282 cannot recognize the authentication result signal S21, then the correspondingly output authentication result signal may disable the control unit 224.

The double authentication mechanism provided by the present embodiment may greatly increase the difficulty of counterfeiting the authentication code carrier, so as to ensure the security of data transmission, such that the counterfeit goods are not able to be used by the atomization device even if they are sold in the market, thus protecting the lives and property of consumers.

Reference is now made to FIG. 11B, which is a block diagram of a user device, a cloud server, an authentication code carrier, and a value storing device according to a fifth embodiment of the present invention. As shown, the atomization system 2 having the double authentication mechanism further includes a value storing device 25. The value storing device 25 includes a wireless value storing module 251, a value storing processor 252, a database 254, and a value storing interface 256.

In the present embodiment, the number of the atomized medicine container 20 may be plural, and the plurality of atomized medicine containers 20 are associated with the authentication code carrier 200 in a many-to-one manner. Specifically, the authentication code carrier 200 may be attached in the form of a card to a box containing a plurality of atomized medicine containers 20, and the authentication code carrier 200 further includes usage limit information 2005.

Therefore, in the foregoing authentication operation, the authentication unit 2282 of the authentication module 228 may be further configured to determine whether the usage limit information 2005 reaches a predetermined limit amount. For example, if the cloud server 29 determines that the authentication code carrier 200 is true, the cloud server 29 may further obtain the usage limit information 2005, which defines the usage limit of the authentication code carrier 200, and the usage number corresponds to the number of atomized medicine containers 20 and decreases as the number of usage increases. In this embodiment, the predetermined limit amount may be defined as 0, that is, the authentication unit 2282 of the authentication module 228 determines whether the usage limit information 2005 has reached 0, and if yes, it represents that the user exceeds the usage limit of times, and thus the corresponding authentication failure signal is generated to disable the control unit 224.

In other words, if the authentication unit 2282 of the authentication module 228 determines that the usage limit information 2005 has not reached 0, the authentication module 228 is then configured to update the usage limit information 2005, for example, to reduce the number of uses of the authentication code carrier 200 by one, and the authentication success signal S22 is generated to enable the control unit 224 correspondingly.

On the other hand, the user may obtain the authentication code carrier 200 corresponding to one or more atomized medicine containers 20 when the atomized medicine is purchased. The usage limit information 2005 of the authentication code carrier 200 may be preset to 0, when the user completes the purchase at the pharmacy counter, staffs of the pharmacy may operate the value storing interface 256 to update the usage limit information 2005 by the wireless module 251, for example, configuring the value storing processor 252 to query or update the database 254 according to the purchased barcode, and to update the usage limit information 2005 preset to 0 to the purchased quantity of the atomization medicine containers 20. It should be noted that the wireless stored-value module 251 may have a configuration similar to the wireless identifier 2280, and the usage limit information 2005 may be updated.

Furthermore, the value storing device 25 can be further configured to be connected to the cloud server 29 through the network 28. After the user completes the purchase procedure at the pharmacy counter, the pharmacy can register at the cloud server 29 through the value storing device 25 at the same time, so as to synchronously update the information between the sales side and the production side.

It is worth mentioning that the authentication code carrier 200 can be disposable or reused, and after the usage limit information 2005 reaches 0, the user may directly use the same authentication code carrier 200 when purchasing a new medicine container 20 and updating the usage limit information 2005.

In addition, the value storing device 25 may directly store the usage limit information 2005 in the user device 26 through the wireless value storing module 251 directly after the user completes the purchase at the pharmacy counter. For example, the user device 26 may communicate with the wireless value storing module 25 through a radio frequency identification signal. The user device 26 may be a mobile electronic device having a near field communication (NFC) module, for simulating the operation of the RFID tag by using appropriate electronic circuits and corresponding antennas. The user device 26 provides the RFID function and may store a plurality of RFID tags, in other words, store the data necessary for simulating such RFID tags, such as the above-mentioned usage limit information 2005, or may directly transmit the usage limit information 2005 to the user device 26 through the network 28.

Therefore, in the foregoing authentication operation, the authentication unit 2282 of the authentication module 228 may be further configured to directly determine whether the usage limit information 2005 in the user device 26 reaches a predetermined limited amount. For example, if the cloud server 29 determines that the authentication code carrier 200 is true, the authentication unit 2282 may directly read the usage limit information 2005 in the user device 26, the usage limit information 2005 defines the usage limit of the authentication code carrier 200, and the usage number corresponds to the number of atomized medicine containers 20 and decreases as the number of usage increases. In this embodiment, the predetermined limit amount may be defined as 0, that is, the authentication unit 2282 of the authentication module 228 determines whether the usage limit information 2005 has reached 0, and if yes, it represents that the user exceeds the usage limit of times, and thus the corresponding authentication failure signal is generated to disable the control unit 224.

In other words, if the authentication unit 2282 of the authentication module 228 determines that the usage limit information 2005 has not reached 0, then the authentication module 228 is configured to update the usage limit information 2005, for example, to reduce the number of uses of the authentication code carrier 200 by one, and the authentication success signal S22 is generated to enable the control unit 224 correspondingly.

With the above configuration, when the user purchases a specific number of atomized medicine containers, it can ensure that the usage limit information corresponds to the number of atomized medicine containers, and the reliability of the authentication may be further increased.

Sixth Embodiment

Figure 12:
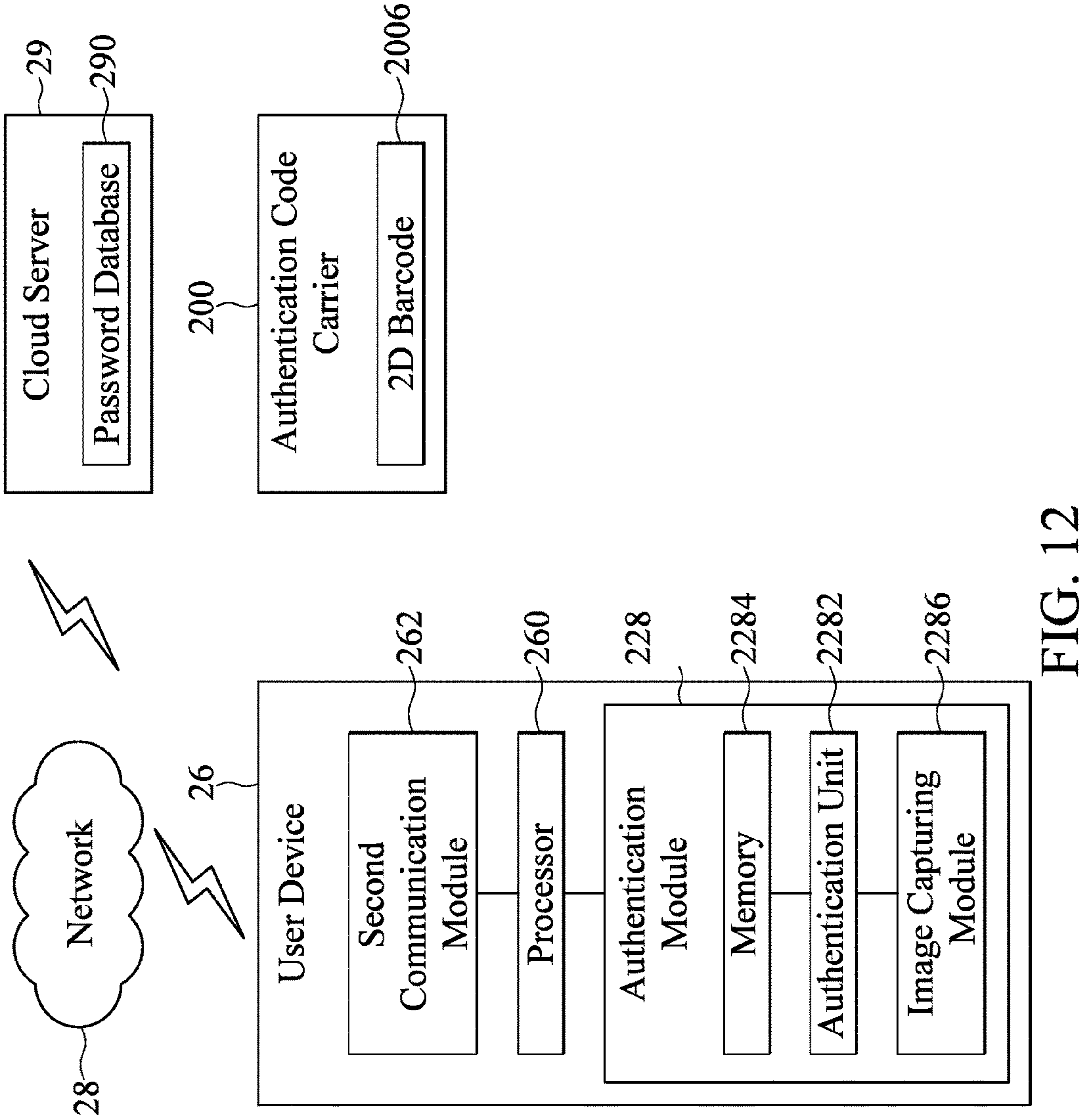
FIG. 12 is a block diagram of an atomization system having a double authentication mechanism according to a sixth embodiment of the present invention.

Reference is now made to FIG. 12, which is a block diagram of an atomization system having a double authentication mechanism according to a sixth embodiment of the present invention. In this embodiment, the reference numerals similar to the fifth embodiment designate similar elements and will not be further described. As shown in the figure, the sixth embodiment is different from the fifth embodiment in that the user device 26 further includes an image capturing module 2286 connected to the authentication unit 2282, and the authentication code carrier 200 further includes a two-dimensional barcode 2006. The two-dimensional barcode 2006 of the authentication code carrier 200 may be directly printed at a position where the authentication code carrier 200 is disposed, for example, inside or outside of the bottle cap or the bottle body of the atomized medicine container 20.

The user may obtain the image of the 2D barcode 2006 through the image capturing module 2286, and analyze the 2D barcode 2006 through the authentication unit 2282 to obtain the authentication information 2004. Specifically, this embodiment provides another implementation for obtaining the authentication information 2004, which utilizes a camera that is commonly provided in an existing smart phone, and also improves the convenience of the authentication. The production costs may be further reduced when compared with the previous embodiment in which the wireless identification chip is provided.

Similar to the fifth embodiment, the authentication information 2004 may be an anti-counterfeit identification code having a specific coding sequence, and is transmitted to the cloud server 29 through the second communication module 262. The built-in processor of the cloud server 29 can execute a specific decryption algorithm to confirm the authenticity of the authentication code carrier 200 having the 2D barcode 2006. In addition, another example of the authentication operation performed by the cloud server 29 may compare a part or all of the authentication information 2004 with the data stored in the password database 290 to confirm the authenticity of the authentication code carrier 200. If the cloud server 29 determines that the authenticating code carrier 200 is true, it can be known that the corresponding atomized medicine container 20 is not forged, such that the user can use it with confidence.

Similarly, after the cloud server 29 receives the read authentication information 2004, the cloud server 29 then performs a comparison operation in the password database 290 according to the authentication information 2004 to obtain password information corresponding to the authentication information 2004. Since the password database 290 may be instantly updated by the supplier, it can be ensured that the atomized medicine containers 20 purchased by users have not been used or faked.

Seventh Embodiment

Figure 13:
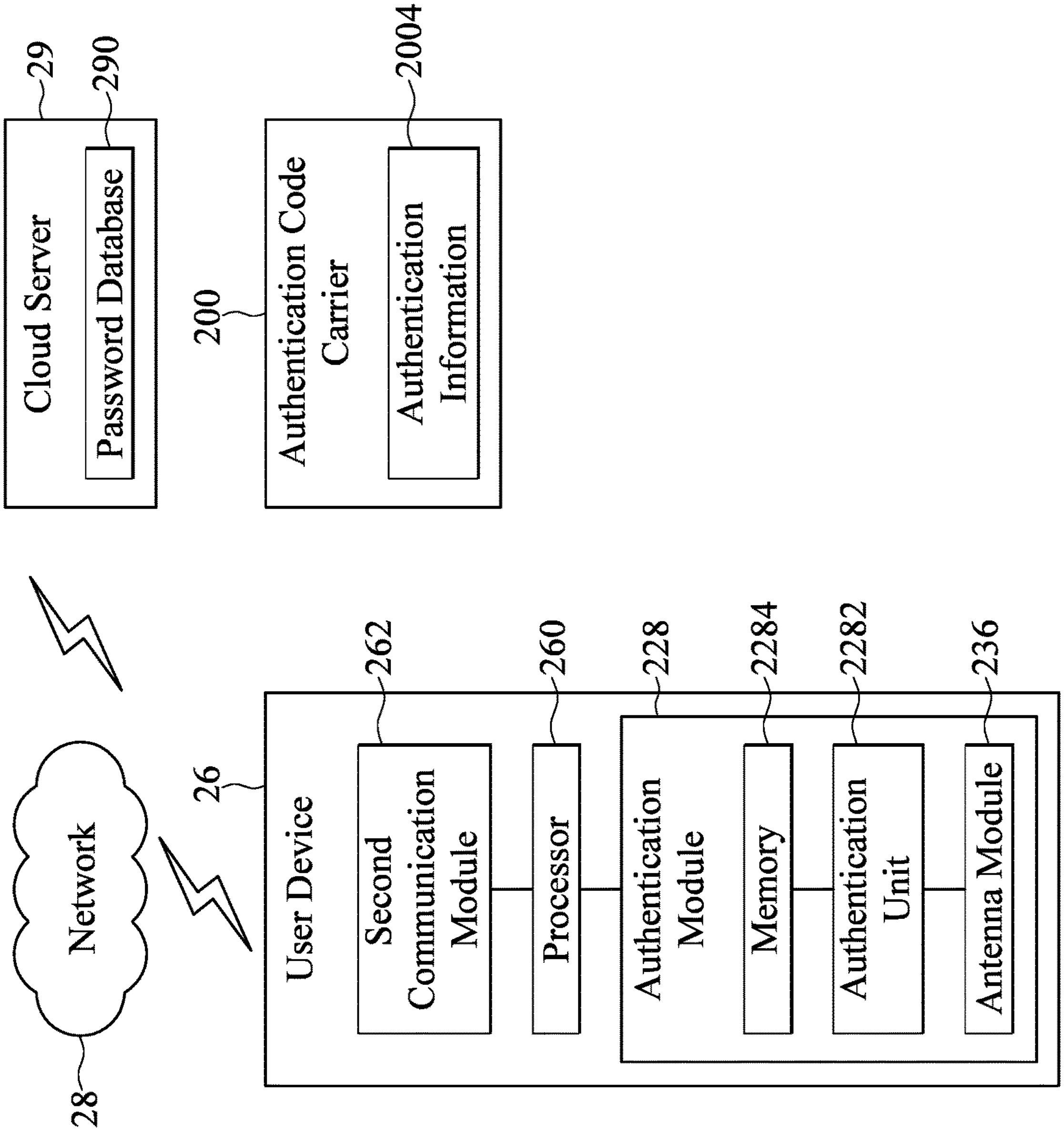
FIG. 13 is a block diagram of an atomization system having a double authentication mechanism according to a seventh embodiment of the present invention.

Reference is now made to FIG. 13, which is a block diagram of an atomization system having a double authentication mechanism according to a seventh embodiment of the present invention. In this embodiment, the reference numerals similar to the fifth embodiment designate similar elements and will not be further described. As shown, the difference between the seventh embodiment and the fifth embodiment is that the user device 26 further includes an authentication code input interface 236 connected with the authentication unit 2282.

Specifically, the user device 26 may include the above-mentioned authentication code input interface 236 and a control interface for the user to control the atomization module 220. For example, the user may control the atomizing device 22 to be turned on or off, and the flow rate of the atomized medicine 202 through the control interface on the user device 26 after the pairing operation. The authentication code input interface 236 may include numeric keys labeled with numbers 1-9, and cancel, back, and confirm keys.

On the other hand, the authentication information 2004 of the authentication code carrier 200 may be printed at a position where the authentication code carrier 200 is disposed, for example, inside or outside of the bottle cap or the bottle body of the atomized medicine container 20, the user can directly input the authentication code (i.e., authentication information 2004) through the authentication code input interface 236, and the authentication code can be correspondingly displayed on the display screen 140 commonly provided in the user device 26 for the user to confirm.

After the user inputs the authentication code (i.e., the authentication information 2004) through the authentication code input interface 236, the authentication unit 2282 directly obtains the authentication information 2004, or obtains the authentication information 2004 by decrypting the authentication code. Specifically, this embodiment provides another implementation for obtaining the authentication information 2004, which utilizes a user interface that is commonly provided by the existing smart phone, and also improves the convenience of the authentication. The production costs may be further reduced when compared with the previous embodiment in which the wireless identification chip is provided.

Similar to the fifth embodiment, the authentication information 2004 may be an anti-counterfeit identification code having a specific coding sequence, and is transmitted to the cloud server 29 through the second communication module 262. The built-in processor of the cloud server 29 can execute a specific decryption algorithm to confirm the authenticity of the authentication code carrier 200 having the authentication information 2004. In addition, another example of the authentication operation performed by the cloud server 29 may compare a part or all of the authentication information 2004 with the data stored in the password database 290 to confirm the authenticity of the authentication code carrier 200. If the cloud server 29 determines that the authenticating code carrier 200 is true, it can be known that the corresponding atomized medicine container 20 is not forged, such that the user can use it with confidence.

Similarly, after the cloud server 29 receives the read authentication information 2004, the cloud server 29 then performs a comparison operation in the password database 290 according to the authentication information 2004 to obtain password information corresponding to the authentication information 2004. Since the password database 290 may be instantly updated by the supplier, it can be ensured that the atomized medicine containers 20 purchased by users have not been used and faked.

Eighth Embodiment

Figure 14:
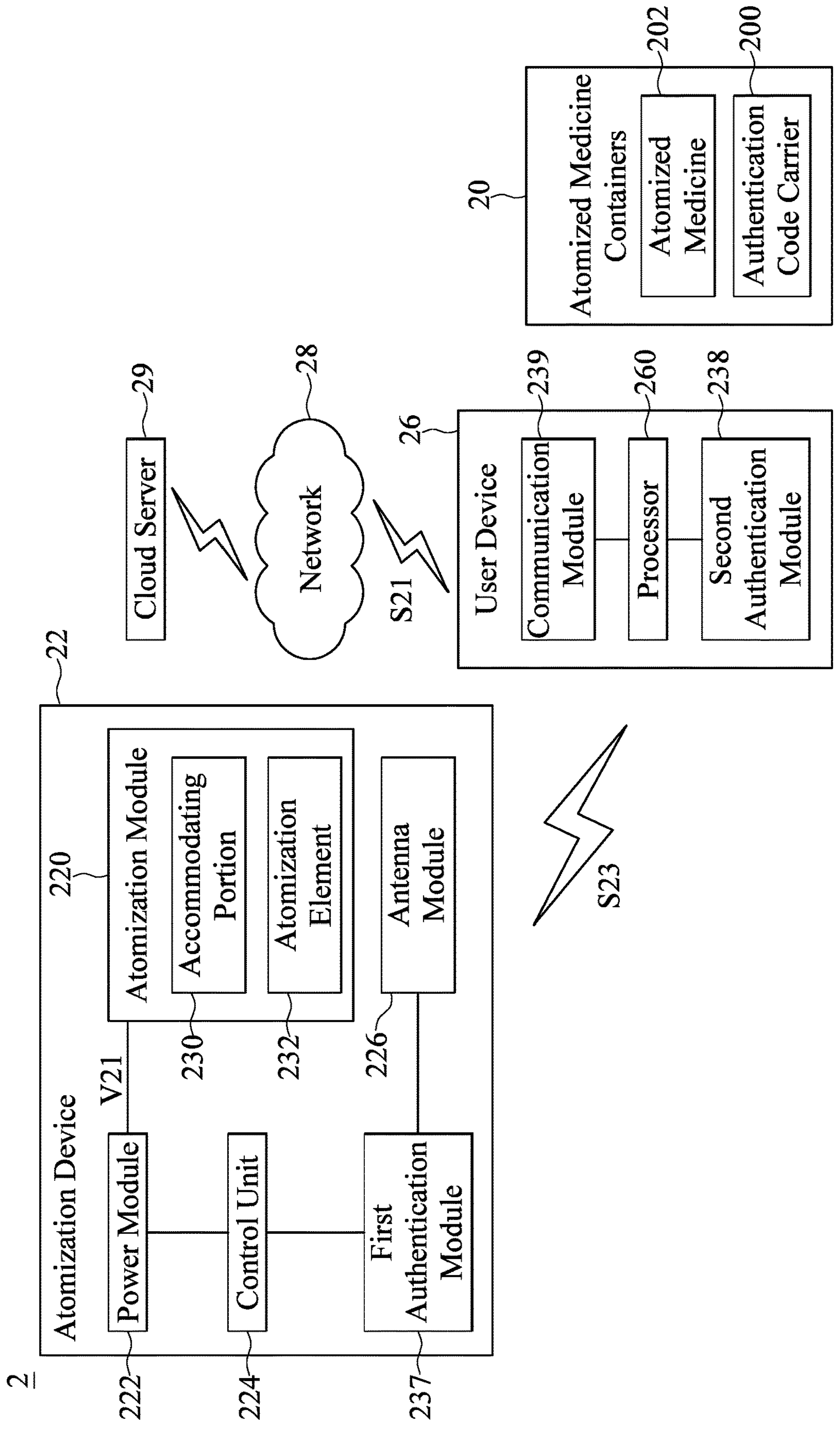
FIG. 14 is a block diagram of an atomization system having a double authentication mechanism according to an eighth embodiment of the present invention.

Reference is now made to FIG. 14, which is a block diagram of an atomization system having a double authentication mechanism according to an eighth embodiment of the present invention. In this embodiment, the reference numerals similar to the fifth embodiment designate similar elements and will not be further described. As shown in the figures, the difference between the eighth embodiment and the fifth embodiment is that the atomization device 22 is configured with a first authentication module 237 and an antenna module 226 connected to the first authentication module 237, and the user device 26 is configured with a second authentication module 238 and a communication module 239.

In this embodiment, the authentication operation is not only performed on the user device 26 and the cloud server 29, another authentication operation is also performed on the atomization device 22.

It should be noted that the functions and characteristics of the second authentication module 238 are basically similar to those of the authentication module 228 in the fifth embodiment, and the first authentication operation performed by the second authentication module 238 interacts with the authentication code carrier 200, and the authentication operation for determining the authenticity of the authentication code carrier 200 through the cloud server 29 are also the same, so that repeated descriptions are omitted herein. The difference will be described in detail with reference to FIG. 15.

Figure 15:
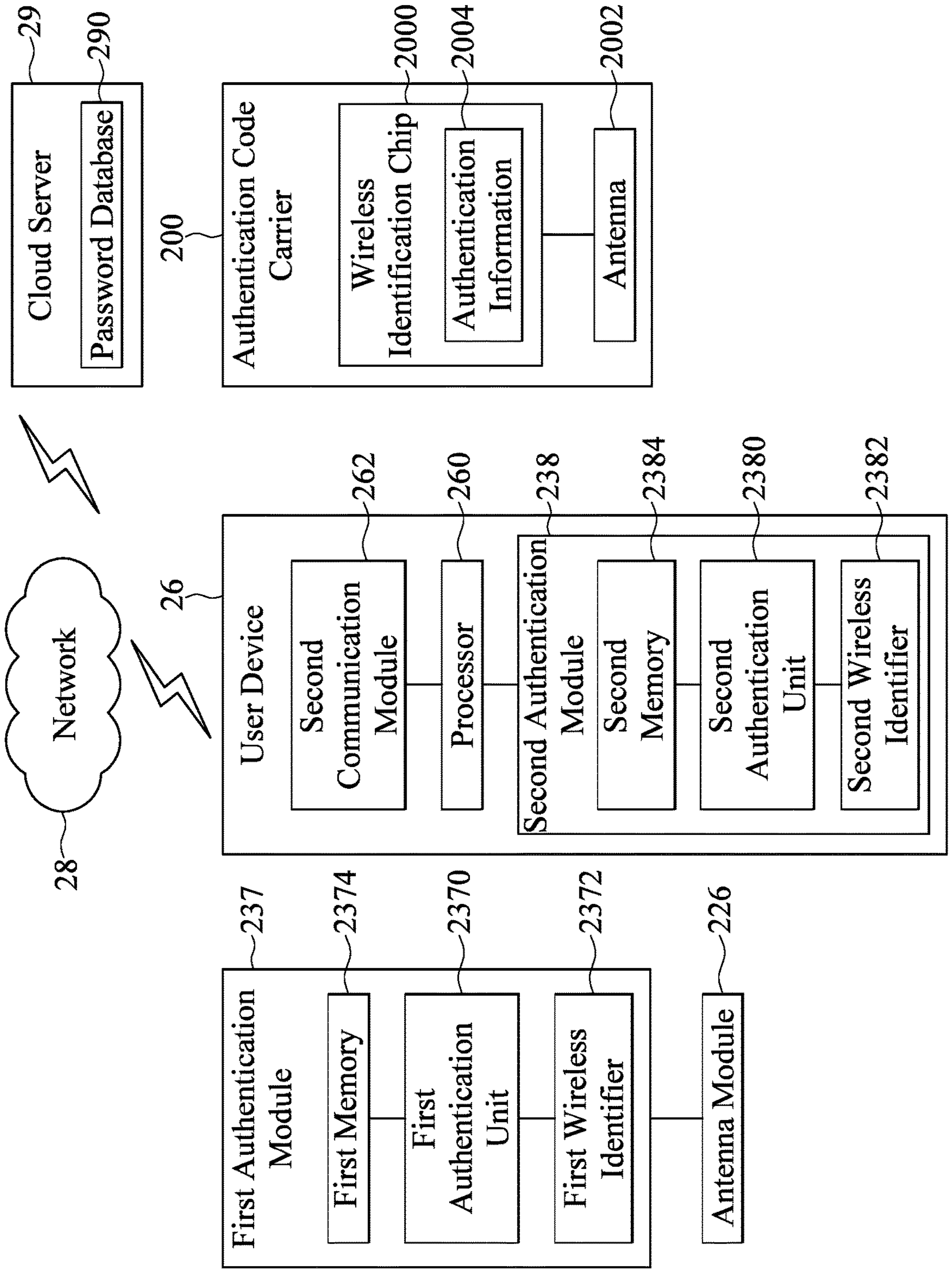
FIG. 15 is a block diagram of a first authentication module, an antenna module, a user device, a cloud server, and an authentication code carrier according to an eighth embodiment of the present invention.

FIG. 15 is a block diagram of a first authentication module, an antenna module, a user device, a cloud server, and an authentication code carrier according to an eighth embodiment of the present invention. As shown in the figure, the first authentication module 237 further includes a first authentication unit 2370, a first wireless identifier 2372, and a first memory 2374. The second authentication module 238 further includes a second authentication unit 2380, a second wireless identifier 2382, and a second memory 2384. The authentication code carrier 200 includes a wireless identification chip 2000 and an antenna 2002 connected thereto. In this example, the first authentication operation between the second authentication module 238 and the authentication code carrier 200 is mainly based on the passive RFID technology, which is directly powered by second authentication module 238 through the radio waves transmitted by the second wireless identifier 2382 to the radio frequency identification tag, that is, the wireless identification chip 2000 itself, and the wireless identification chip 2000 further has authentication information 2004 written in advance. Here, the authentication information 2004 may be an anti-counterfeiting identification code having a specific coding sequence and product history data. In practice, the second wireless identifier 2382 may be utilized to read the authentication information 2004 previously written in the wireless identification chip 2000 so as to effect anti-fake improvements using the anti-counterfeit identification code and product history data.

After the second authentication unit 2380 reads the wireless identification chip 2000, the authentication information 2004 may be obtained, which may be an anti-counterfeit identification code having a specific coding sequence, and is transmitted to the cloud server 29 through the second communication module 262. The built-in processor of the cloud server 29 can execute a specific decryption algorithm to confirm the authenticity of the authentication code carrier 200 having the authentication information 2004. In addition, another example of the first authentication operation performed by the cloud server 29 may compare a part or all of the authentication information 2004 with the data stored in the password database 290 to confirm the authenticity of the authentication code carrier 200. If the cloud server 29 determines that the authenticating code carrier 200 is true, it can be known that the corresponding atomized medicine container 20 is not forged, such that the user can use it with confidence.

Here, after the above authentication operation, if the comparison operation of the cloud server 29 succeeds in obtaining the password information, the authentication result signal S21 including the password information may be transmitted back to the second authentication module 238. The second authentication unit 2380 of the second authentication module 238 may process the authentication result signal S21 to determine whether to generate a wireless identification signal S23. In detail, the password information included in the authentication result signal S21 can be used by the second authentication unit 2380 for decryption, so as to confirm that the authentication result signal S21 is indeed from the cloud server 29, or to identify the encrypted authentication result signal S21. These security mechanisms may also prevent persons of interest from intercepting, analyzing or cracking the signals. After the second authentication unit 2380 is processed, a second authentication operation with the atomization device 22 is required.

Specifically, the second authentication operation between the user device 26 and the atomization device 22 may be performed through the radio frequency identification signal. The user device 26 may be a mobile electronic device having a near field communication (NFC) module for simulating the operation of the RFID tag by using appropriate electronic circuits and corresponding antennas. Such electronic circuit may be integrated into the circuit of the mobile device, or may form a part of the electronic circuit. In these cases, the electronic circuit of the mobile device may provide RFID functionality. The mobile device may store a plurality of RFID tags, in other words, store the data necessary for simulating such RFID tags. The emulation data includes data defining the air interface properties, such as operating frequency, modulation, protocol and the like, and data defining the actual data payload of the RFID tag. The data describing the RFID tag can then be made available to an RFID tag interrogation device through an RFID circuit and corresponding antenna. Therefore, the RFID tags finally configured by the NFC module may be available even when the mobile electronic device is either powered down on purpose or when its energy supply is exhausted, e.g. by a long telephone call.

Therefore, in the present embodiment, the second authentication module 238 may serve as a reader of the authentication code carrier 200, and may also generate a radio frequency identification signal that can be read by the first authentication module 237. In addition, when the user needs to continuously use a plurality of atomized medicine 202, the user device 26 may perform the first authentication operation on the plurality of authentication code carriers 200 in advance. After a plurality of corresponding authentication result signals S21 are obtained, the second authentication unit 2380 is configured to store the configuration for generating a plurality of wireless identification signals in the second memory 2384, respectively. The user can quickly switch and select the different atomized medicine 202 through the user device 26, so as to provide the user with more flexibility in the demand for medication.

Moreover, when the antenna module 226 receives the wireless identification signal S23, the first authentication module 237 is configured to perform a second authentication operation related to the wireless identification signal S23, and to further determine whether to enable the control unit 224 to control the power module 222 to output the driving voltage V21. For example, when the antenna module 226 receives the radio frequency identification signal generated by the second authentication module 238, the first wireless identifier 2372 analyzes the radio frequency identification signal, and the first authentication unit 2370 process the radio frequency identification signal to confirm the correctness of the radio frequency identification signal. If the signal is determined to be correct, the power module 222 is controlled by the control unit 224 to output the driving voltage V21 to directly drive the atomization element 232 of the atomization module 220 to atomize the atomized medicine 202 in the accommodating portion 230.

Furthermore, in addition to the foregoing second authentication operation performed with the radio frequency identification signal, the Bluetooth authentication signal may also be transmitted between the first authentication module 237 and the second authentication module 238. When the wireless identification signal S23 generated by the second authentication module 238 is a Bluetooth identification signal, the antenna module 226 receives the Bluetooth identification signal, the first wireless identifier 2372 analyzes the Bluetooth identification signal, and the first authentication unit 2370 process the Bluetooth identification signal to confirm the correctness of the radio frequency identification signal. If the signal is determined to be correct, the power module 222 is controlled by the control unit 224 to output the driving voltage V21 to directly drive the atomization element 232 of the atomization module 220 to atomize the atomized medicine 202 in the accommodating portion 230.

On the other hand, if the first authentication unit 2370 determines that the wireless identification signal S23 is incorrect, for example, the authentication unit 2282 cannot recognize the wireless radio frequency identification signal or the Bluetooth identification signal serving as the wireless identification signal S23, then the correspondingly output authentication failure signal may disable the control unit 224.

In certain cases, the first authentication module 237 may also have the capability of directly authenticating the authentication code carrier 200. For example, after the user device 26 has performed the first authentication operation with the cloud server 29, the authentication information 2004 of the wireless identification chip 2000 may be rewritten so that the first wireless identifier 2372 may directly perform the second authentication operation on the authentication information 2004 of the wireless identification chip 2000, so as to save the time for performing the first authentication operation through the user device 26 and the cloud server 29 every time the user needs to use the atomized medicine 202. On the other hand, when the user device 26 is operated without network connection capability, or the user device 26 is depleted of power, as long as the authentication code carrier 200 has performed the first authentication operation, the user may still directly use the atomized medicine 202 through the atomization device 22.

In this embodiment, in addition to providing a double authentication mechanism at the user device 26, an independent authentication mechanism is provided at the atomization device 22, which greatly increases the difficulty of counterfeiting the authentication code carrier when compared with the previous embodiments, so as to ensure the security of data transmission, such that the counterfeit goods are not able to be used by the atomization device even if they are sold in the market, thus protecting the lives and properties of consumers.

Ninth Embodiment

Figure 16:
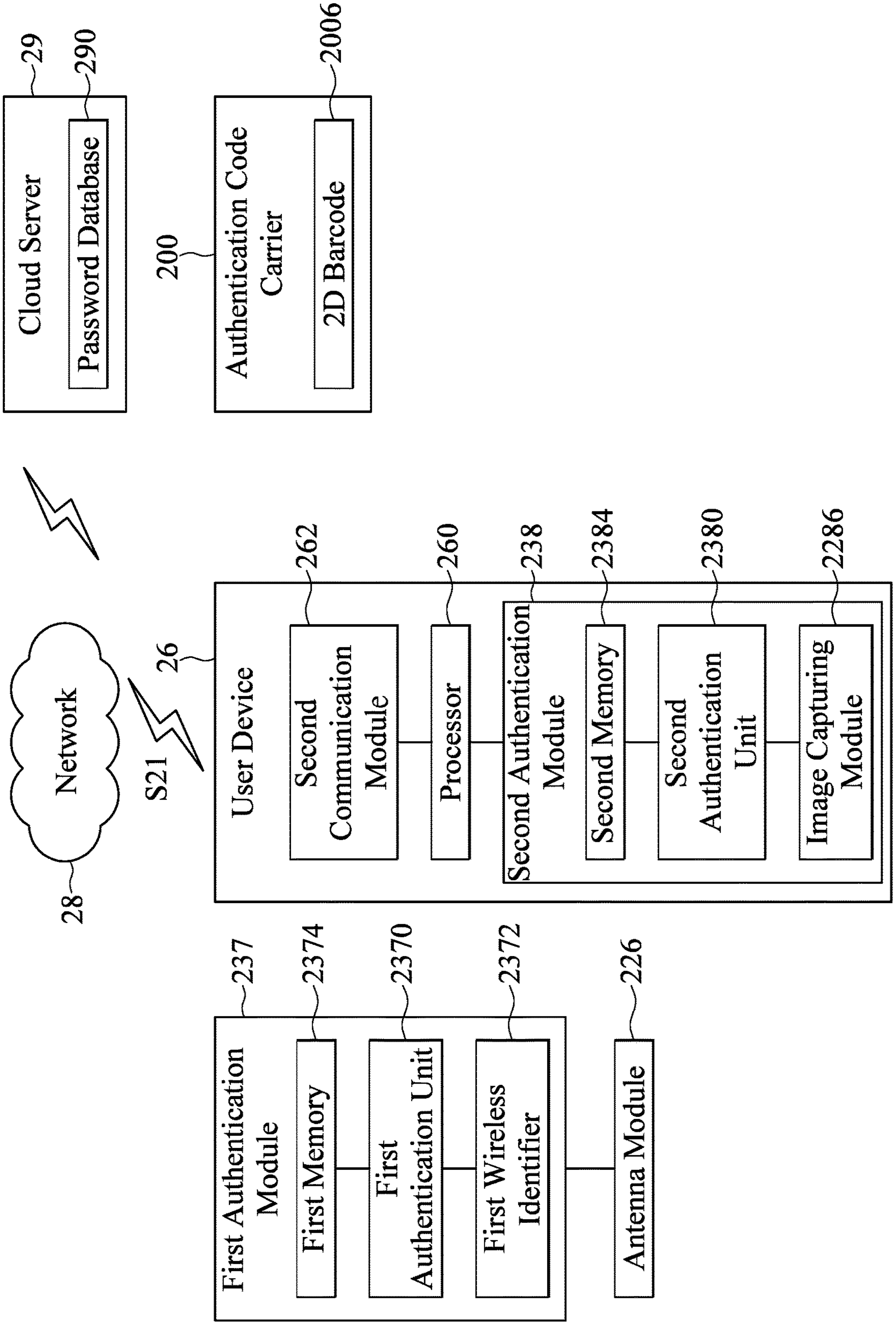
FIG. 16 is a block diagram of an atomization system having a double authentication mechanism according to a ninth embodiment of the present invention.
Figure 17:
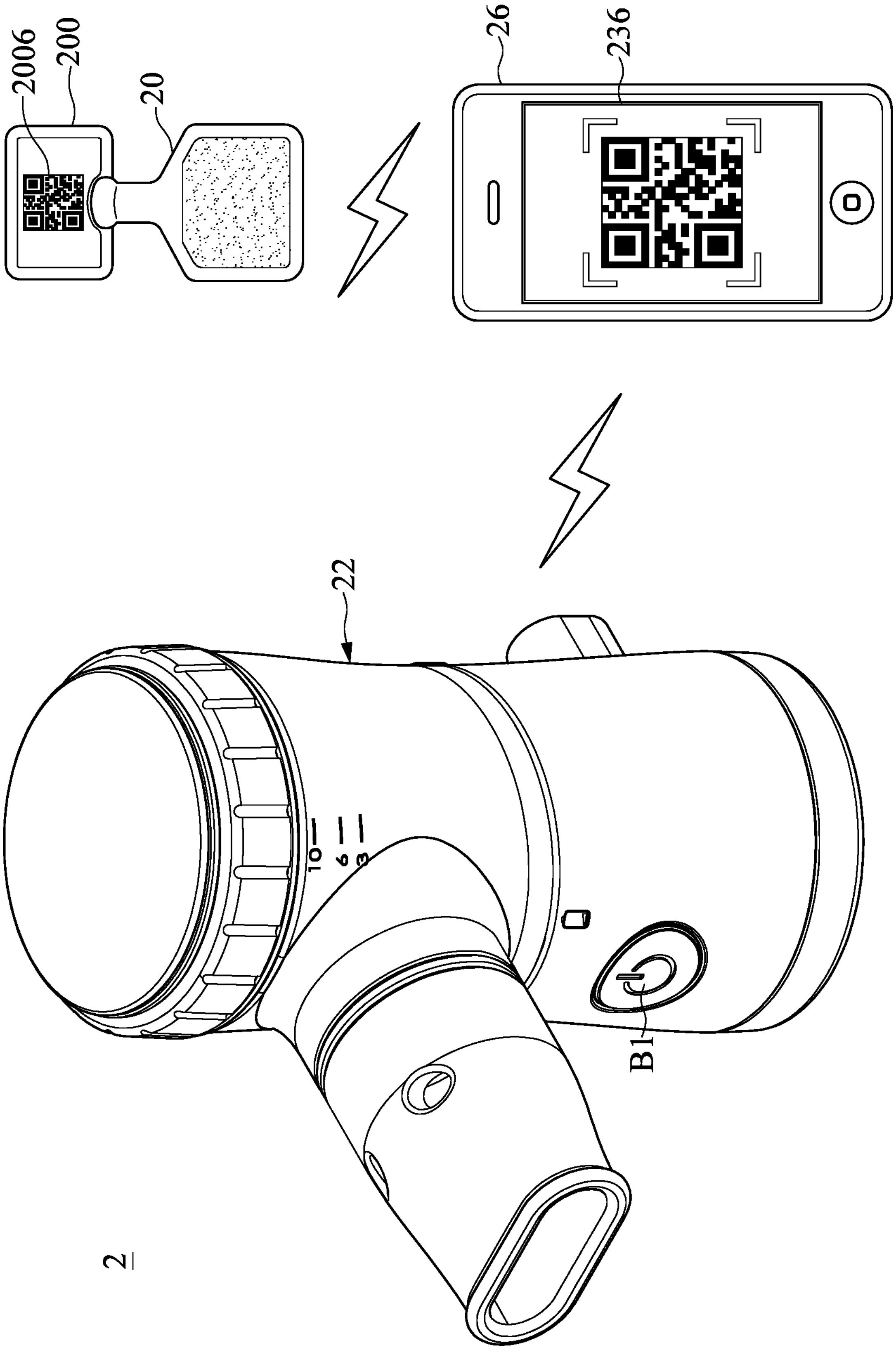
FIG. 17 is a perspective view of an atomization system having a double authentication mechanism according to a ninth embodiment of the present invention.

Reference is now made to FIGS. 16 and 17, which are a block diagram and a perspective view of an atomization system with a double authentication mechanism according to a ninth embodiment of the present invention, respectively. In this embodiment, the reference numerals similar to the eighth embodiment designate similar elements and will not be further described. As shown in the figure, the ninth embodiment is different from the eighth embodiment in that the user device 26 further includes an image capturing module 2286 connected to the authentication unit 2282, and the authentication code carrier 200 further includes a two-dimensional barcode 2006.

The user may obtain the image of the 2D barcode 2006 through the image capturing module 2286, and analyze the 2D barcode 2006 through the second authentication unit 2282 to obtain the authentication information 2004. Specifically, this embodiment provides another implementation for obtaining the authentication information 2004, which utilizes a camera that is commonly provided in an existing smart phone, and also improves the convenience of the authentication. The production costs may be further reduced when with the previous embodiment in which the wireless identification chip is provided.

Similar to the eighth embodiment, the authentication information 2004 may be an anti-counterfeit identification code having a specific coding sequence, and is transmitted to the cloud server 29 through the second communication module 262. The built-in processor of the cloud server 29 can execute a specific decryption algorithm to confirm the authenticity of the authentication code carrier 200 having the authentication information 2004. In addition, another example of the authentication operation performed by the cloud server 29 may compare a part or all of the authentication information 2004 with the data stored in the password database 290 to confirm the authenticity of the authentication code carrier 200. If the cloud server 29 determines that the authenticating code carrier 200 is true, it can be known that the corresponding atomized medicine container 20 is not forged, such that the user can use it with confidence.

Similarly, after the cloud server 29 receives the read authentication information 2004, the cloud server 29 then performs a comparison operation in the password database 290 according to the authentication information 2004 to obtain password information corresponding to the authentication information 2004. Since the password database 290 may be instantly updated by the supplier, it can be ensured that the atomized medicine containers 20 purchased by users have not been used and faked.

Similar to FIG. 14, after the above first authentication operation, if the comparison operation of the cloud server 29 succeeds in obtaining the password information, the authentication result signal S21 including the password information may be transmitted back to the second authentication module 238. The second authentication unit 2380 of the second authentication module 238 may process the authentication result signal S21 to determine whether to generate a wireless identification signal S23, and to perform the second authentication operation mentioned above.

The first authentication module 237 and the second authentication module 238 may also use radio frequency identification signals or Bluetooth identification signals for transmission. When the wireless identification signal S23 generated by the second authentication module 238 is a radio frequency identification signal or a Bluetooth identification signal, the antenna module 226 receives the radio frequency identification signal or the Bluetooth identification signal, the first wireless identifier 2372 analyzes the radio frequency identification signal or the Bluetooth identification signal, and the first authentication unit 2370 process the radio frequency identification signal or the Bluetooth identification signal to confirm the correctness of the radio frequency identification signal. If the signal is determined to be correct, the power module 222 is controlled by the control unit 224 to output the driving voltage V21 to directly drive the atomization element 232 of the atomization module 220 to atomize the atomized medicine 202 in the accommodating portion 230.

On the other hand, if the first authentication unit 2370 determines that the wireless identification signal S23 is incorrect, for example, the authentication unit 2282 cannot recognize the wireless radio frequency identification signal or the Bluetooth identification signal serving as the wireless identification signal S23, then the correspondingly output authentication failure signal may disable the control unit 224.

Tenth Embodiment

Figure 18:
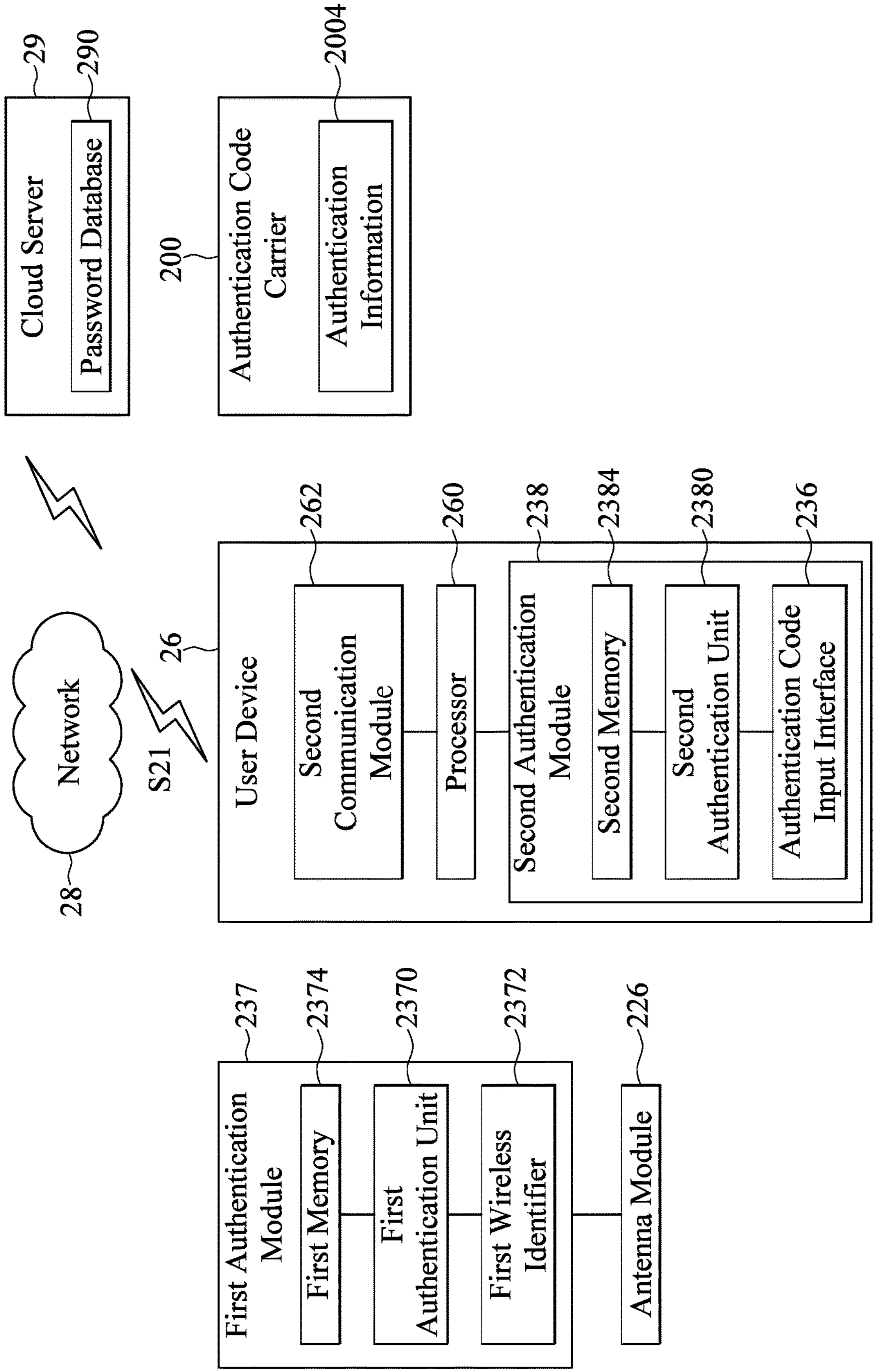
FIG. 18 is a block diagram of an atomization system having a double authentication mechanism according to a tenth embodiment of the present invention.

Reference is now made to FIG. 18, which is a block diagram of an atomization system having a double authentication mechanism according to a tenth embodiment of the present invention. In this embodiment, the reference numerals similar to the eighth embodiment designate similar elements and will not be further described. As shown, the difference between the tenth embodiment and the eighth embodiment is that the user device 26 further includes an authentication code input interface 236 connected with the second authentication unit 2380.

Specifically, the user device 26 may include the above-mentioned authentication code input interface 236 and a control interface for the user to control the atomization module 220. For example, the user may control the atomizing device 22 to be turned on or off, and the flow rate of the atomized medicine 202 through the control interface on the user device 26 after the pairing operation. The authentication code input interface 236 may include numeric keys labeled with numbers 1-9, and cancel, back, and confirm keys.

On the other hand, the authentication information 2004 of the authentication code carrier 200 may be printed at a position where the authentication code carrier 200 is disposed, for example, inside or outside of the bottle cap or the bottle body of the atomized medicine container 20, the user can directly input the authentication code (i.e., authentication information 2004) through the authentication code input interface 236, and the authentication code can be correspondingly displayed on the display screen 140 commonly provided in the user device 26 for the user to confirm.

After the user inputs the authentication code (i.e., the authentication information 2004) through the authentication code input interface 236, the second authentication unit 2380 directly obtains the authentication information 2004, or obtains the authentication information 2004 by decrypting the authentication code. Specifically, this embodiment provides another implementation for obtaining the authentication information 2004, which utilizes a user interface that is commonly provided by the existing smart phone, and also improves the convenience of the authentication.

Similar to the eighth embodiment, the authentication information 2004 may be an anti-counterfeit identification code having a specific coding sequence, and is transmitted to the cloud server 29 through the communication module 239. The built-in processor of the cloud server 29 can execute a specific decryption algorithm to confirm the authenticity of the authentication code carrier 200 having the authentication information 2004. In addition, another example of the authentication operation performed by the cloud server 29 may compare a part or all of the authentication information 2004 with the data stored in the password database 290 to confirm the authenticity of the authentication code carrier 200. If the cloud server 29 determines that the authenticating code carrier 200 is true, it can be known that the corresponding atomized medicine container 20 is not forged, such that the user can use it with confidence.

Similarly, after the cloud server 29 receives the read authentication information 2004, the cloud server 29 then performs a comparison operation in the password database 290 according to the authentication information 2004 to obtain password information corresponding to the authentication information 2004. Since the password database 290 may be instantly updated by the supplier, the atomized medicine containers 20 purchased by users may be ensured that those have not been used and faked.

Similarly, after the above authentication operation, if the comparison operation of the cloud server 29 succeeds in obtaining the password information, the authentication result signal S21 including the password information may be transmitted back to the second authentication module 238. The second authentication unit 2380 of the second authentication module 238 may process the authentication result signal S21 to determine whether to generate a wireless identification signal S23. It should be noted that the second authentication operation between the user device 26 and the atomization device 22 is the same as the second authentication operation described in the eighth embodiment. In order to avoid obscuring the emphasis of the present invention, the details are not described herein.

Eleventh Embodiment

The atomization method with the authentication mechanism of the present invention will be described in detail hereinafter while making reference to the accompanying drawings. In the present embodiment, the atomization method with the authentication mechanism is mainly applicable to the first embodiment to the fourth embodiment, but is not limited thereto, and the present embodiment may be implemented in a manner or various possibilities that can be considered by those skilled in the arts. The method provided by the present embodiment may also applicable to any of the embodiments described above.

The method according to the above-described embodiments may be implemented by using computer-executed instructions stored or otherwise accessible from a computer-readable medium. Such instructions may include, for example, instructions and data that cause or otherwise configure a general purpose computer, a special purpose computer, or a special purpose processing device to perform a certain function or set of functions. Parts of the computer resources used can be accessed via the Internet. The computer executable instructions may be, for example, binary, intermediate format instructions such as assembly language, firmware, or source code. Examples of computer-readable media that may be used to store instructions, information used, and/or information created during a method in accordance with the described embodiments include a magnetic or optical disk, flash memory, non-volatile memory USB memory devices, networked storage devices, and more.

In addition, devices for implementing the methods provided by the present disclosure may include hardware, firmware, and/or software, and may take any of a variety of configurations. Typical examples of such configurations include laptops, smart phones, small personal computers, personal digital assistants, and the like. The functions described herein may also be implemented in peripheral devices or built-in cards. By way of further example, such functions may also be implemented on circuit boards executing different processes on different chips or on a single device.

Figure 19:
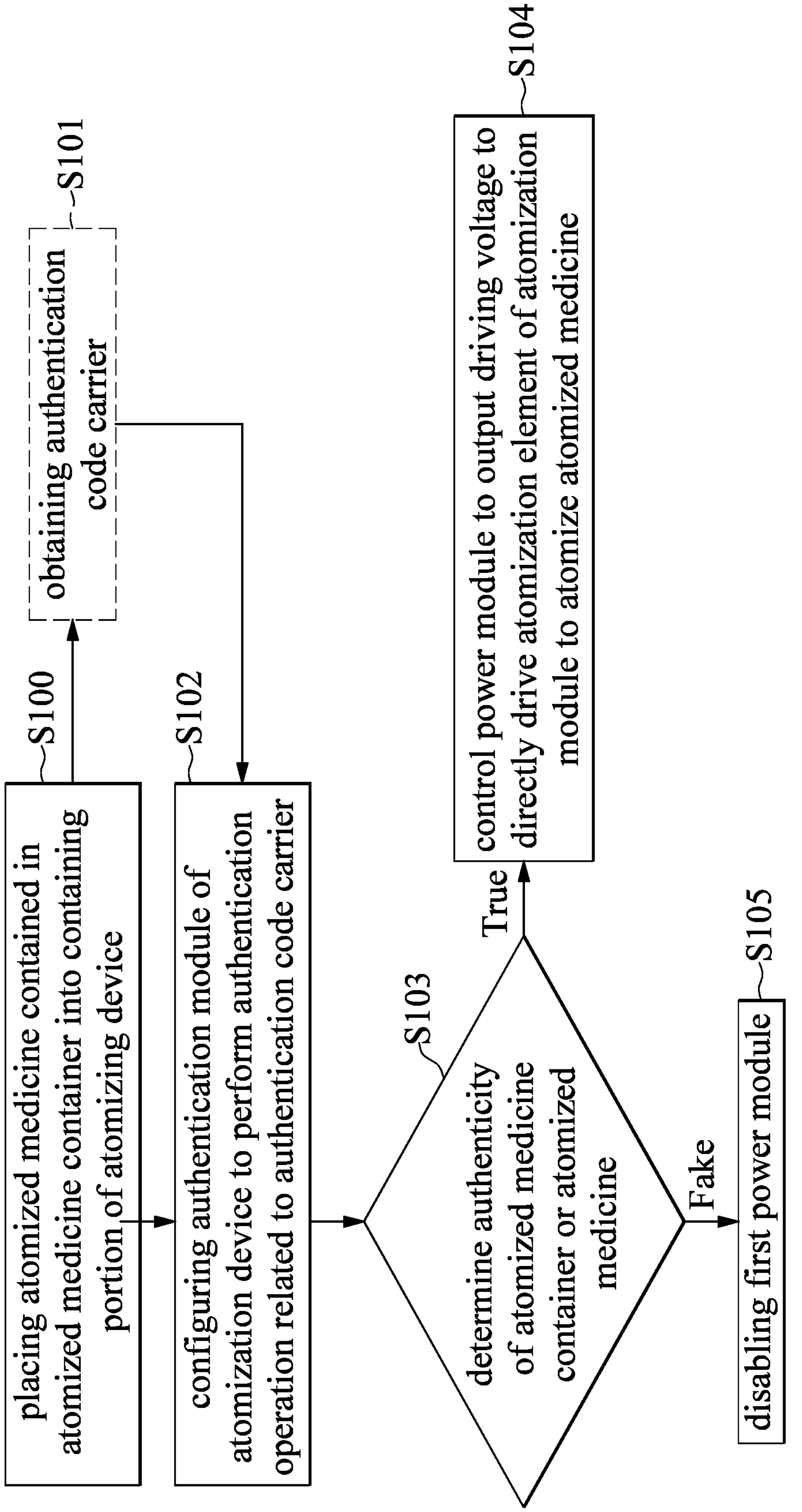
FIG. 19 is a flowchart of an atomization method having an authentication mechanism according to an eleventh embodiment of the present invention.

Reference is now made to FIG. 19, which is a flowchart of an atomization method having an authentication mechanism according to an eleventh embodiment of the present invention. As shown, the atomization method having an authentication mechanism of the present embodiment includes following steps:

Step S100: placing an atomized medicine contained in an atomized medicine container into a containing portion of an atomizing device; optionally, the user may first perform step S101 to obtain the authentication code carrier of the atomized medicine container in advance. The atomized medicine container may be a bottle container with a bottle rim, and the authentication code carrier may be an electronic tag provided on the bottle cap to be used separately from the bottle container, but the present invention is not limited thereto, and the authentication code carrier may also be an electronic tag detachably disposed outside the bottle container.

Step S102: configuring an authentication module of the atomization device to perform an authentication operation related to an authentication code carrier associated with the atomized medicine container. FIG. 1 may be referred to for the specific configuration of the atomization device, which includes an atomization module, a first power module, a control unit, an antenna module, and an authentication module. The related technical features are already described in the foregoing embodiment.

Step S103: configuring the authentication module to determine the authenticity of the atomized medicine container or the atomized medicine, and generating an authentication result signal correspondingly. In more detail, the authentication module performs the authentication operation related to the authentication code carrier belonging to the atomized medicine container, and the authenticity of the at least one atomized medicine container or the atomized medicine may be determined. The authentication operations include wireless identification, 2D barcode identification, authentication code identification, and structural lock mechanism, and the application method thereof will be described in detail hereinafter.

If the authentication module determines that the atomized medicine container is true during the authentication operation, step S104 is then executed: configuring the control unit to control the power module to output the driving voltage according to the authentication success signal to directly drive a atomization element of the atomization module to atomize the atomized medicine. If the authentication module determines that the atomized medicine container is fake during the authentication operation, step S105 is then executed: generating the corresponding authentication result signal, and disabling the first power module according to the authentication result signal by the control unit.

Twelfth Embodiment

Figure 20A:
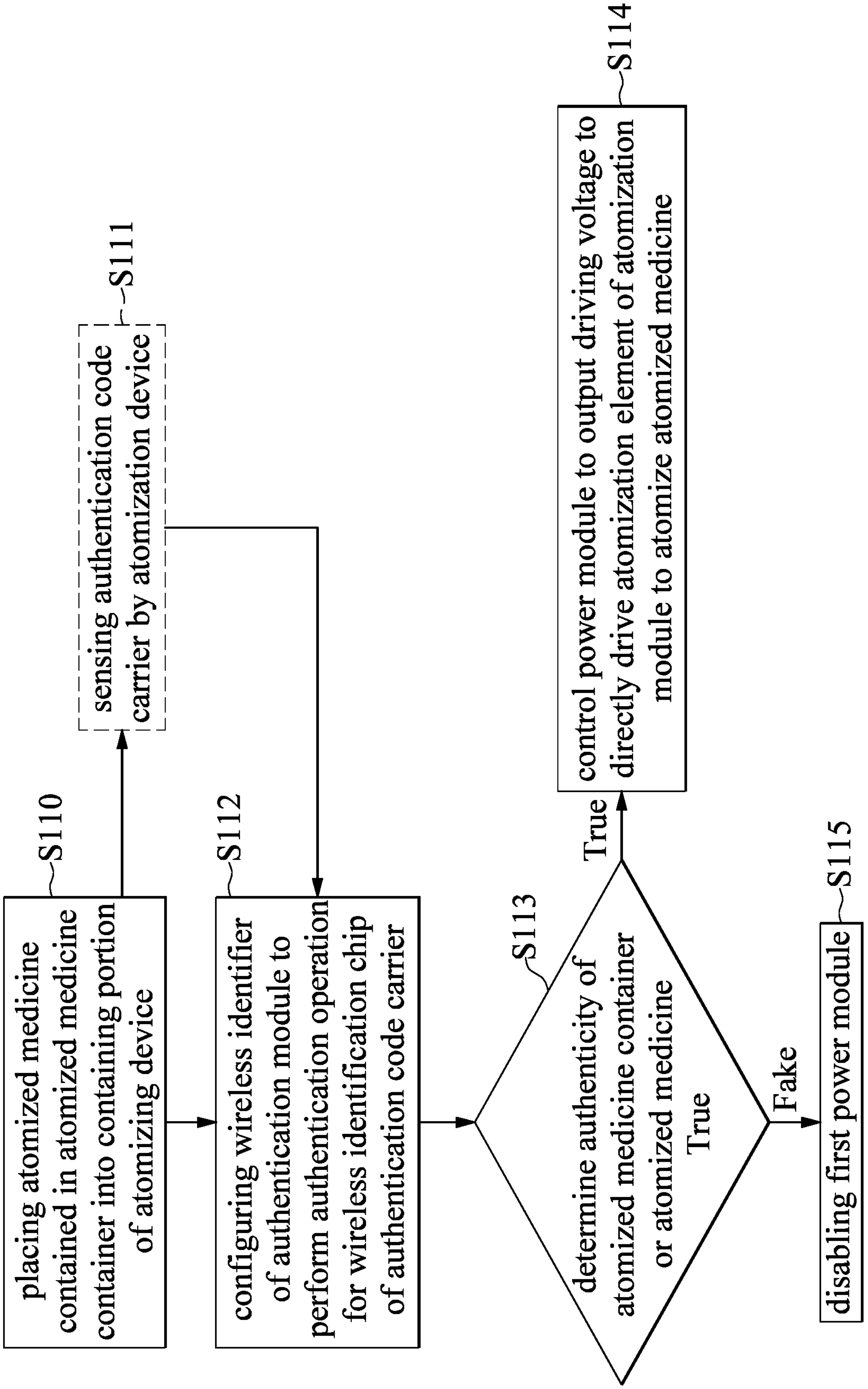
FIG. 20A is a flowchart of an atomization method having an authentication mechanism according to a twelfth embodiment of the present invention.

Reference is now made to FIG. 20A, which is a flowchart of an atomization method having an authentication mechanism according to a twelfth embodiment of the present invention. As shown, the atomization method having an authentication mechanism of the present embodiment includes the following steps:

Step S110: placing an atomized medicine contained in an atomized medicine container into a containing portion of an atomizing device; optionally, the user may first perform step S111 to sense the authentication code carrier by the atomization device.

Step S112: configuring a wireless identifier of the authentication module to perform the authentication operation for a wireless identification chip of the authentication code carrier. FIG. 2A can be further referred to for the specific configuration of the atomization device, and the authentication module includes a wireless identifier, an authentication unit, and a memory, the authentication code carrier includes a wireless identification chip and an antenna connected thereto, and the related technical features have all been described in the foregoing embodiments.

In this example, the authentication operation between the authentication module and the authentication code carrier is mainly based on the passive RFID technology, which is directly powered by the wireless identifier through the radio waves transmitted by the antenna module to the radio frequency identification tag, that is, the wireless identification chip itself, and the wireless identification chip further has authentication information 1004 written in advance.

Step S113: configuring the authentication module to determine the authenticity of the atomized medicine container or the atomized medicine, and generate an authentication result signal correspondingly. In more detail, the authentication module performs the authentication operation related to the authentication code carrier belonging to the atomized medicine container through the wireless identification. In practice, the wireless identifier may be utilized to read the authentication information previously written in the wireless identification chip. Here, the authentication information may be an anti-counterfeiting identification code having a specific coding sequence and product history data, and by utilizing the authentication unit to perform the identification, anti-fake improvements using the anti-counterfeit identification code and product history data may be effected, and the authenticity of the atomized medicine container or the atomized medicine may be determined.

If the authentication module determines that the atomized medicine container is true during the authentication operation, step S114 is then executed: configuring the control unit to control the power module to output the driving voltage according to the authentication success signal to directly drive a atomization element of the atomization module to atomize the atomized medicine. If the authentication module determines that the atomized medicine container is fake during the authentication operation, step S115 is then executed: generating the corresponding authentication result signal, and disabling the first power module according to the authentication result signal by the control unit.

In addition, in step S113, the authentication unit may further process the read anti-counterfeit identification code with a specific coding sequence, and perform a specific authentication algorithm stored in the memory to perform decryption to confirm the authenticity of the authentication code carrier having the authentication information. Another example of the processing operation performed by the authentication unit may compare a part or all of the authentication information with the data stored in the memory to confirm authenticity of the authentication code carrier. If the authenticating unit determines that the authenticating code carrier is true, it can be known that the corresponding atomized medicine container is not forged, such that the user can use it with confidence.

Figure 20B:
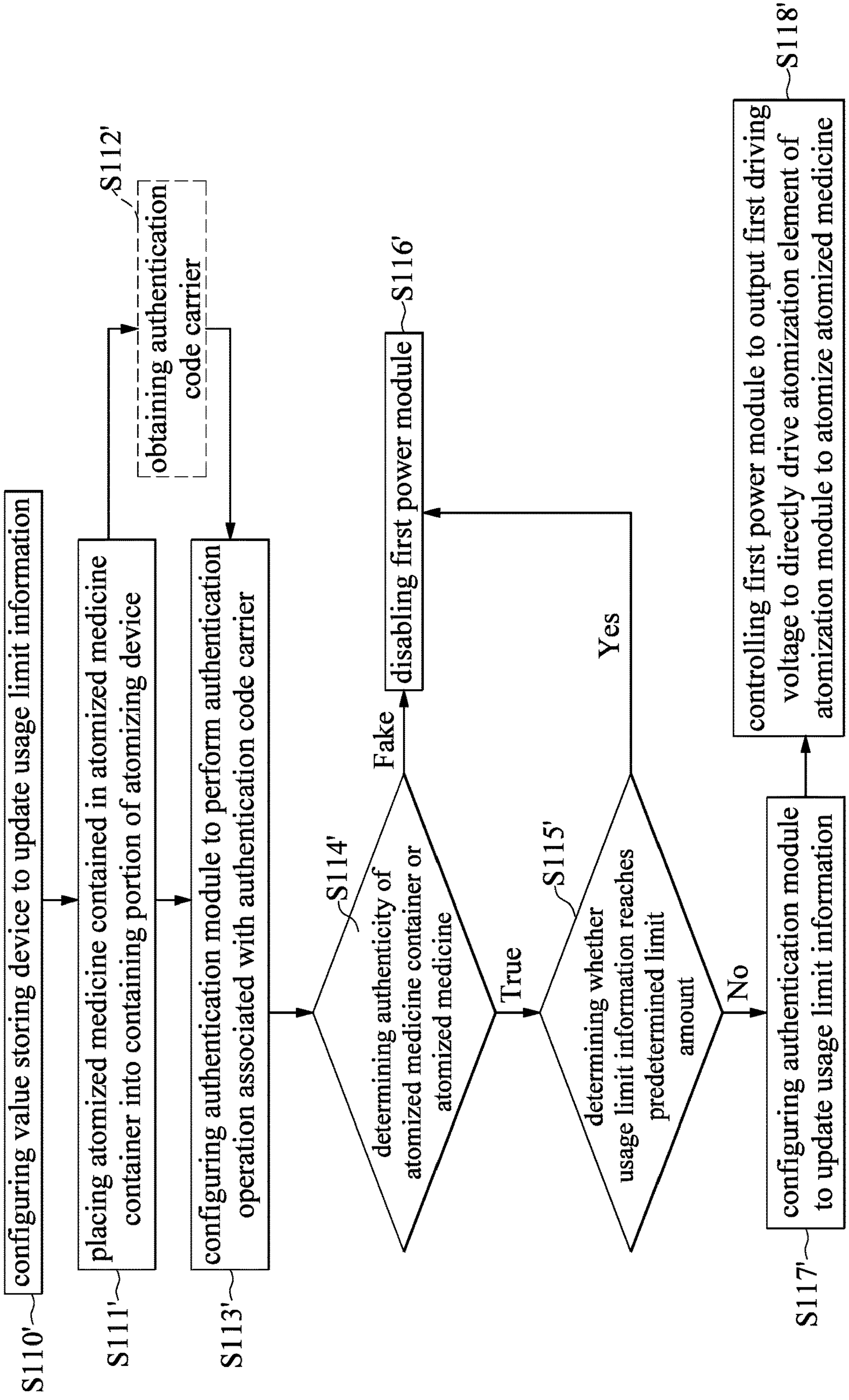
FIG. 20B is another flowchart of the atomization method having the authentication mechanism according to the twelfth embodiment of the present invention.

Reference is now made to FIG. 20B, which is another flowchart of the atomization method having the authentication mechanism according to the twelfth embodiment of the present invention. As shown, the atomization method having an authentication mechanism of the present embodiment includes following steps:

Step S110': configuring a value storing device to update the usage limit information; As previously described in FIG. 2D, when the user completes the purchase at pharmacy counter, staffs of the pharmacy may operate the value storing interface to update the usage limit information by the wireless module, for example, configuring the value storing processor to query or update the database according to the purchased barcode, and to update the usage limit information to the purchased quantity of the atomization medicine containers.

Step S111': placing an atomized medicine contained in an atomized medicine container into a containing portion of an atomizing device; optionally, the user may first perform step S112' to sense the authentication code carrier by the atomization device.

Step S113': configuring a wireless identifier of the authentication module to perform the authentication operation for a wireless identification chip of the authentication code carrier.

In this example, the authentication operation between the authentication module and the authentication code carrier is mainly based on the passive RFID technology, which is directly powered by the wireless identifier through the radio waves transmitted by the antenna module to the radio frequency identification tag, that is, the wireless identification chip itself, and the wireless identification chip further has authentication information written in advance.

Step S114': configuring the authentication module to determine the authenticity of the atomized medicine container or the atomized medicine, and generating an authentication result signal correspondingly. In more detail, the authentication module performs the authentication operation related to the authentication code carrier belonging to the atomized medicine container through the wireless identification. In practice, the wireless identifier may be utilized to read the authentication information previously written in the wireless identification chip. Here, the authentication information may be an anti-counterfeiting identification code having a specific coding sequence and product history data, and by utilizing the authentication unit to perform the identification, anti-fake improvements using the anti-counterfeit identification code and product history data may be effected, and the authenticity of the atomized medicine container or the atomized medicine may be determined.

If the authentication module determines that the atomized medicine container is true during the authentication operation, step S115' is then executed: configuring the authentication module to determine whether the usage limit information reaches a predetermined limit amount. For example, the authentication unit of the authentication module may determine whether the usage limit information has reached 0, and if yes, step S116' is executed, generating the corresponding authentication result signal to disable the control unit.

If the authentication unit of the authentication module determines that the usage limit information has not reached the predetermined limit amount in step S115', for example, more than 0 times, the method proceeds to step S117', configuring the authentication module to update the usage limit information. For example, reducing the number of uses of the authentication code carrier by one, and generating the authentication result signal to enable the control unit correspondingly.

Step S118': configuring the control unit to control the power module to output the driving voltage according to the authentication success signal to directly drive a atomization element of the atomization module to atomize the atomized medicine.

In addition, if the authentication module determines that the atomized medicine container is fake, the step S116' is similarly executed, generating the corresponding authentication result signal to disable the control unit.

With the above configuration, when the user purchases a specific number of atomized medicine containers, it can ensure that the usage limit information corresponds to the number of atomized medicine containers, and the reliability of the authentication may be further increased.

Thirteenth Embodiment

Figure 21:
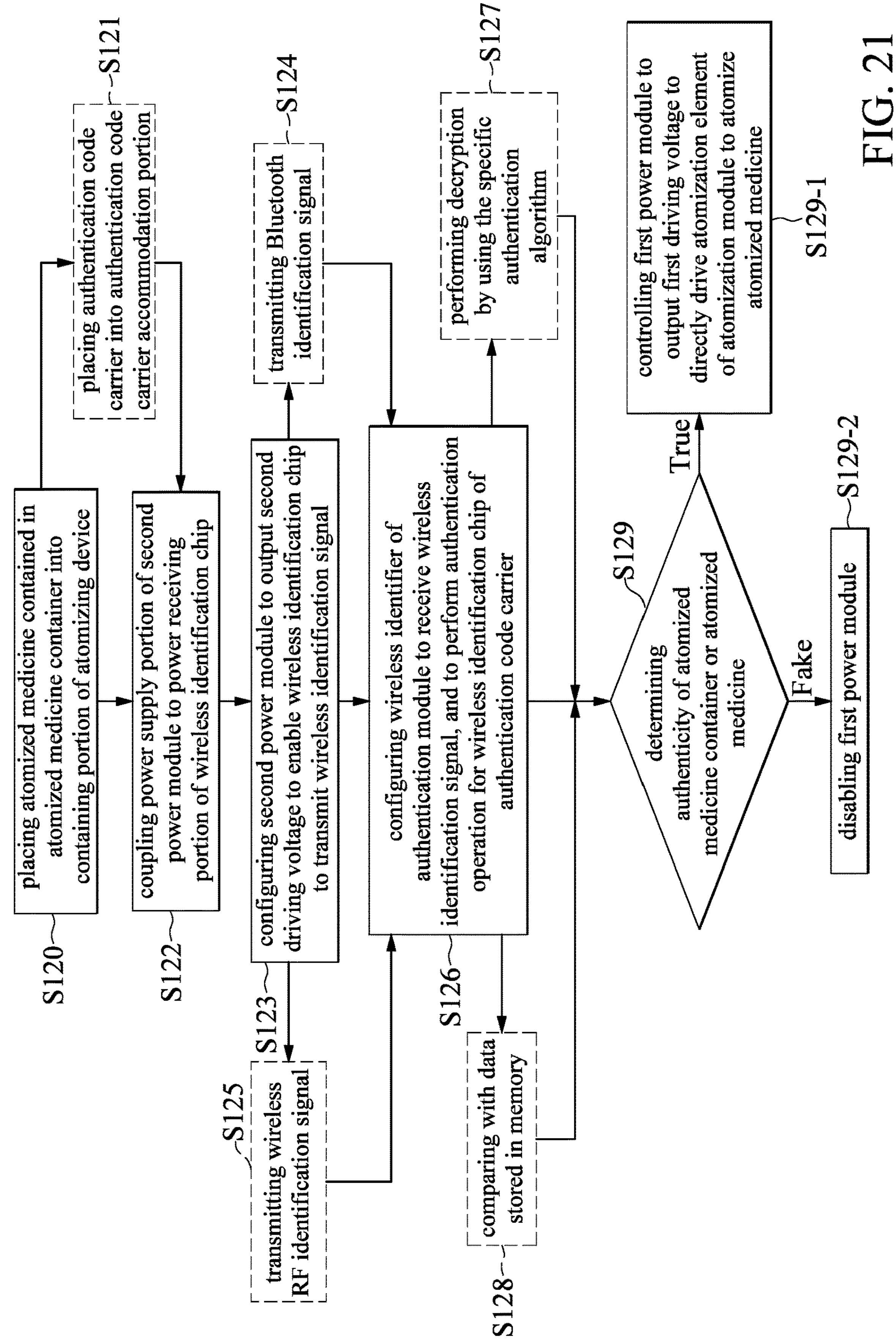
FIG. 21 is a flowchart of an atomization method with an authentication mechanism according to a thirteenth embodiment of the present invention.

Reference is now made to FIG. 21, which is a flowchart of an atomization method with an authentication mechanism according to a thirteenth embodiment of the present invention. As shown, the atomization method having an authentication mechanism of the present embodiment includes following steps:

Step S120: placing an atomized medicine contained in an atomized medicine container into a containing portion of an atomizing device; Optionally, the user may first perform step S121, placing the authentication code carrier into the authentication code carrier accommodation portion, which may provide appropriate support for securing the authentication code carrier.

In this embodiment, further reference may be made to the atomization system of FIGS. 3, 4 and 5. The atomization system further includes a second power module connected to the control unit for outputting a second driving voltage. The control unit may output one or more control signals for controlling the operation of the second power module. In addition, the atomization device further includes a power supply portion connected to the second power module, and the authentication code carrier further includes a power receiving portion connected to the wireless identification chip.

Step S122: coupling a power supply portion of the second power module to a power receiving portion of the wireless identification chip. As described in the previous embodiments, the second power module is configured to output the second driving voltage to enable the wireless identification chip when the power supply portion is electrically coupled to the power receiving portion.

Specifically, the present embodiment mainly utilizes an active type of wireless identification technology. In addition to the active type of radio frequency identification technology mentioned above, the ISM (Industrial Scientific Medical) band radio frequency identification technology such as Bluetooth wireless identification technology may be employed, and the radio frequency identification may be performed in the 2.4 GHz Industrial Scientific Medical band (ISM Band).

Furthermore, the receiving portion of the authentication code carrier may be a connector with a specific standard, and the atomization device may be further provided with an authentication code carrier accommodating portion at the position where the power supply portion disposed, and after the power receiving terminal is connected to the power supply terminal, appropriate supporting forces may be provided to stabilize the authentication code carrier, and the authentication code carrier accommodating portion may also be disposed at the outside of the atomization device corresponding to the antenna module, not only providing convenience for the user, but also ensuring that the wireless identifier may be successfully sensed with the wireless identification chip.

Step S123: configuring the second power module to output a second driving voltage to enable the wireless identification chip to transmit the wireless identification signal. In this example, the authentication operation between the authentication module 128 and the authentication code carrier 100 is mainly based on the active type of the wireless identification technology, and it may use the active type of the wireless RFID technology or the ISM (Industrial Scientific Medical) band radio frequency identification technology such as Bluetooth wireless identification technology, and the radio frequency identification may be performed in the 2.4 GHz Industrial Scientific Medical band (ISM Band). The user can select the appropriate authentication operation according to practical requirements or transmission distance. For example, the method may proceed to step S124, configuring the wireless identification chip to transmit the Bluetooth identification signal to the authentication module, or the method may proceed to step S125, configuring the wireless identification chip to transmit the wireless RF identification signal to the authentication module. In practice, the authentication information previously written in the wireless identification chip may be transmitted to the wireless identifier by the wireless identification chip with the wireless radio frequency signals or Bluetooth identification signals, so as to effect anti-fake improvements using the anti-counterfeit identification code and product history data.

Step S126: configuring a wireless identifier of the authentication module to receive the wireless identification signal, and to perform the authentication operation for a wireless identification chip of the authentication code carrier. As described in the previous embodiments, the wireless identifier may analyze the wireless radio frequency identification signal or the Bluetooth identification signal, and the authentication unit may be configured to judge the authentication information therein. Optionally, the authentication unit may further process the received anti-counterfeit identification code having the specific coding sequence, and the method may proceed to step S127, performing a decryption by using the specific authentication algorithm stored in the memory, so as to confirm the authenticity of the authentication code carrier having the authentication information. In addition, the method may proceed to step S128, configuring the authentication unit to compare a part or all of the authentication information with the data stored in the memory to confirm authenticity of the authentication code carrier.

Step S129: configuring the authentication module to determine the authenticity of the atomized medicine container or the atomized medicine, and generate an authentication result signal correspondingly. This step mainly generates the corresponding authentication result signal according to the authentication step of step S126, S127 or S128.

If the authentication module determines that the atomized medicine container is true during the authentication operation, step S129-1 is then executed: configuring the control unit to control the power module to output the driving voltage according to the authentication success signal to directly drive a atomization element of the atomization module to atomize the atomized medicine. If the authentication module determines that the atomized medicine container is fake during the authentication operation, step S129-2 is then executed: generating the corresponding authentication result signal, and disabling the first power module according to the authentication result signal by the control unit.

Fourteenth Embodiment

Figure 22:
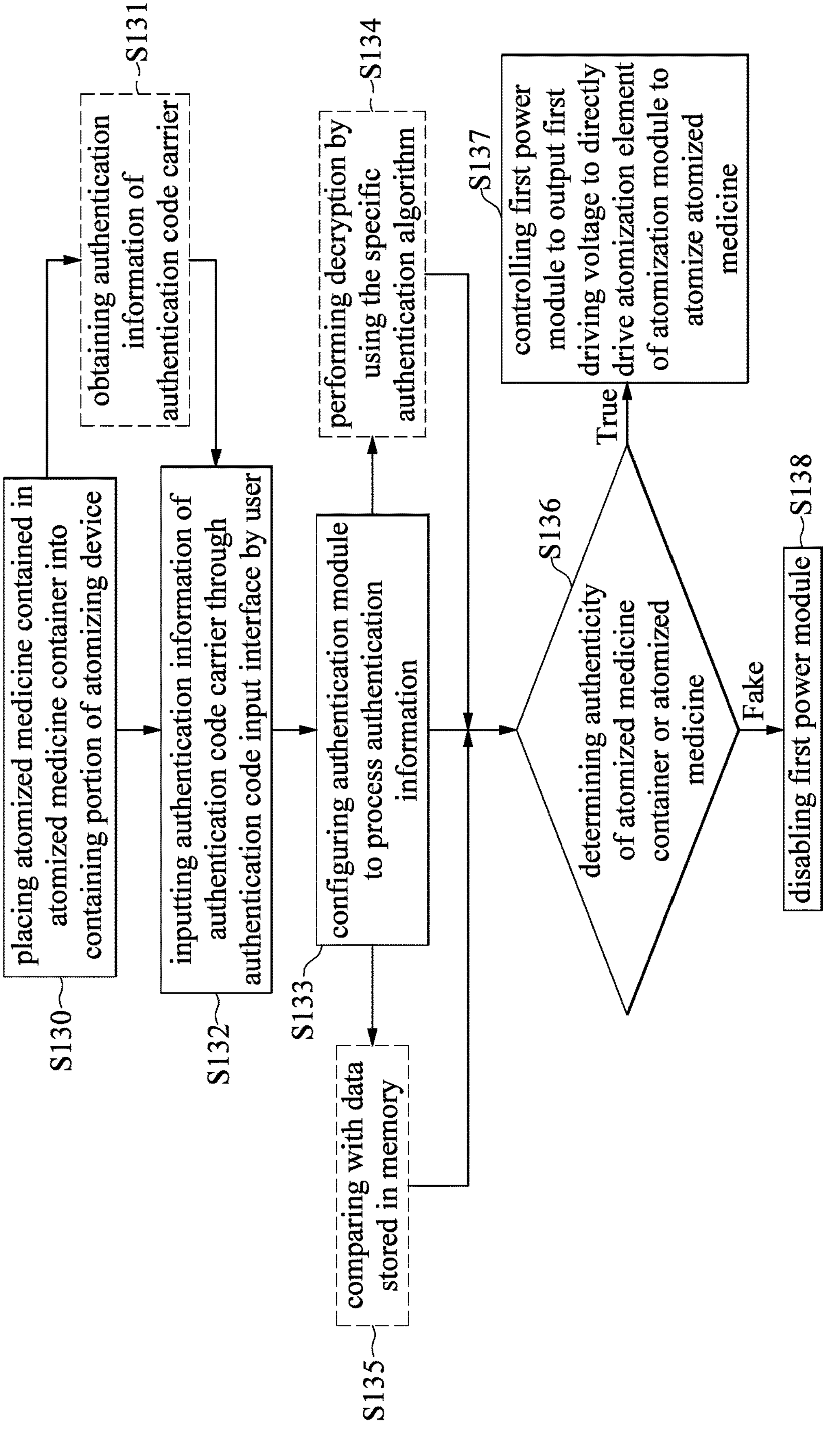
FIG. 22 is a flowchart of an atomization method with an authentication mechanism according to a fourteenth embodiment of the present invention.

Reference is now made to FIG. 22, which is a flowchart of an atomization method with an authentication mechanism according to a fourteenth embodiment of the present invention. As shown, the atomization method having an authentication mechanism of the present embodiment includes the following steps:

Step S130: placing an atomized medicine contained in an atomized medicine container into a containing portion of an atomizing device; optionally, the user may first perform step S131 to obtain the authentication code carrier of the atomized medicine container in advance. The authentication code carrier may be directly printed with the authentication information, for example, an authentication code having a specific sequence code, and may be printed at a position where the authentication code carrier is disposed, for example, inside or outside of the bottle cap or the bottle body of the atomized medicine container.

On the other hand, the atomization device used in this embodiment can be referred to in FIGS. 6 and 7 and its related embodiments. The atomization device is generally equipped with a user interface, and the user device 14 may include the above-mentioned authentication code input interface, and a control interface for the user to control the atomization module. The authentication code input interface and control interface can be configured with a display screen, and physical keys or virtual keys displayed on the display screen may be utilized, and the present embodiment does not limit the manner of implementation of the interfaces.

Step S132: inputting the authentication information of the authentication code carrier through the authentication code input interface by the user. For example, the user can directly input the authentication code printed on the inside of the bottle cap through the authentication code input interface, and the authentication code can be correspondingly displayed on the display screen for the user to confirm.

Step S133, configuring the authentication module to process the authentication information. After the user inputs the authentication information, the authentication module may further process the authentication information input by the user, for example, authentication codes. Optionally, the method may proceed to step S134, using the authentication unit to further process the read anti-counterfeit identification code with a specific coding sequence input by the user, and to execute a specific authentication algorithm stored in the memory to perform decryption to confirm the authenticity of the authentication code carrier having the authentication information 1004. Another example of the processing operation performed by the authentication unit includes proceeding to step S135, comparing a part or all of the authentication information with the data stored in the memory to confirm authenticity of the authentication code carrier.

Step S136: configuring the authentication module to determine the authenticity of the atomized medicine container or the atomized medicine, and generate an authentication result signal correspondingly. This step mainly generates the corresponding authentication result signal according to the authentication step of step S133, S134 or S135.

If the authentication module determines that the atomized medicine container is true during the authentication operation, the method proceeds to step S137: configuring the control unit to control the power module to output the driving voltage according to the authentication success signal to directly drive a atomization element of the atomization module to atomize the atomized medicine. If the authentication module determines that the atomized medicine container is fake during the authentication operation, the method proceeds to step S138: generating the corresponding authentication result signal, and disabling the first power module according to the authentication result signal by the control unit.

Fifteenth Embodiment

Figure 23:
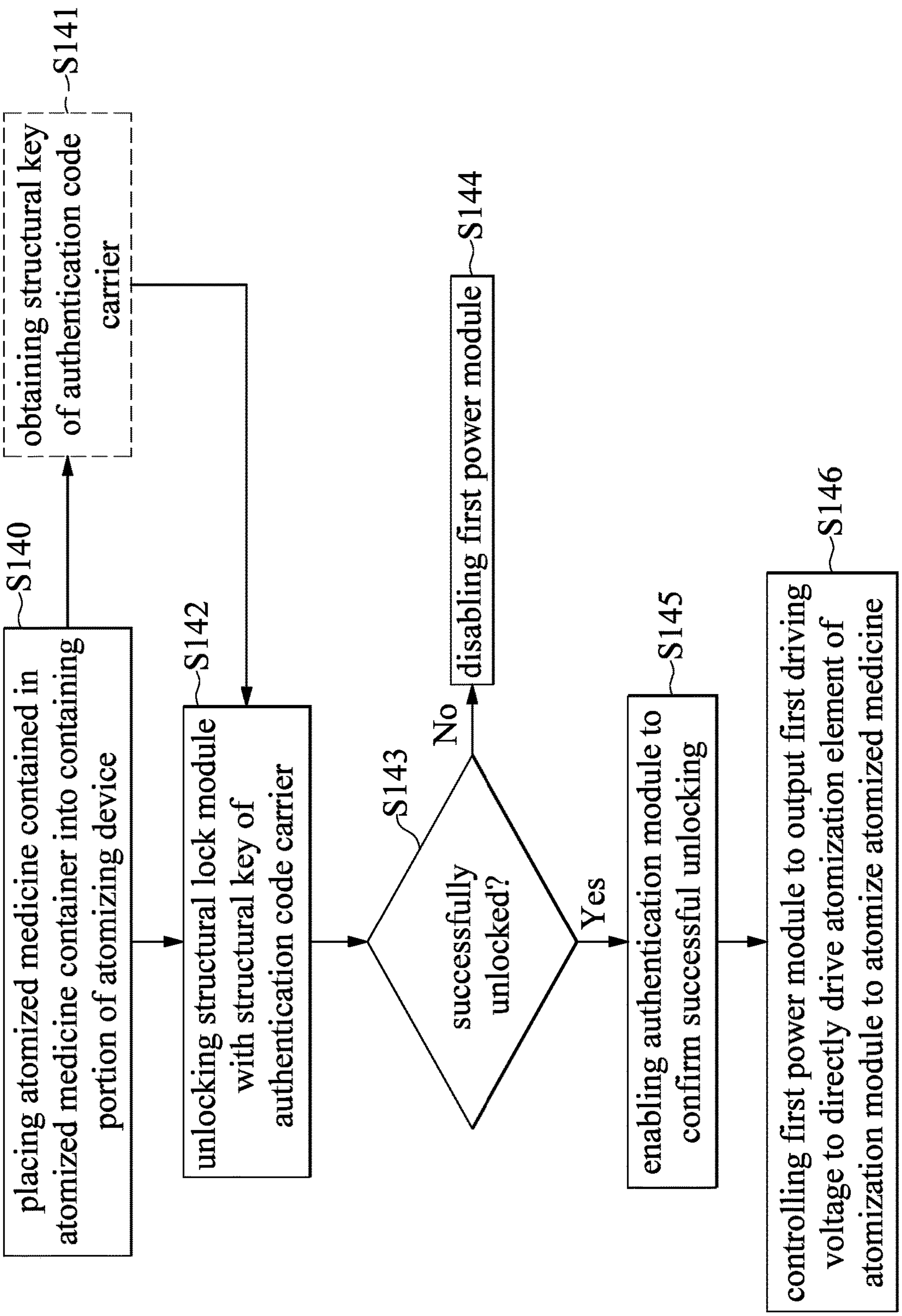
FIG. 23 is a flowchart of an atomization method having an authentication mechanism according to a fifteenth embodiment of the present invention.

Reference is now made to FIG. 23, which is a flowchart of an atomization method having an authentication mechanism according to a fifteenth embodiment of the present invention. As shown, the atomization method having an authentication mechanism of the present embodiment includes following steps:

Step S140: placing an atomized medicine contained in an atomized medicine container into a containing portion of an atomizing device; the specific configuration of the atomization device can refer to FIG. 8 and FIG. 9, which further includes a structural lock module connected with the authentication module, and the authentication code carrier further includes a structural key. The structural lock module includes a structural lock 160 and an electronic switch.

Optionally, the user may first perform step S141 to obtain the structural key on the authentication code carrier in advance. The structural key can be disposed inside the bottle cap served as the authentication code carrier 100, the structural key 18 and the structural lock 160 on the atomization device 12 provided by the manufacturer may be consistent in terms of commercial nature to provide the first level of security.

Step S142: unlocking a structural lock module with the structural key of the authentication code carrier.

Step S143: determining whether the structural lock module is unlock success, if not, the method proceed to step S144, configuring the electronic switch or the authentication module to disable the first power module through the control module. If yes, the method proceed to step S145, configuring the electronic switch to enable the authentication module to confirm successful unlocking. In detail, after the user successfully unlocks the structural lock with the structural key, the electronic switch will transmit a start up signal to enable the authentication module.

After the authentication module receives the start up signal, step S146 may be further performed by the control unit: controlling the power module to output the driving voltage to directly drive the atomization element of the atomization module to atomize the atomized medicine.

On the other hand, the authentication code carrier may have an authentication chip provided for the wireless identification module to perform the identification, the authentication module may further obtain the authentication information through the antenna module, and perform the authentication operation according to the third embodiment. For example, comparing the authentication information with the data stored in the memory, or the obtained authentication information is an anti-counterfeiting identification code having a specific coding sequence so that a specific algorithm stored in the memory may be further executed for decryption to determine the authenticity of the atomized medicine container or the atomized medicine. In this way, a second level of security can be provided.

Therefore, this embodiment can provide double guarantees of the structural key and the wireless identification, which not only ensures safety, but also increases the difficulty of forging atomized medicine containers.

Sixteenth Embodiment

Another aspect of the atomization method with the authentication mechanism of the present invention will be described in detail hereinafter while making reference to the accompanying drawings. In the present embodiment, the atomization method with the authentication mechanism is mainly applicable to the fifth, sixth, and seventh embodiments, but is not limited thereto, and the present embodiment may be implemented in a manner that can be considered by those skilled in the arts. The method provided by the present embodiment may also applicable to any of the embodiments described above.

Figure 24A:
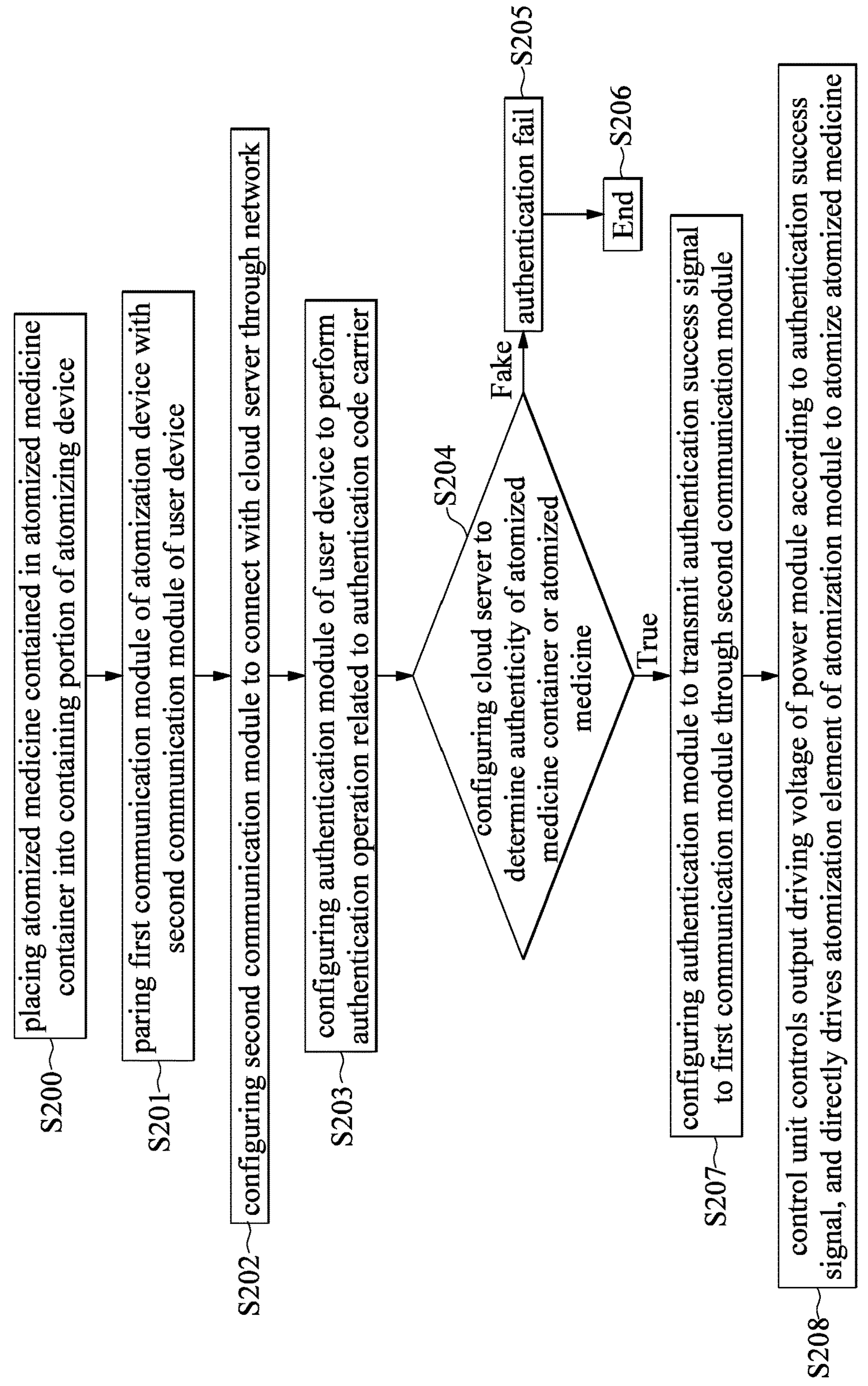
FIG. 24A is a flowchart of an atomization method having an authentication mechanism according to the sixteenth embodiment of the present invention.

Reference is now made to FIG. 24A, which is a flowchart of an atomization method having an authentication mechanism according to a sixteenth embodiment of the present invention. As shown, the atomization method having an authentication mechanism of the present embodiment includes following steps:

Step S200: placing an atomized medicine contained in an atomized medicine container into a containing portion of an atomizing device; optionally, the user may first obtain the authentication code carrier of the atomized medicine container in advance. Specific configurations of the atomization device, the cloud server, the user device and the atomized medicine container can be seen in FIG. 10. The atomization device includes an atomization module, a power module, a control unit, and a first communication module. The user device includes a processor, a second communication module, and an authentication module. The related technical features are already described in the foregoing embodiment.

Step S201: Pairing the first communication module of the atomization device with the second communication module of the user device. The pairing of the first communication module and the second communication module can be transmitted through the near-end network, such as WIFI, Bluetooth, etc. More specifically, the user device can obtain administrator rights of the atomization device through the pairing operation, such that wireless controls and authentication mechanisms may be achieved.

Step S202: configuring the second communication module to connect with the cloud server through the network. In this embodiment, the authentication operation is mainly performed on the user device and the cloud server, and the atomization device may not need to be provided with an authentication module and its related device or system, which can save the manufacturing cost.

Step S203: configuring the authentication module of the user device to perform an authentication operation related to an authentication code carrier. Specifically, the authentication operation between the authentication module 228 and the authentication code carrier 200 may utilize the radio frequency identification (RFID), which is mainly composed of radio frequency tag (RFID tag), reader or barcode reader and related application system.

Step S204: configuring the cloud server to determine the authenticity of the atomized medicine container or the atomized medicine, and to generate an authentication result signal. If the cloud server determines that the atomized medicine container is true, the corresponding authentication result signal is generated and transmitted to the user device, the method proceeds to step S207, configuring the authentication module to transmit the authentication success signal to the first communication module through the second communication module, and the method proceeds to step 208, the control unit controlling the output driving voltage of the power module according to the authentication success signal, and directly driving the atomization element of the atomization module to atomize the atomized medicine.

If the cloud server determines that the atomized medicine container is fake in step S204, a corresponding authentication result signal is generated and transmitted to the user device. The method proceeds to step S205, the authentication fails, and the authentication failure message may be displayed on the user device. The method proceeds to step S206, where the process comes to an end. Details of the authentication operation will be described in more detail hereinafter.

Figure 24B:
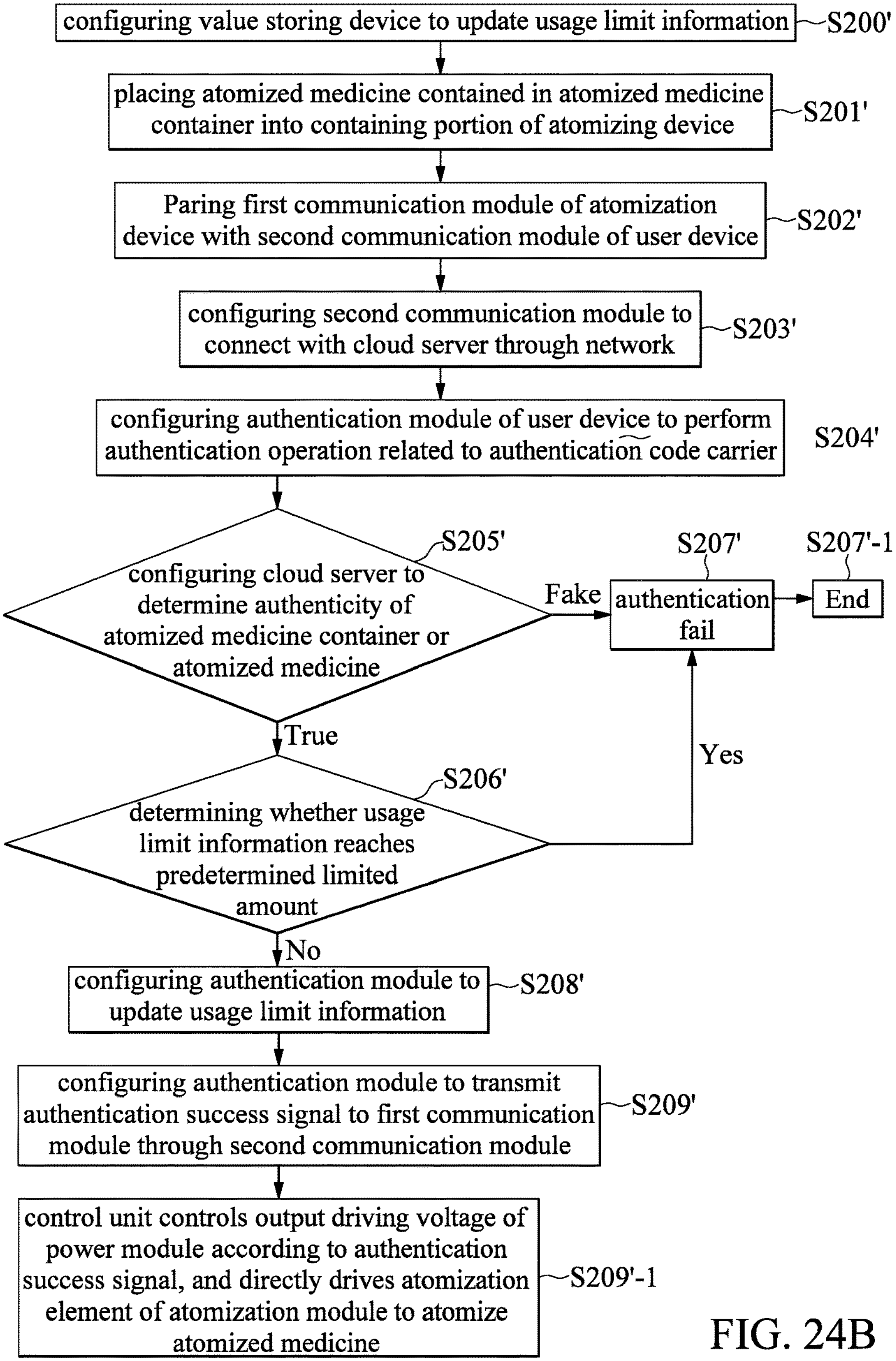
FIG. 24B is another flowchart of the atomization method having the authentication mechanism according to the sixteenth embodiment of the present invention.

Reference is now made to FIG. 24B, which is another flowchart of the atomization method having the authentication mechanism according to the sixteenth embodiment of the present invention. As shown, the atomization method having an authentication mechanism of the present embodiment includes following steps:

Step S200': configuring a value storing device to update the usage limit information; As previously described in FIG. 11B, when the user completes the purchase at pharmacy counter, staffs of the pharmacy may operate the value storing interface to update the usage limit information by the wireless value storing module, for example, configuring the value storing processor to query or update the database according to the purchased barcode, and to update the usage limit information to the purchased quantity of the atomization medicine containers. The value storing device may directly update the usage limit information in the authentication code carrier by the wireless value storing module, or directly store the usage limit information in the user device through the wireless value storing module directly after the user completes the purchase procedure at the pharmacy counter.

Step S201': placing an atomized medicine contained in an atomized medicine container into a containing portion of an atomizing device; optionally, the user may first obtain the authentication code carrier of the atomized medicine container in advance.

Step S202': Pairing the first communication module of the atomization device with the second communication module of the user device.

Step S203': configuring the second communication module to connect with the cloud server through the network. In this embodiment, the authentication operation is mainly performed on the user device and the cloud server, and the atomization device may not need to be provided with an authentication module and its related device or system, which can save the manufacturing cost.

Step S204': configuring the authentication module of the user device to perform an authentication operation related to an authentication code carrier.

Step S205': configuring the cloud server to determine the authenticity of the atomized medicine container or the atomized medicine, and to generate an authentication result signal. If the cloud server determines that the atomized medicine container is true, a corresponding authentication result signal is generated and transmitted to the user device. The method proceeds to step S206', configuring the authentication module to determine whether the usage limit information reaches a predetermined limited amount. For example, the authentication unit of the authentication module may determine whether the usage limit information has reached 0, and if yes, step S207' is executed, generating the corresponding authentication result signal to disable the control unit.

If the authentication module determines that the usage limit information has not reached the predetermined limit amount in step S206', for example, more than 0 times, the method proceeds to step S208', configuring the authentication module to update the usage limit information. For example, reducing the number of uses of the authentication code carrier by one, and generating the authentication success signal correspondingly.

Step S209', configuring the authentication module to transmit the authentication success signal to the first communication module through the second communication module, and the method proceeds to step 209'-1, the control unit controlling the output driving voltage of the power module according to the authentication success signal, and directly driving the atomization element of the atomization module to atomize the atomized medicine.

If the cloud server determines that the atomized medicine container is fake in step S205', a corresponding authentication result signal is generated and transmitted to the user device. The method proceeds to step S207', the authentication fails, and the authentication failure message may be displayed on the user device. The method proceeds to step S207'-1, the flow ends.

With the above configuration, when the user purchases a specific number of atomized medicine containers, it can ensure that the usage limit information corresponds to the number of atomized medicine containers, and the reliability of the authentication may be further increased.

Seventeenth Embodiment

Figure 25:
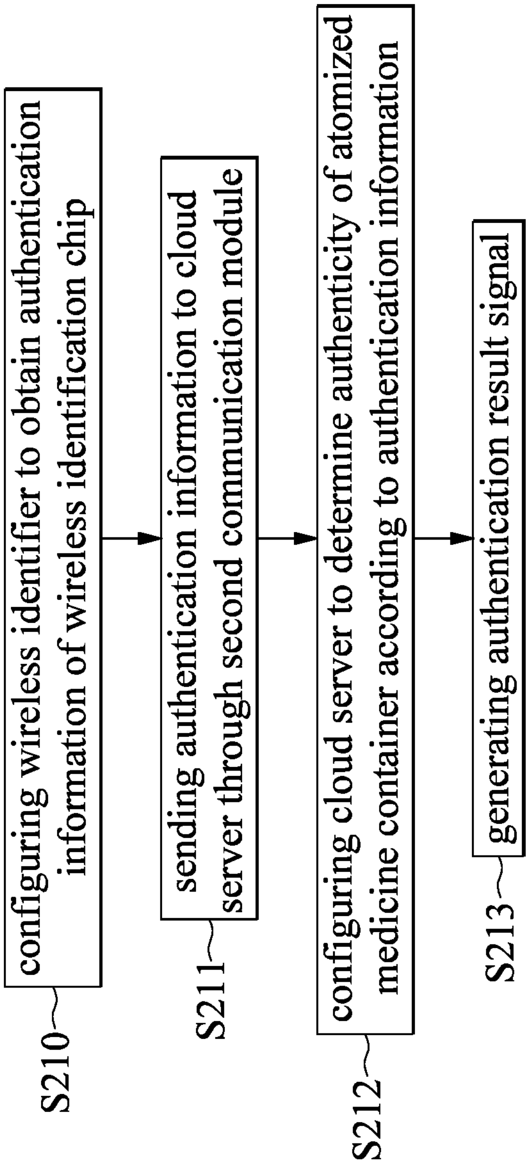
FIG. 25 is a flowchart of an authentication operation of a seventeenth embodiment of the present invention.

Reference is now made to FIG. 25, which is a flowchart of an authentication operation of a seventeenth embodiment of the present invention. This embodiment is mainly to exemplify the details of the authentication process described from step S203 to step S204 in the atomization method of the previous embodiment, the method may further include the following steps:

Step S210: configuring a wireless identifier to obtain authentication information of the wireless identification chip. In this example, the authentication operation between the authentication module and the authentication code carrier is mainly based on the passive RFID technology, which is directly powered by the wireless identifier through the radio waves transmitted by the second communication module to the radio frequency identification tag, that is, the wireless identification chip itself, and obtain the authentication information previously written in the wireless identification chip.

Step S211: sending the authentication information to the cloud server through the second communication module. Here, the authentication operation for determining the authenticity of the authentication information is mainly performed by the cloud server. After the authentication unit reads the wireless identification chip, the authentication information may be obtained, which may be an anti-counterfeit identification code having a specific coding sequence, and is transmitted to the cloud server through the second communication module.

Step S212: configuring the cloud server to determine the authenticity of the atomized medicine container or the atomized medicine according to the authentication information. The built-in processor of the cloud server can execute a specific decryption algorithm to confirm the authenticity of the authentication code carrier having the authentication information. In addition, another example of the authentication operation performed by the cloud server may compare a part or all of the authentication information with the data stored in the password database to confirm the authenticity of the authentication code carrier.

Step S213: generating an authentication result signal.

If the cloud server determines that the authenticating code carrier is true, it can be known that the corresponding atomized medicine container is not forged, such that the user can use it with confidence.

Eighteenth Embodiment

Figure 26:
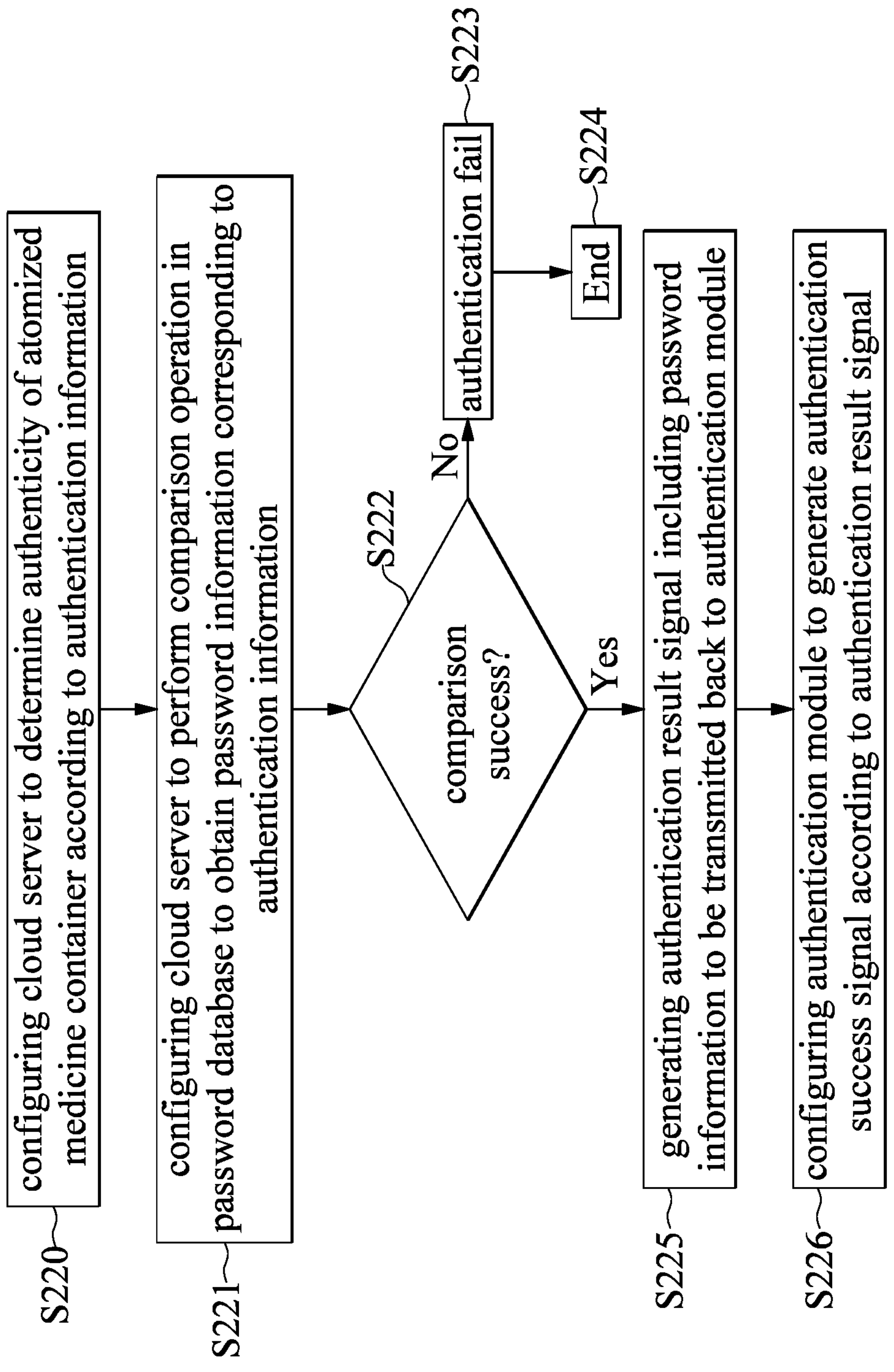
FIG. 26 is a flowchart of an authentication operation of the eighteenth embodiment of the present invention.

Reference is now made to FIG. 26, which is a flowchart of an authentication operation of the eighteenth embodiment of the present invention. This embodiment is mainly to exemplify the details of the authentication process described in step S204 in the atomization method of the previous embodiment, the method may further include the following steps:

Step S220: configuring the cloud server to determine the authenticity of the atomized medicine container or the atomized medicine according to the authentication information.

Step S221: configuring the cloud server to perform a comparison operation in a password database to obtain password information corresponding to the authentication information.

Specifically, the password database may be pre-established according to a list of products sold by a pharmaceutical supplier, and the password database may have a plurality of unique authentication information, and multiple and unique passwords corresponding to the authentication information. After the cloud server receives the read authentication information, the cloud server then performs a comparison operation in the password database according to the authentication information to obtain password information corresponding to the authentication information. Since the password database may be instantly updated by the supplier, it may be ensured that the atomized medicine containers purchased by users have not been used and faked.

After the above authentication operation, if the comparison operation of the cloud server succeeds in obtaining the password information, the method proceeds to step S225, the authentication result signal including the password information may be transmitted back to the authentication module. In the user device, the authentication unit of the authentication module may process the authentication result signal to control the second communication module to transmit the authentication success signal to the first communication module through the processor.

In detail, the password information included in the authentication result signal can be used by the authentication unit for decryption, so as to confirm that the authentication result signal is indeed from the cloud server, or to identify the encrypted authentication result signal. These security mechanisms may also prevent persons of interest from intercepting, analyzing or cracking the signals. After being processed by the authentication unit, the method may proceed to step S226, configuring the authentication module to generate the authentication success signal according to the authentication result signal. Specifically, the authentication module may control the second communication module to transmit the authentication success signal to the first communication module through the processor.

If the cloud server determines that the atomized medicine container is fake in step S221, a corresponding authentication result signal is generated and transmitted to the user device. The method proceeds to step S223, the authentication fails, and the authentication failure message may be displayed on the user device. The method proceeds to step S224, the flow ends.

The double authentication mechanism provided by the present embodiment may greatly increase the difficulty of counterfeiting the authentication code carrier, so as to ensure the security of data transmission, such that the counterfeit goods are not able to be used by the atomization device even if they are sold in the market, thus protecting the lives and property of consumers.

Nineteenth Embodiment

Figure 27:
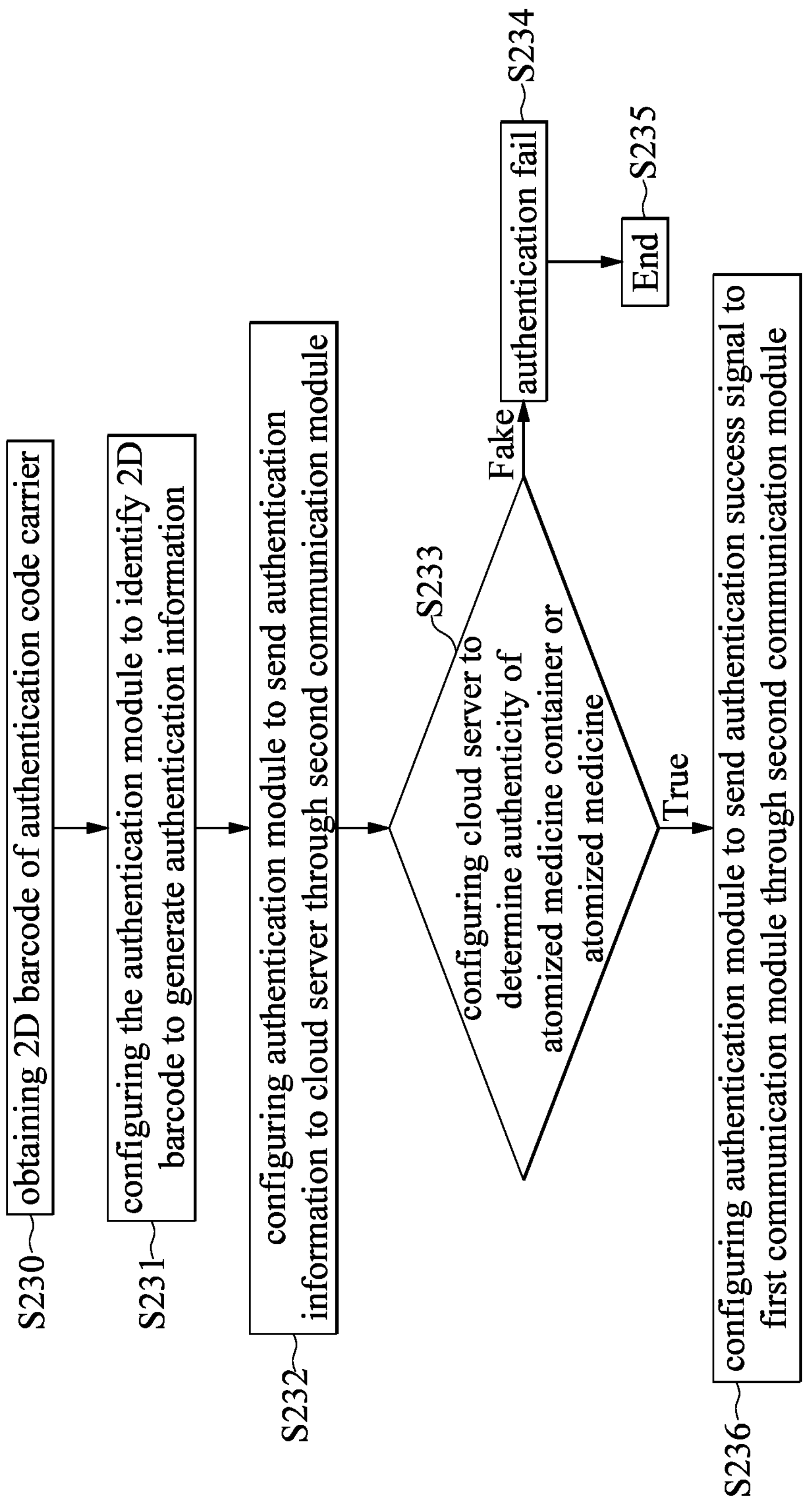
FIG. 27 is a flowchart of an authentication operation of the nineteenth embodiment of the present invention.

Reference is now made to FIG. 27, which is a flowchart of an authentication operation of the nineteenth embodiment of the present invention. This embodiment is mainly to exemplify the details of the authentication process described from step S203 to step S204 in the atomization method of the previous embodiment, the method may further include the following steps:

Step S230: obtaining the 2D barcode of the authentication code carrier. For the specific configuration of the user device and the authentication code carrier, reference may be made to FIG. 12, the user device further includes an image capturing module connected to the authentication unit, and the authentication code carrier further includes a two-dimensional barcode. The two-dimensional barcode of the authentication code carrier may be directly printed at a position where the authentication code carrier is disposed, for example, inside or outside of the bottle cap or the bottle body of the atomized medicine container.

Step S231: configuring the authentication module to identify a two-dimensional barcode to generate authentication information. The user may obtain the image of the 2D barcode through the image capturing module, and analyze the 2D barcode through the authentication unit to obtain the authentication information. Specifically, this embodiment provides another implementation for obtaining the authentication information, which utilizes a camera that is commonly provided in an existing smart phone, and also improves the convenience of the authentication. The production costs may be further reduced when compared with the previous embodiment in which the wireless identification chip is provided.

Step S232: configuring the authentication module to send the authentication information to the cloud server through the second communication module. Here, the authentication operation for determining the authenticity of the authentication information is mainly performed by the cloud server. After the authentication unit analyzes the 2D barcode to obtain the authentication information, it can be transmitted to the cloud server through the second communication module.

Step S233: configuring the cloud server to determine the authenticity of the atomized medicine container or the atomized medicine according to the authentication information, and to generate the authentication result signal. The built-in processor of the cloud server can execute a specific decryption algorithm to confirm the authenticity of the 2D barcode having the authentication information. In addition, another example of the authentication operation performed by the cloud server may compare a part or all of the authentication information with the data stored in the password database to confirm the authenticity of the authentication code carrier. If the cloud server determines that the authenticating code carrier is true, it can be known that the corresponding atomized medicine container is not forged, such that the user can use it with confidence.

If the cloud server determines that the atomized medicine container is true, a corresponding authentication result signal is generated and transmitted to the user device. The method proceeds to step S236, configuring the authentication module to determine whether the usage limit information reaches a predetermined limited amount.

If the cloud server determines that the atomized medicine container is fake in step S233, a corresponding authentication result signal is generated and transmitted to the user device. The method proceeds to step S234, the authentication fails, and the authentication failure message may be displayed on the user device. The method proceeds to step S235, where the process comes to an end.

Twentieth Embodiment

Figure 28:
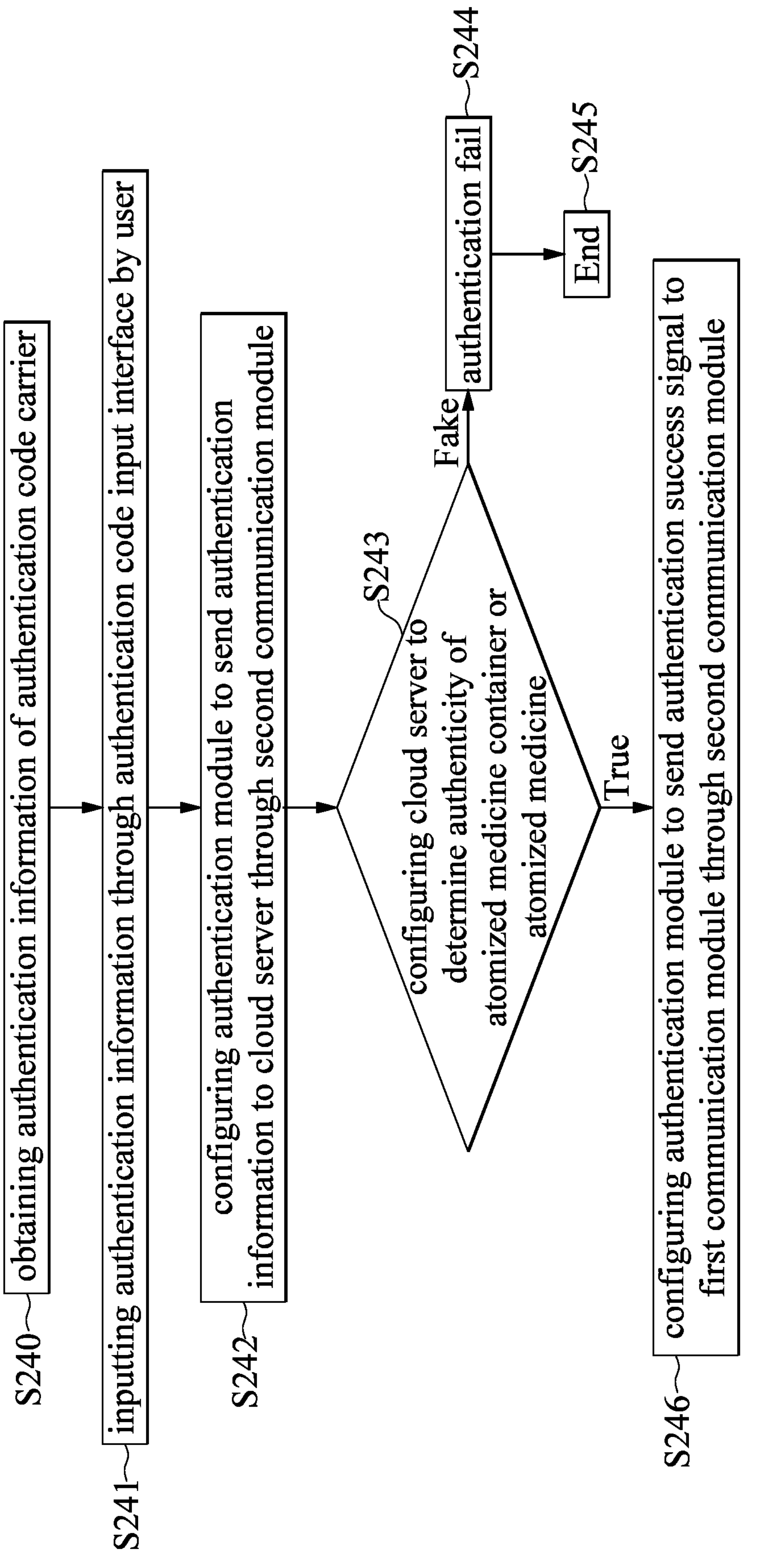
FIG. 28 is a flowchart of an authentication operation of the twentieth embodiment of the present invention.

Reference is now made to FIG. 28, which is a flowchart of an authentication operation of the twentieth embodiment of the present invention. This embodiment is mainly to exemplify the details of the authentication process described from step S203 to step S204 in the atomization method of the previous embodiment, the method may further include the following steps:

Step S240: obtaining the authentication information of the authentication code carrier. For the specific configuration of the user device and the authentication code carrier, reference may be made to FIG. 13, the user device further includes an authentication code input interface connected to the authentication unit. The authentication code carrier may be directly printed with the authentication information, for example, an authentication code having a specific sequence code, and may be printed at a position where the authentication code carrier is disposed, for example, inside or outside of the bottle cap or the bottle body of the atomized medicine container.

Step S241: inputting the authentication information of the authentication code carrier through the authentication code input interface by the user. The user can directly input the authentication code (i.e., authentication information) through the authentication code input interface, and the authentication code can be correspondingly displayed on the display screen commonly provided in the user device for the user to confirm.

After the user inputs the authentication code (i.e., the authentication information) through the authentication code input interface, the authentication unit directly obtains the authentication information, or obtains the authentication information by decrypting the authentication code. Specifically, this embodiment provides another implementation for obtaining the authentication information, which utilizes a user interface that is commonly provided in an existing smart phone, and also improves the convenience of the authentication. The production costs may be further reduced when compared with the previous embodiment in which the wireless identification chip is provided.

Step S242: configuring the authentication module to send the authentication information to the cloud server through the second communication module. Here, the authentication operation for determining the authenticity of the authentication information is mainly performed by the cloud server. After the authentication unit obtains the authentication information, it can be transmitted to the cloud server through the second communication module.

Step S243: configuring the cloud server to determine the authenticity of the atomized medicine container or the atomized medicine according to the authentication information, and to generate the authentication result signal. The built-in processor of the cloud server can execute a specific decryption algorithm to confirm the authenticity of the authentication code carrier having the authentication information. In addition, another example of the authentication operation performed by the cloud server may compare a part or all of the authentication information with the data stored in the password database to confirm the authenticity of the authentication code carrier. If the cloud server determines that the authenticating code carrier is true, it can be known that the corresponding atomized medicine container is not forged, such that the user can use it with confidence.

If the cloud server determines that the atomized medicine container is true, a corresponding authentication result signal is generated and transmitted to the user device. The method proceeds to step S246, configuring the authentication module to determine whether the usage limit information reaches a predetermined limited amount.

If the cloud server determines that the atomized medicine container is fake in step S243, a corresponding authentication result signal is generated and transmitted to the user device. The method proceeds to step S244, the authentication fails, and the authentication failure message may be displayed on the user device. The method proceeds to step S245, the flow ends.

Similarly, after the cloud server receives the read authentication information, the cloud server then performs a comparison operation in the password database according to the authentication information to obtain password information corresponding to the authentication information. Since the password database may be instantly updated by the supplier, it can be ensured that the atomized medicine containers purchased by users have not been used and faked.

Twenty-First Embodiment

Yet another aspect of the atomization method with the authentication mechanism of the present invention will be described in detail hereinafter with reference made to the accompanying drawings. In the present embodiment, the atomization method with the authentication mechanism is mainly applicable to the eighth embodiment to the tenth embodiment, but is not limited thereto, and the present embodiment may be implemented in a manner that can be considered by those skilled in the arts. The method provided by the present embodiment may also applicable to any of the embodiments described above.

Reference is now made to FIG. 29, which is a flowchart of an atomization method having an authentication mechanism according to a twenty-first embodiment of the present invention. As shown, the atomization method having an authentication mechanism of the present embodiment includes following steps:

Step S250: placing an atomized medicine contained in an atomized medicine container into a containing portion of an atomizing device; optionally, the user may first obtain the authentication code carrier of the atomized medicine container in advance. The specific configuration of the atomization device, the cloud server, the user device, and the atomization medicine container can be referred to in FIG. 14. The atomization device includes an atomization module, a power module, a control unit, a first authentication module, and an antenna module. The user device includes a processor, a second communication module, and an authentication module. The related technical features are already described in the foregoing embodiment.

Step S251: configuring the communication module to connect with the cloud server through the network. In this embodiment, in addition to the authentication operation performed on the user device and the cloud server, another authentication operation is performed on the atomization device.

It should be noted that the functions and characteristics of the second authentication module are basically similar to those of the authentication module in the sixteenth embodiment, and the first authentication operation performed by the second authentication module interacts with the authentication code carrier, and the authentication operation for determining the authenticity of the authentication code carrier through the cloud server are also the same, so that repeated descriptions are omitted herein.

Step S252: configuring the second authentication module of the user device to perform an authentication operation related to an authentication code carrier. Specifically, the authentication operation between the second authentication module and the authentication code carrier may utilize the radio frequency identification (RFID), which is mainly composed of radio frequency tag (RFID tag), reader or barcode reader and related application system. The method may proceed to step S253 in advance: configuring a second wireless identifier of the second authentication module to obtain authentication information of the wireless identification chip. In this example, the authentication operation between the second authentication module and the authentication code carrier is mainly based on the passive RFID technology, which is directly powered by the wireless identifier through the radio waves transmitted by the second communication module to the radio frequency identification tag, that is, the wireless identification chip itself, and obtain the authentication information previously written in the wireless identification chip.

After the second authentication unit reads the wireless identification chip, the authentication information may be obtained, which may be an anti-counterfeit identification code having a specific coding sequence, and is transmitted to the cloud server through the communication module. The built-in processor of the cloud server can execute a specific decryption algorithm to confirm the authenticity of the authentication code carrier having the authentication information. In addition, another example of the first authentication operation performed by the cloud server may compare a part or all of the authentication information with the data stored in the password database to confirm the authenticity of the authentication code carrier. If the cloud server determines that the authenticating code carrier is true, it can be known that the corresponding atomized medicine container is not forged, such that the user can use it with confidence.

Step S254: configuring the cloud server to determine the authenticity of the atomized medicine container or the atomized medicine, and to generate an authentication result signal. If the cloud server determines that the atomized medicine container is true, a corresponding authentication result signal is generated and transmitted to the user device. The method proceeds to configure the authentication module to transmit the authentication success signal to the antenna module through the second communication module.

Step S257: configuring the second authentication module to generate a wireless identification signal. In the present embodiment, the second authentication module 238 may serve as a reader medium of the authentication code carrier, and may also generate a radio frequency identification signal that can be read by the first authentication module.

Step S258: controlling the second authentication module to transmit the wireless identification signal to the antenna module of the atomization device. When the user needs to continuously use a plurality of atomized medicine, the user device may perform the first authentication operation on the plurality of authentication code carriers in advance, and after a plurality of corresponding authentication result signals S21 are obtained, the second authentication unit is configured to store the configuration for generating a plurality of wireless identification signals in the second memory, respectively. The user can quickly switch and select the different atomized medicine through the user device, so as to provide the user with more flexibility in the demand for medication.

Step S259: configuring the first authentication module of the atomization device to perform a second authentication operation related to the wireless identification signal. For example, when the antenna module receives the radio frequency identification signal generated by the second authentication module, the first wireless identifier analyzes the radio frequency identification signal, and the first authentication unit process the radio frequency identification signal to confirm the correctness of the radio frequency identification signal.

Step S259-1: configuring the first authentication unit to confirm the correctness of the radio frequency identification signal. If the radio frequency identification signal is determined to be correct, the method proceeds to step S259-4, enabling the control unit to control the power module to output driving voltage to drive the atomization element of the atomization device to atomize the atomized medicine. If the radio frequency identification signal is determined to be incorrect, the method proceeds to step S259-2, the authentication fails, and the method proceeds to step S259-3, where the method comes to an end. For example, if the first authentication unit determines that the wireless identification signal is incorrect, for example, the authentication unit cannot recognize the wireless identification signal, then the correspondingly output authentication failure signal may disable the control unit.

In this embodiment, in addition to providing a double authentication mechanism at the user device, an independent authentication mechanism is further provided at the atomization device, which greatly increases the difficulty of counterfeiting the authentication code carrier when compared with the previous embodiments, so as to ensure the security of data transmission, such that the counterfeit goods are not able to be used by the atomization device even if they are sold in the market, thus protecting the lives and properties of consumers.

Twenty-Second Embodiment

Reference is now made to FIG. 30, which is a flowchart of an authentication operation according to the twenty-second embodiment of the present invention. This embodiment is mainly to exemplify the details of the authentication process described from step S257 to step S259-4 in the atomization method of the twenty-first embodiment, the method may further include the following steps:

Step S260: configuring the second authentication module to generate a wireless identification signal. Specifically, the second authentication operation between the user device and the atomization device may be performed through the radio frequency identification signal. The user device may be a mobile electronic device having a near field communication (NFC) module, for simulating the operation of the RFID tag by using appropriate electronic circuits and corresponding antennas. Furthermore, in addition to the foregoing second authentication operation performed with the radio frequency identification signal, the Bluetooth authentication signal may also be transmitted between the first authentication module and the second authentication module.

Step S261: controlling the second authentication module to transmit the wireless identification signal to the antenna module of the atomization device. As described above, the user may perform step S262 in advance, transmitting the Bluetooth identification signal using the second communication module, or may perform step S263 in advance to transmit the radio frequency identification signal using the second communication module.

Step S264: configuring the first authentication module of the atomization device to perform a second authentication operation related to the wireless identification signal.

Step S265: configuring a first wireless identifier of the first authentication module to receive the wireless identification signal through the antenna module. When the antenna module receives the radio frequency identification signal or the Bluetooth identification signal generated by the second authentication module, the first wireless identifier analyzes the radio frequency identification signal or the Bluetooth identification signal, and the first authentication unit process the radio frequency identification signal or the Bluetooth identification signal to confirm the correctness of the radio frequency identification signal or the Bluetooth identification signal.

Step S266: configuring the first authentication unit to confirm the correctness of the radio frequency identification signal. If the radio frequency identification signal is determined to be correct, the method proceeds to step S269, enabling the control unit to control the power module to output driving voltage to drive the atomization element of the atomization device to atomize the atomized medicine. If the radio frequency identification signal is determined to be incorrect, the method proceeds to step S267, the authentication fails, and the method proceeds to step S268, where the process comes to an end. For example, if the first authentication unit determines that the wireless identification signal is incorrect, for example, the authentication unit cannot recognize the wireless radio frequency identification signal or the Bluetooth identification signal served as the wireless identification signal, then the correspondingly output authentication failure signal may disable the control unit.

In certain cases, the first authentication module may also have the capability of directly authenticating the authentication code carrier. For example, after the user device has performed the first authentication operation with the cloud server, the authentication information of the wireless identification chip may be rewritten so that the first wireless identifier may directly perform the second authentication operation on the authentication information of the wireless identification chip, so as to save the time for performing the first authentication operation through the user device and the cloud server every time the user needs to use the atomized medicine. On the other hand, when the user device is operated without network connection capability, or the user device is depleted of power, as long as the authentication code carrier has performed the first authentication operation, the user may still directly use the atomized medicine through the atomization device.

Twenty-Third Embodiment

Figure 31:
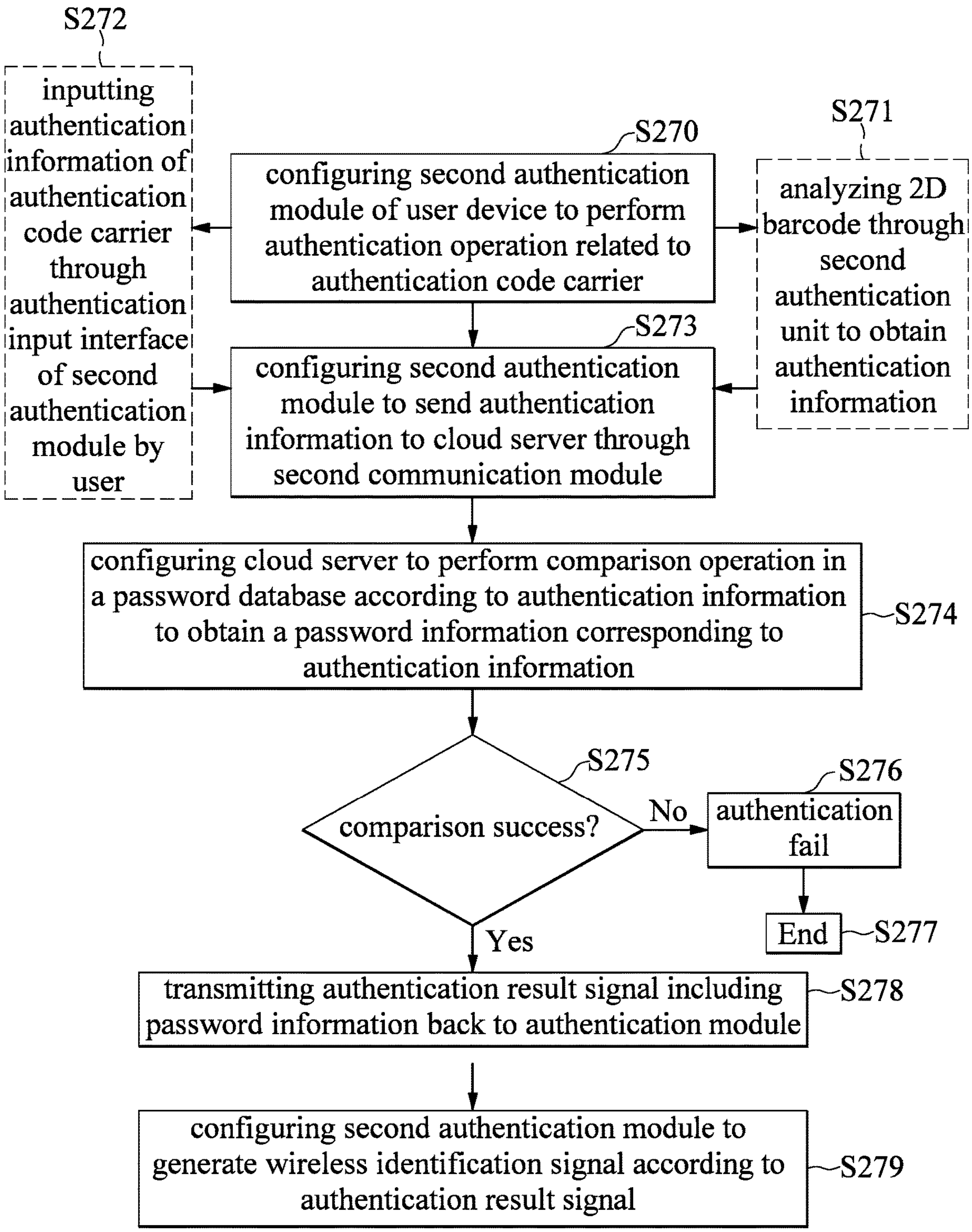
FIG. 31 is a flowchart of an authentication operation according to the twenty-third embodiment of the present invention.

Reference is now made to FIG. 31, which is a flowchart of an authentication operation according to the twenty-third embodiment of the present invention. This embodiment is mainly to exemplify the details of the authentication process described from step S252 to step S257 in the atomization method of the twenty-first embodiment, the method may further include the following steps:

Step S270: configuring the second authentication module of the user device to perform an authentication operation related to an authentication code carrier. As described above, the authentication operation may include identifying the two-dimensional barcode of the authentication code carrier with the user device, or the user may input the authentication code through the authentication code input interface. The specific configuration of the user device may refer to FIGS. 16, 17 and 18, respectively.

Optionally, the user may first perform step S271, obtaining the image of the 2D barcode through the image capturing module, and analyze the 2D barcode through the authentication unit to obtain the authentication information.

Step S273: configuring the second authentication module to send the authentication information to the cloud server through the second communication module. After the authentication information is obtained, the authentication information may be an anti-counterfeit identification code having a specific coding sequence, and is transmitted to the cloud server through the second communication module.

Step S274: configuring the cloud server to perform a comparison operation in a password database to obtain password information corresponding to the authentication information. Specifically, the password database may be pre-established according to a list of products sold by a pharmaceutical supplier, and the password database may have a plurality of unique authentication information, and multiple and unique passwords corresponding to the authentication information. After the cloud server receives the read authentication information, the cloud server then performs a comparison operation in the password database according to the authentication information to obtain password information corresponding to the authentication information. Since the password database may be instantly updated by the supplier, the atomized medicine containers purchased by users may be ensured that those have not been used and faked.

Step S275: determining whether the comparison is successful through the cloud server. After the above authentication operation, if the comparison operation of the cloud server succeeds in obtaining the password information, the method proceeds to step S278, the authentication result signal including the password information may be transmitted back to the authentication module. If the cloud server determines that the authenticating code carrier is true, it can be known that the corresponding atomized medicine container is not forged, such that the user can use it with confidence.

If the cloud server determines that the atomized medicine container is fake in step S275, a corresponding authentication result signal is generated and transmitted to the user device. The method proceeds to step S276, the authentication fails, and the authentication failure message may be displayed on the user device. The method proceeds to step S277, where the process comes to an end.

Step S279: configuring the second authentication module to generate a wireless identification signal. Specifically, the second authentication operation between the user device and the atomization device may be performed through the Bluetooth identification signal.

The present embodiment utilizes the camera module or the user interface that is commonly provided in an existing smart phone, and also improves the convenience of the authentication. In addition, the double authentication mechanism not only greatly increases the difficulty of counterfeiting the authentication code carrier, but also ensures the security of data transmission, such that the counterfeit goods are not able to be used by the atomization device even if they are sold in the market, thus protecting the lives and property of consumers.

The description of the different exemplary embodiments has been presented for purposes of illustration and description, and is not intended to be exhaustive or limited to the disclosure in the form disclosed. Many modifications and variations will be apparent to those of ordinary skill in the art. Further, different exemplary embodiments may provide different advantages as compared to other exemplary embodiments. The embodiment or embodiments selected are chosen and described in order to best explain the principles of the disclosure, the practical application, and to enable others of ordinary skill in the art to understand the disclosure for various embodiments with various modifications as are suited to the particular use contemplated.

What is claimed is:

1. An atomization system having a double authentication mechanism, comprising:

at least one atomized medicine container associated with an authentication code carrier, the at least one atomized medicine container containing an atomized medicine;

an atomization device, including:

an atomization module having an accommodating portion for accommodating the atomized medicine and an atomization element for atomizing the atomized medicine placed in the accommodating portion;

a power module for outputting a driving voltage to directly drive the atomization module;

a control unit connected to the power module, the control unit is configured to control the power module to output the driving voltage; and a first communication module for transmitting and receiving signals;

a user device, including:

a processor;

a second communication module connected to the processor, configured to pair with the first communication module, and connected to a cloud server through a network; and an authentication module connected to the processor, configured to perform an authentication operation related to the authentication code carrier, to determine an authenticity of the at least one atomized medicine container or the atomized drug through the cloud server, and to generate an authentication result signal correspondingly; and a value storing device, wherein the authentication module is configured to determine whether to control the second communication module through the processor to transmit an authentication success signal to the first communication module according to the authentication result signal, and wherein when the first communication module receives the authentication success signal, the control unit is configured to control the power module to output the driving voltage according to the authentication success signal, wherein the authentication code carrier further includes usage limit information, and the authentication operation includes configuring the authentication module to determine whether the usage limit information of the authentication code carrier reaches a predetermined limit amount, wherein the authentication operation includes further configuring the authentication module to update the usage limit information after the at least one atomized medicine container or the atomization medicine is determined to be true, and wherein the value storing device is configured to update the usage limit information of the authentication code carrier.

2. The atomization system having the double authentication mechanism according to claim 1, wherein the authentication module includes a wireless identifier, the authentication code carrier includes a wireless identification chip, wireless identifier is configured to obtain authentication information of the wireless identification chip, the cloud server is configured to determine the authenticity of the at least one atomized medicine container or the atomized medicine according to the authentication information, and to generate the authentication result signal correspondingly.

3. The atomization system having the double authentication mechanism according to claim 2, wherein the cloud server further includes a password database, and the authentication module is configured to transmit the authentication information to the cloud server through the second communication module, the cloud server performs a comparison operation in the password database according to the authentication information to obtain password information corresponding to the authentication information, and transmits the authentication module back to generate the authentication result signal including the password information.

4. The atomization system having the double authentication mechanism according to claim 1, wherein the authentication code carrier further includes a two-dimensional barcode, and the authentication module is further configured to identify the two-dimensional barcode to generate authentication information, and the authentication module is configured to transmit the authentication information to the cloud server, the cloud server performs a comparison operation in a password database according to the authentication information to obtain password information corresponding to the authentication information, and transmits the password information back to the authentication module to generate the authentication success signal containing the password information.

5. The atomization system having the double authentication mechanism according to claim 1, wherein the authentication module further includes an authentication code input interface, the authentication code input interface is configured for a user to input authentication information of the authentication code carrier, and the authentication module is further configured to determine the authenticity of the at least one atomized medicine container or the atomized medicine according to the authentication information, and to generate the authentication result signal correspondingly.

6. The atomization system having the double authentication mechanism according to claim 1, wherein the number of the at least one atomized medicine container is plural, and the plurality of atomized medicine containers are associated with the authentication code carrier.

7. An atomization system having a double authentication mechanism, comprising:

at least one atomized medicine container having an authentication code carrier, the at least one atomized medicine container containing an atomized medicine;

an atomization device, including:

an atomization module having an accommodating portion for accommodating the atomized medicine and an atomization element for atomizing the atomized medicine placed in the accommodating portion;

a power module for outputting a driving voltage to directly drive the atomization module;

a control unit connected to the power module, the control unit is configured to control the power module to output the driving voltage;

an antenna module for transmitting and receiving signals; and a first authentication module respectively connected to the control unit and the antenna module;

a user device, including:

a processor;

a communication module connected to the processor and connected to a cloud server through a network; and a second authentication module connected to the processor, configured to perform a first authentication operation associated with the authentication code carrier to determine the authenticity of the at least one atomized medicine container or the atomized medicine through the cloud server, and to generate an authentication result signal correspondingly; and a value storing device, wherein the second authentication module is configured to determine whether to generate a wireless identification signal according to the authentication result signal, wherein when the antenna module receives the wireless identification signal, the first authentication module is configured to perform a second authentication operation related to the wireless identification signal, and to further determine whether to enable the control unit to control the power module to output the driving voltage, wherein the authentication code carrier further includes usage limit information, and the first authentication operation includes configuring the second authentication module to determine whether the usage limit information of the authentication code carrier reaches a predetermined limit amount, wherein the first authentication operation includes further configuring the second authentication module to update the usage limit information after the at least one atomized medicine container or the atomization medicine is determined to be true, wherein the value storing device is configured to update the usage limit information of the authentication code carrier.

8. The atomization system having the double authentication mechanism according to claim 7, wherein the first authentication module includes a first wireless identifier configured to receive the wireless identification signal through the antenna module and to determine whether to enable the control unit to control the power module to output the driving voltage according to the wireless identification signal.

9. The atomization system having the double authentication mechanism according to claim 8, wherein the wireless identification signal is a radio frequency identification signal or a Bluetooth identification signal, and the second authentication module is configured to receive the authentication result signal and to determine whether to generate the radio frequency identification signal or the Bluetooth identification signal according to the authentication result signal.

10. The atomization system having the double authentication mechanism according to claim 7, wherein the second authentication module includes a second wireless identifier, and the authentication code carrier includes a wireless identification chip, and the second wireless identifier is configured to obtain authentication information of the wireless identification chip.

11. The atomization system having the double authentication mechanism according to claim 10, wherein the cloud server further includes a password database, and the authentication module is configured to transmit the authentication information to the cloud server through the second communication module, the cloud server performs a comparison operation in the password database according to the authentication information to obtain password information corresponding to the authentication information, and transmits the authentication module back to generate the authentication result signal including the password information.

12. The atomization system having the double authentication mechanism according to claim 7, wherein the authentication code carrier further includes a two-dimensional barcode, the second authentication module is further configured to identify the two-dimensional barcode to generate authentication information, the second authentication module is configured to transmit the authentication information to the cloud server, the cloud server performs a comparison operation in a password database according to the authentication information to obtain password information corresponding to the authentication information, and transmits the password information back to the authentication module to generate the authentication success signal containing the password information.

13. The atomization system having the double authentication mechanism according to claim 7, wherein the authentication module further includes an authentication code input interface configured for a user to input authentication information of the authentication code carrier, and the second authentication module is further configured to determine the authenticity of the at least one atomized medicine container or the atomized medicine according to the authentication information, and to generate the authentication result signal correspondingly.

14. The atomization system having the double authentication mechanism according to claim 7, wherein the number of the at least one atomized medicine container is plural, and the plurality of atomized medicine containers are associated with the authentication code carrier.

* * * * *